United States Patent
Singh et al.

(10) Patent No.: US 10,386,366 B2
(45) Date of Patent: Aug. 20, 2019

(54) ASSAYS FOR THE DETECTION OF ANTI-TNF DRUGS AND AUTOANTIBODIES

(71) Applicant: Nestec S.A., Vevey (CH)

(72) Inventors: Sharat Singh, Rancho Santa Fe, CA (US); Shui-Long Wang, San Diego, CA (US); Linda Ohrmund, San Diego, CA (US)

(73) Assignee: SOCIÉTÉ DES PRODUITS NESTLÉ S.A., Vevey (CH)

(*) Notice: Subject to any disclaimer, the term of this patent is extended or adjusted under 35 U.S.C. 154(b) by 56 days.

(21) Appl. No.: 15/297,878

(22) Filed: Oct. 19, 2016

(65) Prior Publication Data

US 2017/0184588 A1    Jun. 29, 2017

Related U.S. Application Data

(63) Continuation of application No. 14/336,955, filed on Jul. 21, 2014, now Pat. No. 9,506,920, which is a continuation of application No. 14/046,863, filed on Oct. 4, 2013, now Pat. No. 8,865,417, which is a continuation of application No. 13/441,727, filed on Apr. 6, 2012, now Pat. No. 8,574,855, which is a continuation of application No. PCT/US2010/054125, filed on Oct. 26, 2010.

(60) Provisional application No. 61/393,581, filed on Oct. 15, 2010, provisional application No. 61/389,682, filed on Oct. 4, 2010, provisional application No. 61/351,269, filed on Jun. 3, 2010, provisional application No. 61/345,567, filed on May 17, 2010, provisional application No. 61/324,635, filed on Apr. 15, 2010, provisional application No. 61/262,877, filed on Nov. 19, 2009, provisional application No. 61/255,048, filed on Oct. 26, 2009.

(51) Int. Cl.
| | |
|---|---|
| *G01N 33/50* | (2006.01) |
| *G01N 33/68* | (2006.01) |
| *G01N 33/564* | (2006.01) |

(52) U.S. Cl.
CPC ....... *G01N 33/564* (2013.01); *G01N 33/5091* (2013.01); *G01N 33/6854* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,459,359 A | 7/1984 | Neurath |
| 4,857,456 A | 8/1989 | Urist |
| 4,965,069 A | 10/1990 | Quash et al. |
| 5,094,740 A | 3/1992 | Brandley et al. |
| 5,223,395 A | 6/1993 | Gero |
| 5,231,024 A | 7/1993 | Moeller et al. |
| 5,582,998 A | 12/1996 | Adolf et al. |
| 5,698,419 A | 12/1997 | Wolpe et al. |
| 5,795,967 A | 8/1998 | Aggarwal et al. |
| 5,837,242 A | 11/1998 | Holliger et al. |
| 6,284,471 B1 | 9/2001 | Le et al. |
| 6,309,888 B1 | 10/2001 | Holvoet et al. |
| 6,444,461 B1 | 9/2002 | Knapp et al. |
| 6,906,183 B2 | 6/2005 | Romisch |
| 7,189,515 B2 | 3/2007 | Buechler et al. |
| 7,276,477 B2 | 10/2007 | Osslund et al. |
| 7,542,502 B2 | 4/2009 | Hellendoorn et al. |
| 7,601,335 B2 | 10/2009 | McCutcheon et al. |
| 7,611,702 B2 * | 11/2009 | Fischkoff ........... A61K 39/3955 424/130.1 |
| 7,662,569 B2 | 2/2010 | Targan et al. |
| 8,574,855 B2 | 11/2013 | Singh et al. |
| 8,865,417 B2 | 10/2014 | Singh et al. |
| 9,465,027 B2 | 10/2016 | Hauenstein et al. |
| 9,506,920 B2 | 11/2016 | Singh et al. |
| 9,784,748 B2 | 10/2017 | Wang et al. |
| 2002/0182651 A1 | 12/2002 | Patricelli |
| 2003/0040027 A1 | 2/2003 | Ritter et al. |
| 2003/0077246 A1 | 4/2003 | Welcher et al. |
| 2004/0022792 A1 | 2/2004 | Klinke et al. |
| 2004/0157782 A1 | 8/2004 | Doronina |
| 2005/0054005 A1 | 3/2005 | Ellis et al. |
| 2005/0181483 A1 | 8/2005 | Sawyer et al. |
| 2006/0003384 A1 | 1/2006 | Wagner et al. |

(Continued)

FOREIGN PATENT DOCUMENTS

| | | |
|---|---|---|
| CN | 102695955 A | 9/2012 |
| CN | 103782172 A | 5/2014 |

(Continued)

OTHER PUBLICATIONS

Aarden, L. et al., "Immunogenicity of anti-tumor necrosis factor antibodies—toward improved methods of anti-antibody measurement," Current Opinion in Immunology, 20(4): 431-435, 2008.

(Continued)

*Primary Examiner* — Changhwa J Cheu

(74) *Attorney, Agent, or Firm* — Kilpatrick Townsend & Stockton LLP

(57) ABSTRACT

The present invention provides assays for detecting and measuring the presence or level of anti-TNFα drug therapeutics and autoantibodies in a sample. The present invention is useful for optimizing therapy and monitoring patients receiving anti-TNFα drug therapeutics to detect the presence or level of autoantibodies (e.g., HACA and/or HAHA) against the drug.

22 Claims, 30 Drawing Sheets

Specification includes a Sequence Listing.

(56) References Cited

U.S. PATENT DOCUMENTS

| | | | |
|---|---|---|---|
| 2006/0078944 A1 | 4/2006 | Kuai et al. |
| 2006/0110407 A1 | 5/2006 | Stopera et al. |
| 2006/0240480 A1 | 10/2006 | Curdt et al. |
| 2006/0253263 A1 | 11/2006 | Meshkin |
| 2007/0077249 A1 | 4/2007 | Silence et al. |
| 2008/0280311 A1 | 11/2008 | Strohner |
| 2008/0286774 A1 | 11/2008 | Turteltaub et al. |
| 2009/0035216 A1 | 2/2009 | Svenson et al. |
| 2009/0162374 A1 | 6/2009 | Geraghty et al. |
| 2009/0234202 A1 | 9/2009 | Goix et al. |
| 2009/0275496 A1 | 11/2009 | Baldwin et al. |
| 2010/0130367 A1 | 5/2010 | Murthy et al. |
| 2010/0330156 A1 | 12/2010 | Liu |
| 2012/0329172 A1 | 12/2012 | Singh et al. |
| 2013/0266963 A1 | 10/2013 | Hauenstein et al. |
| 2013/0295685 A1 | 11/2013 | Singh et al. |
| 2013/0344621 A1 | 12/2013 | Wang et al. |
| 2014/0045276 A1 | 2/2014 | Singh et al. |
| 2014/0051184 A1 | 2/2014 | Singh et al. |
| 2014/0057367 A1 | 2/2014 | Singh et al. |
| 2014/0186973 A1 | 7/2014 | Hauenstein et al. |
| 2015/0024404 A1 | 1/2015 | Singh et al. |
| 2017/0176433 A1 | 6/2017 | Hauenstein et al. |
| 2017/0328923 A1 | 11/2017 | Salbato et al. |

FOREIGN PATENT DOCUMENTS

| | | |
|---|---|---|
| EP | 0440044 | 8/1991 |
| EP | 0492448 A1 | 7/1992 |
| EP | 0642021 A2 | 3/1995 |
| EP | 0882984 A1 | 12/1998 |
| EP | 1237926 B1 | 9/2002 |
| EP | 1769244 | 4/2007 |
| EP | 1902320 | 3/2008 |
| EP | 2 676 137 | 12/2014 |
| JP | H05-000096 A2 | 1/1993 |
| JP | 05-066222 A2 | 3/1993 |
| JP | H07-110331 A2 | 4/1995 |
| JP | 7-140144 | 6/1995 |
| JP | H11-500607T A | 1/1999 |
| JP | 2001-249127 A2 | 9/2001 |
| JP | 2007-147367 | 6/2007 |
| JP | 2013-508739 | 3/2013 |
| WO | 96/020219 A1 | 7/1996 |
| WO | 2005/019271 A1 | 3/2005 |
| WO | 2006/004958 A2 | 1/2006 |
| WO | 2007/009469 A2 | 1/2007 |
| WO | 2009/091240 A1 | 7/2009 |
| WO | 2011/056590 A1 | 5/2011 |
| WO | 2012/054532 A1 | 4/2012 |
| WO | 2012/154253 A1 | 11/2012 |
| WO | 2013/006810 A1 | 1/2013 |
| WO | 2014/083520 A1 | 6/2014 |

OTHER PUBLICATIONS

Arcangelo & Peterson, Pharmacotherapeutics for Advanced Practice: A Practical Approach, Philadelphia, PA, 536:18, 2006.

Arends, S. et al., "The formation of autoantibodies and antibodies to TNF-α blocking agents in relation to clinical response in patients with ankylosing spondylitis," Clinical and Experimental Rheumatology, 28(5):661-8, 2010.

Aybay, C. et al., "Demonstration of specific antibodies against infliximab induced during treatment of a patient with ankylosing spondylitis," Rheumatology International, Clin. and Exper. Invest., 26(5):473-480, 2006.

Bendtzen, K. et al., "Individualized monitoring of drug bioavailability and immunogenicity in rheumatoid arthritis patients treated with the tumor necrosis factor alpha inhibitor infliximab," Arthritis & Rheumatism, 54(12):3782-3789, 2006.

Brekke, O. et al., "Therapeutic antibodies for human diseases at the dawn of the twenty-first century," Nature Reviews Drug Discovery, 2:52-62, 2003.

Bourdage et al., "An affinity capture elution (ACE) assay for detection of anti-drug antibody to monoclonal antibody therapeutics in the presence of high levels of drug," J. Immunol. Methods, 327(1-2):10-17, 2007.

Cheifetz, A. et al., "Monoclonal antibodies: immunogenicity, and associated infusion reactions," Mount Sinai J. Medicine, 72(4):250-256, 2005.

Chernesky & Mahony, "Immunoassays: principles and assay design," in Virology Methods Manuals, Mahy & Kangro (Eds.), pp. 123-124, San Diego, CA: Academic Press Inc., 1996.

Cisbio Bioassays, "HTRF human kappa and lambda MAb assay: A new solution for human IgG characterisation," 2009, URL: http://www.biolab.cn/plus/view-241835-1.html, Accessed on Feb. 20, 2014.

Deventer, S. et al., "Anti-tumour necrosis factor therapy in Crohn's disease: Where are we now?" Gut, 51(3):362-63, 2002.

Elliott, M. et al., "Repeated therapy with monoclonal antibody to tumour necrosis factor alpha (cA2) in patients with rheumatoid arthritis," Lancet, 334(8930):1125-1127, 1994.

Finckh et al., "Influence of anti-infliximab antibodies and residual infliximab concentrations on the occurrence of acquired drug resistance to infliximab in rheumatoid patients," Joint Bone Spine, 77:313-318, 2010.

Flood, J., "Tumor necrosis factor inhibitors in the treatment of chronic inflammatory diseases: A review of immunogenicity and potential implications," Suppl. to Managed Care, 18(4):1-5, 2009.

Gisbert, Javier et al., "Loss of Response and Requirement of Infliximab Dose Intensification in Crohn's Disease: A Review," Journal of Gastroenterology, 104:760-767, 2009.

Hagg, D. et al., "Measurement and biological correlates of antibody bioactivity during antibody immunotherapies," J. Immunol. Meth., 219(1-2): 7-21, 1998.

Harlow, E. and Lane, D., "Antibodies: A Laboratory Manual," Cold Spring Harbor Laboratory Press, Cold Spring Harbor, NY, pp. 7-10, 1988.

Harris, Quantitative Chemical Analysis, Sixth Ed., New York, W.H. Freeman Co., p. 85-86, 2003.

Harris, Quantitative Chemical Analysis, Sixth Ed., New York, W.H. Freeman Co., p. 91, 2003.

Holmskov-Nielsen, U. et al., "Immune complex formation analysed by high-performance size exclusion chromatography (HPLC-SEC) using either 125I-labelled antigen or enzyme-linked immunosorbent assay (ELISA) for detection," Immunology, 51(4):809-14, 1984.

Hosono, M. et al., "Human-mouse chimeric antibodies show low reactivity with human anti-murine antibodies HAMA," British J. Cancer, 65(2):197-200, 1992.

Invitrogen, "Looking on the bright side with Alexa Fluor® secondary antibodies," 2008, URL http://www.jimmunol.org/content/181/3/local/advertising.pdf, retrieved on Oct. 11, 2013.

Kawate, T. et al., "Fluorescence-detection size-exclusion chromatography for precrystallization screening of integral membrane proteins," Structure, 14:673-681, 2006.

Koren et al., "Recommendations on risk-based strategies for detection and characterization of antibodies against biotechnology products," Journal of Immunological Methods, 333:1-9, 2008.

Lofgren, J. et al., "Detection of neutralizing anti-therapeutic protein antibodies in serum or plasma samples containing high levels of the therapeutic protein," J. Immunol. Meth., 308(1-2):101-108, 2006.

Maier, K. et al., "Fluorescent HPLC assay for 20-HETE and other P-450 metabolites of arachidonic acid," A. J. Physiol. Heart Circ. Physiol., 279:H865-H871, 2000.

Molecular Probes, Inc., "BioParticles® Fluorescent Particles and Opsonizing Reagents," Product Information, Mar. 9, 2001, pp. 1-3, retrieved online from http://tools.lifetechnologies.com/content/sfs/manuals/mp02701.pdf on Aug. 12, 2014.

Murtazina, N.R. et al., "Immunochemical detection of sulfamethazine in river water and medicines," Chemotherapeutic Magazine, 39(8):93-97, 2005.

O'Keefe, Michael, Ed., Residue Analysis in Food Principles and Applications, Amsterdam, Hardwood Academic Publishers, p. 20, 2000.

Palframan R. et al., "Use of biofluorescence imaging to compare the distribution of certolizumab pegol, adalimumab, and infliximab in

(56) References Cited

OTHER PUBLICATIONS the inflamed paws of mice with collagen-induced arthritis," J. Immunol. Methods., 348(1-2):36-41, 2009.
Panchuk-Voloshina, N. et al., "Alexa dyes, a series of new fluorescent dyes that yield exceptionally bright, photostable conjugates," J. Histochem & Cytochem., 47(9):1179-1188, 1999.
Patton et al., "An acid dissociation bridging ELISA for detection of antibodies directed against therapeutic proteins in the presence of antigen," J. Immunol. Meth., 304(1-2):189-195, 2005.
Reynolds, J.C. et al., "Anti-murine antibody response to mouse monoclonal antibodies: Clinical findings and implications," Int'l. J. Radiation Applications and Instrumentation, Part B: Nuclear Medicine and Biology, 16(2):121-125, 1989.
Rojas, J.R. et al., "Formation, distribution, and elimination of infliximab and anti-infliximab immune complexes in cynomolgus monkeys," JPET, 313(2):578-585, 2005.
Scallon, B. et al., "Binding and functional comparisons of two types of tumor necrosis factor antagonists," J. Pharmacol. Exper. Ther., 301(2):418-426, 2002.
Sickert, D. et al., "Improvement of drug tolerance in immunogenicity testing by acid treatment on Biacore," J. Immunol. Meth., 334(1-2):29-36, 2008.
Smith et al., "Detection of antibodies against therapeutic proteins in the presence of residual therapeutic protein using a solid-phase extraction with acid dissociation (SPEAD) sample treatment prior to ELISA," Regulatory Toxicology and Pharmacology, 49(3): 230-237, 2007.
Steenholdt, C. et al. "Measurement of infliximab and anti-infliximab antibody levels can help distinguish maintenance versus loss of response," Gastroenterology & Hepatology, 8(2):131-134, 2012.
Svenson, M. et al., "Monitoring patients treated with anti-TNFα biopharmaceuticals: assessing serum infliximab and anti-infliximab antibodies," Rheumatology, 46:1828-34, 2007.
Tayyab, S. et al., "Size exclusion chromatography and size exclusion HPLC of proteins," Biochemical Education, 19(3):149-152, 1991.
Tiittanen, M. et al., "Anti-insulin activity in IgG-fractions from children with newly-diagnosed type 1 diabetes and negative for insulin autoantibodies," Autoimmunity, 37(I): 45-9, 2004.
U.S. Department of Health and Human Services et al., "Guidance for industry assay development for immunogenicity testing of therapeutic proteins," Draft Guidance, 2009, 24 pages, retrieved from <http://www.fda.gov/Drugs/GuidanceComplianceRegulatoryInformation/Guidances/UCM192750.
Van Der Laken, C. et al., "Imaging and serum analysis of immune complex formation of radiolabeled infliximab and anti-infliximab in responders and non-responders to therapy for rheumatoid arthritis," Ann. Rheum. Dis., 66(2):253-256, 2007.
Van Schouwenburg, P. et al., "A novel method for the detection of antibodies to adalimumab in the presence of drug reveals "hidden" immunogenicity in rheumatoid arthritis patients," J. Immunol. Meth., 362(1-2):82-88, 2010.
Wang, S. et al., "Analysis of anti-drug antibodies (ADA) to adalimumab in patient serum using a novel homogeneous mobility shift assay," Am. J. Gastro., 105(Suppl. 1): S444-S445, 2010.
Benucci, M. et al., "No correlations between the development of specific IgA and IgM antibodies against anti-TNF blocking agents, disease activity and adverse side reactions in patients with Rheumatoid arthritis," The Open Rheumatology Journal, 7:75-80, 2013.
English Machine Translation of CN 103782172 A; published May 7, 2014, 47 pages.
English Machine Translation of JP 07-140144; published Jun. 2, 1995, abstract only, 1 page.
English Machine Translation of JP 2013-508739; published May 7, 2013, 53 pages.
Clark, K. et al., "Production of recombinant soluble human integrin α4β1," FEBS Letters, 471:182-186, 2000.
Kim, M. et al., "Comparative analyses of complex formation and binding sites between Human Tumor Necrosis Factor-alpha and its three antagonists elucidate their different neutralizing mechanisms," J. Mol. Biol., 374:1374-88, 2007.
Salbato, J. et al., "Tu1301 Validation of a Homogenous Mobility Shift Assay (HMSA) for the Measurement of Vedolizumab (VLM) and Anti-VLM Antibodies in Inflammatory Bowel Disease (IBD) Patient Serum," Gastroenterology, 148(4):S-852, 2015.
Santora, L. et al., "Characterization of noncovalent complexes of recombinant human monoclonal antibody and antigen using cation exchange, size exclusion chromatography, and BIAcore," Analytical Biochemistry, 299:119-129, 2001.
Wang, S. et al., "Development and validation of a homogeneous mobility shift assay for the measurement of infliximab and antibodies-to-infliximab levels in patient serum," Journal of Immunological Methods, 382:177-188, 2012.
Wang, S. et al., "Monitoring of adalimumab and antibodies-to-adalimumab levels in patient serum by the homogeneous mobility shift assay," Journal of Pharmaceutical and Biomedical Analysis, 78-79:39-44, 2013.

* cited by examiner

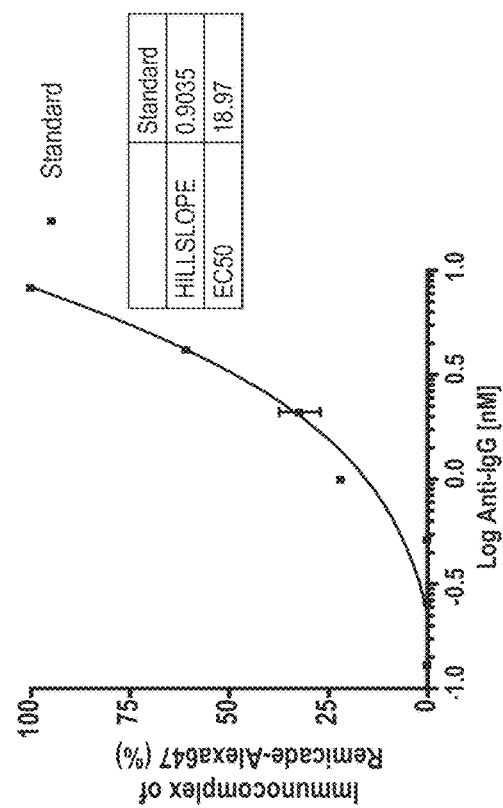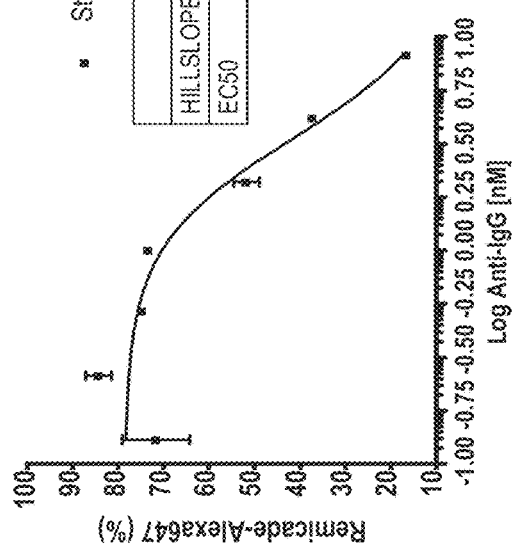
FIG. 7

| Acession # | Bridge ELISA | | HACA Shift Assay | Mobility Shift Assay (4% Serum) | |
|---|---|---|---|---|---|
| | Quantitative Result | Qualitative Result | | HACA Area/Remicade-647 Area | Remicade (nM) |
| SK07010477 | 22.26 | Positive | Positive | 0.78 | 3.33 |
| SK07060083 | 1.41 | Negative | Negative | 0.1 | 4.06 |
| SK07070083 | 1.41 | Negative | Negative | 0.1 | 8.81 |
| SK07070305 | 1.41 | Negative | Positive | 0.46 | 7.34 |
| SK07070595 | 1.41 | Negative | Positive | 0.25 | 8.35 |
| SK07071213 | 2.48 | Positive | Positive | 0.16 | 5.30 |
| SK07081127 | 22.07 | Positive | Positive | 0.28 | 3.00 |
| SK07110635 | 1.41 | Negative | Positive | 0.18 | >66.7 |
| SK07141447 | 2.62 | Positive | Positive | 0.42 | 2.43 |
| SK07171059 | 10.11 | Positive | Positive | 18.02 | 2.59 |
| SK07171095 | 10.03 | Positive | Positive | 0.24 | 2.24 |
| SK07210210 | 9.26 | Positive | Positive | 0.8 | <0.67 |
| SK07231216 | 25.58 | Positive | Positive | Complete Shift | 1.34 |
| SK07310149 | 2.74 | Positive | Positive | 0.21 | <0.67 |
| SK08040168 | 22.21 | Positive | Positive | Complete Shift | <0.67 |
| SK08051035 | 9.72 | Positive | Positive | 8.7 | 1.89 |
| SK08070307 | 2.49 | Positive | Positive | 0.23 | 3.14 |
| SK08120222 | 9.2 | Positive | Positive | 0.25 | <0.67 |
| SK08260093 | 23.15 | Positive | Positive | 0.48 | 1.04 |
| SK08260783 | 2.67 | Positive | Positive | 0.25 | 3.30 |
| 62.5ng Remicade - 647 | | | | 0.12 | |
| 100ng TNF - 647 | | | | | <0.67 |

FIG. 9

|  | Bridge HACA Assay | Biotin and DIG-Based Homogeneous Bridging ELISA | HACA Assay of the Present Invention |
|---|---|---|---|
| Assay Format | HRP-Avidin / Bio-Remicade / HACA / Remicade | HRP-anti-DIG / DIG-Remicade / HACA / Bio-Remicade / Avidin | Fl-Remicade + HACA → Complex |
| Non-specific Background Interference | High | High | Low |
| Sensitivity | Low | Medium | High |
| Possibility of False-Positive and False-Negative | High | High | Low |
| IgG4 HACA Detection | No | No | Yes |
| Ig Isotype identification | No | No | Yes |
| Tolerance of Drug in the Sample | Poor | Poor | Good |

FIG. 10

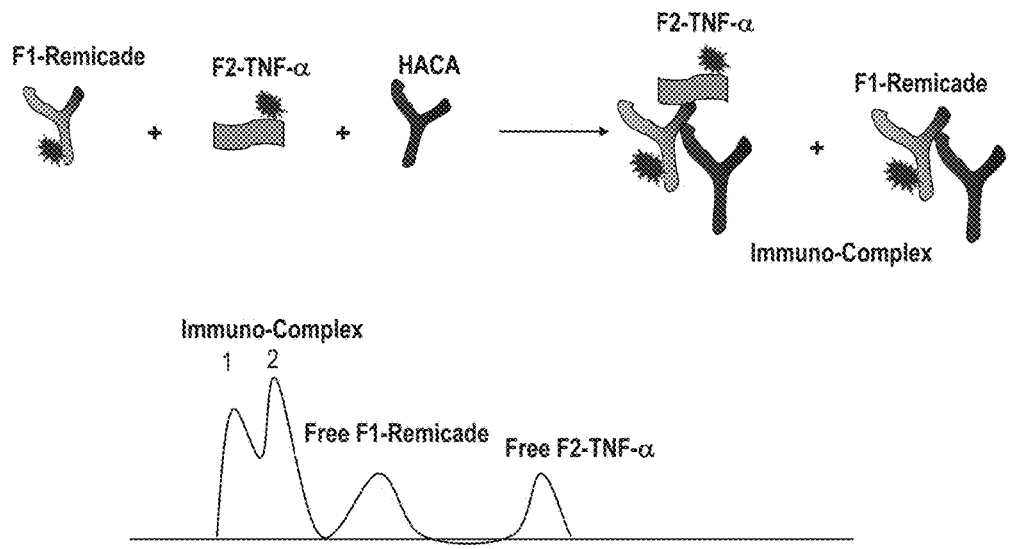
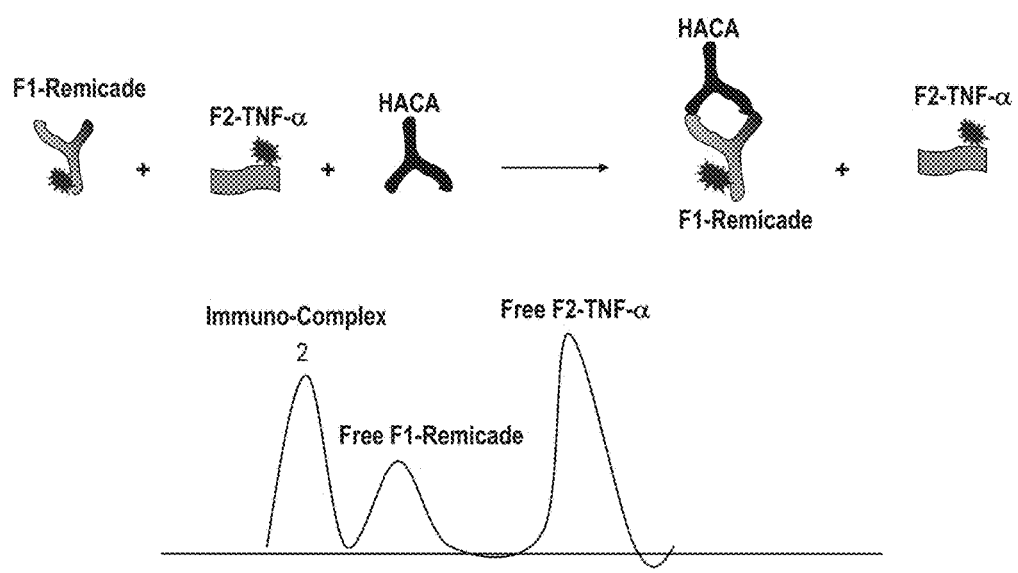
FIG. 17

ASSAYS FOR THE DETECTION OF ANTI-TNF DRUGS AND AUTOANTIBODIES

CROSS-REFERENCE TO RELATED APPLICATIONS

The present application is a continuation of U.S. Ser. No. 14/336,955 filed Jul. 21, 2014 (Allowed); which is a continuation U.S. Ser. No. 14/046,863 filed Oct. 4, 2013 (now U.S. Pat. No. 8,865,417); which is a continuation of U.S. Ser. No. 13/441,727 filed Apr. 6, 2012 (now U.S. Pat. No. 8,574,855); which is a continuation of PCT/US2010/054125 filed Oct. 26, 2010; which claims priority to US Provisional Application Nos.: 61/393,581 filed Oct. 15, 2010; 61/389,672 filed Oct. 4, 2010; 61/351,269 filed Jun. 3, 2010; 61/345,567 filed May 17, 2010; 61/324,635 filed Apr. 15, 2010; 61/262,877 filed Nov. 19, 2009; and 61/255,048 filed Oct. 26, 2009; the disclosures of which are hereby incorporated by reference in their entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-182-9.TXT, created on Aug. 12, 2014, 4,096 bytes, machine format IBM-PC, MS-Windows operating system, is hereby incorporated by reference in its entirety for all purposes.

BACKGROUND OF THE INVENTION

Autoimmune disorders are a significant and widespread medical problem. For example, rheumatoid arthritis (RA) is an autoimmune disease affecting more than two million people in the United States. RA causes chronic inflammation of the joints and typically is a progressive illness that has the potential to cause joint destruction and functional disability. The cause of rheumatoid arthritis is unknown, although genetic predisposition, infectious agents and environmental factors have all been implicated in the etiology of the disease. In active RA, symptoms can include fatigue, lack of appetite, low grade fever, muscle and joint aches and stiffness. Also during disease flare ups, joints frequently become red, swollen, painful and tender, due to inflammation of the synovium. Furthermore, since RA is a systemic disease, inflammation can affect organs and areas of the body other than the joints, including glands of the eyes and mouth, the lung lining, the pericardium, and blood vessels.

Traditional treatments for the management of RA and other autoimmune disorders include fast acting "first line drugs" and slower acting "second line drugs." The first line drugs reduce pain and inflammation. Example of such first line drugs include aspirin, naproxen, ibuprofen, etodolac and other non-steroidal anti-inflammatory drugs (NSAIDs), as well as corticosteroids, given orally or injected directly into tissues and joints. The second line drugs promote disease remission and prevent progressive joint destruction and are also referred to as disease-modifying anti-rheumatic drugs or DMARDs. Examples of second line drugs include gold, hydrochloroquine, azulfidine and immunosuppressive agents, such as methotrexate, azathioprine, cyclophosphamide, chlorambucil and cyclosporine. Many of these drugs, however, can have detrimental side-effects. Thus, additional therapies for rheumatoid arthritis and other autoimmune disorders have been sought.

Tumor necrosis factor alpha (TNF-α) is a cytokine produced by numerous cell types, including monocytes and macrophages, that was originally identified based on its ability to induce the necrosis of certain mouse tumors. Subsequently, a factor termed cachectin, associated with cachexia, was shown to be identical to TNF-α. TNF-α has been implicated in the pathophysiology of a variety of other human diseases and disorders, including shock, sepsis, infections, autoimmune diseases, RA, Crohn's disease, transplant rejection and graft-versus-host disease.

Because of the harmful role of human TNF-α (hTNF-α) in a variety of human disorders, therapeutic strategies have been designed to inhibit or counteract hTNF-α activity. In particular, antibodies that bind to, and neutralize, hTNF-α have been sought as a means to inhibit hTNF-α activity. Some of the earliest of such antibodies were mouse monoclonal antibodies (mAbs), secreted by hybridomas prepared from lymphocytes of mice immunized with hTNF-α (see e.g., U.S. Pat. No. 5,231,024 to Moeller et al.). While these mouse anti-hTNF-α antibodies often displayed high affinity for hTNF-α and were able to neutralize hTNF-α activity, their use in vivo has been limited by problems associated with the administration of mouse antibodies to humans, such as a short serum half-life, an inability to trigger certain human effector functions, and elicitation of an unwanted immune response against the mouse antibody in a human (the "human anti-mouse antibody" (HAMA) reaction).

More recently, biological therapies have been applied to the treatment of autoimmune disorders such as rheumatoid arthritis. For example, four TNFα inhibitors, REMICADE™ (infliximab), a chimeric anti-TNFα mAb, ENBREL™ (etanercept), a TNFR-Ig Fc fusion protein, HUMIRA™ (adalimumab), a human anti-TNFα mAb, and CIMZIA® (certolizumab pegol), a PEGylated Fab fragment, have been approved by the FDA for treatment of rheumatoid arthritis. CIMZIA® is also used for the treatment of moderate to severe Crohn's disease (CD). While such biologic therapies have demonstrated success in the treatment of rheumatoid arthritis and other autoimmune disorders such as CD, not all subjects treated respond, or respond well, to such therapy. Moreover, administration of TNFα inhibitors can induce an immune response to the drug and lead to the production of autoantibodies such as human anti-chimeric antibodies (HACA), human anti-humanized antibodies (HAHA), and human anti-mouse antibodies (HAMA). Such HACA, HAHA, or HAMA immune responses can be associated with hypersensitive reactions and dramatic changes in pharmacokinetics and biodistribution of the immunotherapeutic TNFα inhibitor that preclude further treatment with the drug. Thus, there is a need in the art for assays to detect the presence of anti-TNFα biologics and/or their autoantibodies in a patient sample to monitor TNFα inhibitor therapy and to guide treatment decisions. The present invention satisfies this need and provides related advantages as well.

BRIEF SUMMARY OF THE INVENTION

TNFα has been implicated in inflammatory diseases, autoimmune diseases, viral, bacterial and parasitic infections, malignancies, and/or neurodegenerative diseases and is a useful target for specific biological therapy in diseases, such as rheumatoid arthritis and Crohn's disease. TNFα inhibitors such as anti-TNFα antibodies are an important class of therapeutics. Assay methods are needed to detect the presence of anti-TNFα biologics and/or their autoantibodies.

As such, in one embodiment, the present invention provides a method for detecting the presence or level of an anti-TNFα drug in a sample, comprising:
  (a) contacting labeled TNFα with a sample having or suspected of having an anti-TNFα drug to form a labeled complex (i.e., immuno-complex or conjugate) with the anti-TNFα drug (i.e., wherein the labeled TNFα and anti-TNFα drug are not covalently attached to each other);
  (b) subjecting the labeled complex to size exclusion chromatography to separate the labeled complex (e.g., from free labeled TNFα); and
  (c) detecting the labeled complex, thereby detecting the presence or level of an anti-TNFα drug.

In certain instances, the methods are useful for measuring the levels of REMICADE™ (infliximab), ENBREL™ (etanercept), HUMIRA™ (adalimumab), and CIMZIA® (certolizumab pegol) in a sample, e.g., from a subject receiving such anti-TNFα drug therapy.

In another embodiment, the present invention provides a method for detecting the presence or level of an autoantibody to an anti-TNFα drug in a sample, comprising:
  (a) contacting a labeled anti-TNFα drug with a sample having or suspected of having an autoantibody to the anti-TNFα drug to form a labeled complex (i.e., immuno-complex or conjugate) with the autoantibody (i.e., wherein the labeled anti-TNFα drug and autoantibody are not covalently attached to each other);
  (b) subjecting the labeled complex to size exclusion chromatography to separate the labeled complex (e.g., from free labeled anti-TNFα drug); and
  (c) detecting the labeled complex, thereby detecting the presence or level of the autoantibody.

In certain instances, the methods are useful for measuring the levels of autoantibodies including, but not limited to, human anti-chimeric antibodies (HACA), human anti-humanized antibodies (HAHA), and human anti-mouse antibodies (HAMA) in a sample, e.g., from a subject receiving anti-TNFα drug therapy.

In yet another embodiment, the present invention provides a method for detecting the presence or level of an autoantibody to an anti-TNFα drug in a sample, comprising:
  (a) contacting a labeled anti-TNFα drug and labeled TNFα with a sample having or suspected of having an autoantibody to the anti-TNFα drug to form a first labeled complex (i.e., immuno-complex or conjugate) between the labeled anti-TNFα drug, the labeled TNFα, and the autoantibody (i.e., wherein the components of the first labeled complex are not covalently attached to each other) and a second labeled complex (i.e., immuno-complex or conjugate) between the labeled anti-TNFα drug and the autoantibody (i.e., wherein the components of the second labeled complex are not covalently attached to each other), wherein the labeled anti-TNFα drug and the labeled TNFα comprise different labels;
  (b) subjecting the first labeled complex and the second labeled complex to size exclusion chromatography to separate the first labeled complex and the second labeled complex (e.g., from each other and from free labeled TNFα and free labeled anti-TNFα drug); and
  (c) detecting the first labeled complex and the second labeled complex, thereby detecting the presence or level of a non-neutralizing form of the autoantibody (i.e., wherein the autoantibody does not interfere with the binding between the anti-TNFα drug and TNFα) when both the first labeled complex and the second labeled complex are present, and detecting the presence or level of a neutralizing form of the autoantibody (i.e., wherein the autoantibody interferes with the binding between the anti-TNFα drug and TNFα) when only the second labeled complex is present.

In certain instances, the methods are useful for measuring the levels of autoantibodies including, but not limited to, human anti-chimeric antibodies (HACA), human anti-humanized antibodies (HAHA), and human anti-mouse antibodies (HAMA) in a sample, e.g., from a subject receiving anti-TNFα drug therapy.

In a related embodiment, the present invention provides a method for detecting the presence or level of an autoantibody to an anti-TNFα drug in a sample, comprising:
  (a) contacting a labeled anti-TNFα drug with a sample having or suspected of having an autoantibody to the anti-TNFα drug to form a first labeled complex (i.e., immuno-complex or conjugate) between the labeled anti-TNFα drug and the autoantibody (i.e., wherein the labeled anti-TNFα drug and autoantibody are not covalently attached to each other);
  (b) subjecting the first labeled complex to a first size exclusion chromatography to separate the first labeled complex (e.g., from free labeled anti-TNFα drug);
  (c) detecting the first labeled complex, thereby detecting the presence or level of the autoantibody;
  (d) contacting labeled TNFα with the first labeled complex to form a second labeled complex (i.e., immuno-complex or conjugate) between the labeled anti-TNFα drug and the labeled TNFα (i.e., wherein the labeled anti-TNFα drug and the labeled TNFα are not covalently attached to each other), wherein the labeled anti-TNFα drug and the labeled TNFα comprise different labels;
  (e) subjecting the second labeled complex to a second size exclusion chromatography to separate the second labeled complex (e.g., from free labeled TNFα); and
  (f) detecting the second labeled complex, thereby detecting the presence or level of a neutralizing form of the autoantibody (i.e., wherein the autoantibody interferes with the binding between the anti-TNFα drug and TNFα).

In certain instances, the methods are useful for measuring the levels of autoantibodies including, but not limited to, human anti-chimeric antibodies (HACA), human anti-humanized antibodies (HAHA), and human anti-mouse antibodies (HAMA) in a sample, e.g., from a subject receiving anti-TNFα drug therapy.

In another embodiment, the present invention provides a method for determining an effective amount of an anti-TNFα drug for a subject receiving therapy with the anti-TNFα drug, the method comprising:
  (a) measuring the level of the anti-TNFα drug in a first sample from the subject, comprising:
    (i) contacting the first sample with an amount of a labeled TNFα to form a first complex comprising the labeled TNFα with the anti-TNFα drug; and
    (ii) detecting the first complex by size exclusion chromatography,
  thereby measuring the level of the anti-TNFα drug;
  (b) measuring the level of an autoantibody to the anti-TNFα drug in a second sample from the subject, comprising:
    (i) contacting the second sample with an amount of a labeled anti-TNFα drug to form a second complex comprising the labeled anti-TNFα drug with the autoantibody; and (ii) detecting the second complex by size exclusion chromatography, thereby measuring the level of the autoantibody; and (c) subtracting the level of the autoantibody measured in step (b) from the level of the anti-TNFα drug measured in step (a), thereby determining the effective amount of the anti-TNFα drug.

In another embodiment, the present invention provides a method for optimizing the therapeutic amount of an anti-TNFα drug in a subject receiving therapy with the anti-TNFα drug, the method comprising:

(a) determining an effective amount of the anti-TNFα drug in accordance with a method of the present invention;

(b) comparing the effective amount of the anti-TNFα drug with the level of the anti-TNFα drug; and (c) determining a subsequent dose of the anti-TNFα drug for the subject based upon the comparison of step (b), thereby optimizing the therapeutic amount of the anti-TNFα drug.

In another embodiment, the present invention provides a method for optimizing therapy and/or reducing toxicity to an anti-TNFα drug in a subject receiving therapy with the anti-TNFα drug, the method comprising:

(a) measuring the level of the anti-TNFα drug in a first sample from the subject;

(b) measuring the level of an autoantibody to the anti-TNFα drug in a second sample from the subject; and (c) determining a subsequent course of therapy for the subject based upon the levels of the anti-TNFα drug and the autoantibody, thereby optimizing therapy and/or reducing toxicity to the anti-TNFα drug.

In another embodiment, the present invention provides a method for determining the presence or level of an anti-TNFα drug with reference to an internal control in a sample having or suspected of having the anti-TNFα drug, the method comprising:

(a) contacting an amount of a labeled TNFα and an amount of a labeled internal control with the sample to form a complex of the labeled TNFα and the anti-TNFα drug;

(b) detecting the labeled TNFα and the labeled internal control by size exclusion chromatography;

(c) integrating the area-under-the curve for a peak of the labeled TNFα from a plot of signal intensity as a function of elution time from the size exclusion chromatography;

(d) integrating the area-under-the curve for a peak of the labeled internal control from the plot of signal intensity as a function of elution time from the size exclusion chromatography;

(e) determining a first ratio by dividing the amount of labeled TNFα by the amount of labeled internal control;

(f) determining a second ratio by dividing the resultant integration from step (c) by the resultant integration from step (d); and (g) comparing the first ratio determined in step (e) with the second ratio determined in step (f), thereby determining the presence or level of the anti-TNFα drug with reference to an internal control.

In another embodiment, the present invention provides a method for optimizing the therapeutic amount of an anti-TNFα drug in a subject receiving therapy with the anti-TNFα drug, the method comprising: determining a subsequent dose of the anti-TNFα drug for the subject based upon a comparison of the ratio of the labeled TNFα to the labeled internal control in step (e) of the previous paragraph with the ratio of the labeled TNFα to the labeled internal control of step (f) in the previous paragraph, thereby optimizing the therapeutic amount of the anti-TNFα drug.

In some embodiments, the present invention provide a method for determining the presence or level of an autoantibody to an anti-TNFα drug with reference to an internal control in a sample having or suspected of having the autoantibody, the method comprising:

(a) contacting an amount of labeled anti-TNFα drug and an amount of labeled internal control with the sample to form a complex of the labeled anti-TNFα drug and the autoantibody;

(b) detecting the labeled anti-TNFα and the labeled internal control by size exclusion chromatography;

(c) integrating the area-under-the curve for a peak of the labeled anti-TNFα drug from a plot of signal intensity as a function of elution time from the size exclusion chromatography;

(d) integrating the area-under-the curve for a peak of the labeled internal control from the plot of signal intensity as a function of elution time from the size exclusion chromatography;

(e) determining a first ratio by dividing the amount of labeled anti-TNFα drug by the amount of labeled internal control; and (f) determining a second ratio by dividing the resultant integration from step (c) and (d); and (g) comparing the first ratio determined in step (e) with the second ratio determined in step (f), thereby determining the presence or level of the autoantibody with reference to an internal control.

In another embodiment, the present invention provides a kit for measuring the presence or level of an anti-TNFα drug and the presence or level of an autoantibody to an anti-TNFα drug in a sample, the kit comprising:

(a) a first measuring substrate comprising an amount of a labeled TNFα;

(b) a second measuring substrate comprising an amount of a labeled anti-TNFα;

(c) optionally a third measuring substrate comprising an amount of a labeled TNFα and an amount of a labeled internal control;

(d) optionally a fourth measuring substrate comprising an amount of a labeled anti-TNFα drug and an amount of a labeled internal control;

(e) optionally a means for extracting a sample from a subject; and (f) optionally a pamphlet of instructions for using the kit.

Other objects, features, and advantages of the present invention will be apparent to one of skill in the art from the following detailed description and figures.

BRIEF DESCRIPTION OF THE DRAWINGS

FIG. 7 shows dose response curves of anti-human IgG antibody binding to REMICADE™-Alexa$_{647}$.

FIG. 9 provides a summary of HACA measurements from 20 patient serum samples that were performed using the bridging assay or the mobility shift assay of the present invention.

FIG. 10 provides a summary and comparison of current methods for measuring serum concentrations of HACA to the novel HACA assay of the present invention.

FIG. 17 shows exemplary embodiments of the assays of the present invention to detect the presence of (A) non-neutralizing or (B) neutralizing autoantibodies such as HACA.

DETAILED DESCRIPTION OF THE INVENTION

I. Introduction

Figure 1:
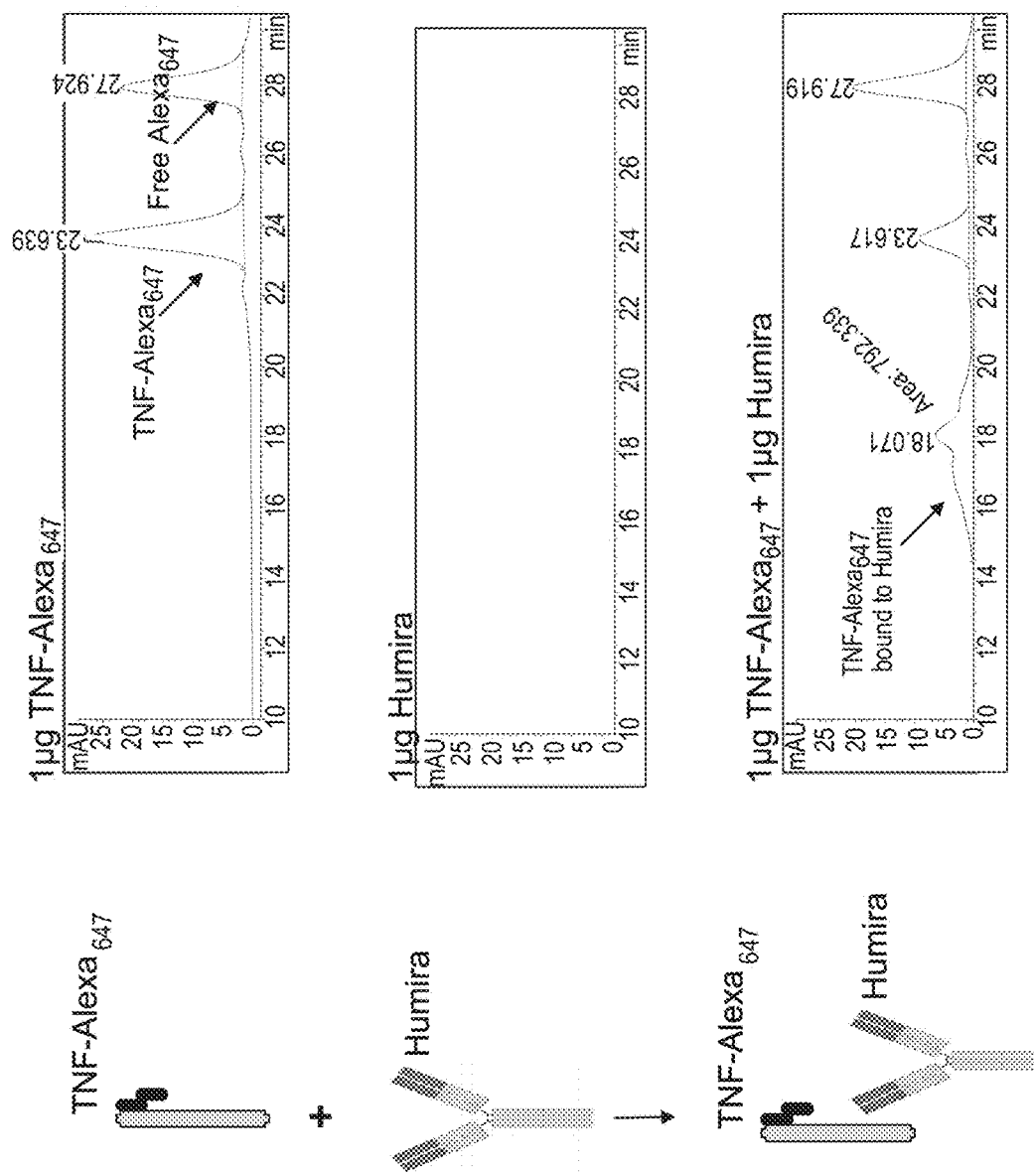
FIG. 1 shows an exemplary embodiment of the assays of the present invention wherein size exclusion HPLC is used to detect the binding between TNFα-Alexa$_{647}$ and HUMIRA™.

The present invention is based in part on the discovery that a homogeneous mobility shift assay using size exclusion chromatography is particularly advantageous for measuring the presence or level of TNFα inhibitors as well as autoantibodies (e.g., HACA, HAHA, etc.) that are generated against them. In particular, the present invention provides "mix and read" assays that do not require any wash steps. As a result, complexed and uncomplexed protein therapeutics are easily separated from each other. In addition, any potential interference from the free drug is minimized using the assays of the present invention. In contrast, a typical ELISA for measuring HACA or HAHA levels cannot be performed until the TNFα inhibitor is eliminated from the body, which can take up to 3 months. Moreover, the present invention is generally applicable to a wide variety of protein therapeutics in addition to anti-TNFα antibodies. The assays of the present invention are also advantageous because they avoid the attachment of antigens to solid surfaces, eliminate the non-specific binding of irrelevant IgGs, detect antibodies with weak affinities, and exhibit increased sensitivity and specificity over currently available detection methods such as enzyme immunoassays.

The importance of measuring serum concentrations of anti-TNFα biologics as well as other immunotherapeutics is illustrated by the fact that the FDA requires pharmacokinetic and tolerability (e.g., immune response) studies to be performed during clinical trials. The present invention also finds utility in monitoring patients receiving these drugs to make sure they are getting the right dose, that the drug isn't being cleared from the body too quickly, and that they are not developing an immune response against the drug. Furthermore, the present invention is useful in guiding the switch between different drugs due to failure with the initial drug.

II. Definitions

As used herein, the following terms have the meanings ascribed to them unless specified otherwise.

The terms "anti-TNFα drug" or "TNF α inhibitor" as used herein is intended to encompass agents including proteins, antibodies, antibody fragments, fusion proteins (e.g., Ig fusion proteins or Fc fusion proteins), multivalent binding proteins (e.g., DVD Ig), small molecule TNF α antagonists and similar naturally- or nonnaturally-occurring molecules, and/or recombinant and/or engineered forms thereof, that, directly or indirectly, inhibit TNF α activity, such as by inhibiting interaction of TNF α with a cell surface receptor for TNF α, inhibiting TNF α protein production, inhibiting TNF α gene expression, inhibiting TNF α secretion from cells, inhibiting TNF α receptor signaling or any other means resulting in decreased TNF α activity in a subject. The term "anti-TNFα drug" or "TNF α inhibitor" preferably includes agents which interfere with TNF α activity. Examples of TNF α inhibitors include etanercept (ENBREL™, Amgen), infliximab (REMICADE™, Johnson and Johnson), human anti-TNF monoclonal antibody adalimumab (D2E7/HUMIRA™, Abbott Laboratories), certolizumab pegol (CIMZIA®, UCB, Inc.), CDP 571 (Celltech), and CDP 870 (Celltech), as well as other compounds which inhibit TNF α activity, such that when administered to a subject suffering from or at risk of suffering from a disorder in which TNF α activity is detrimental (e.g., RA), the disorder is treated.

The term "predicting responsiveness to a TNF α inhibitor", as used herein, is intended to refer to an ability to assess the likelihood that treatment of a subject with a TNF α inhibitor will or will not be effective in (e.g., provide a measurable benefit to) the subject. In particular, such an ability to assess the likelihood that treatment will or will not be effective typically is exercised after treatment has begun, and an indicator of effectiveness (e.g., an indicator of measurable benefit) has been observed in the subject. Particularly preferred TNFα inhibitors are biologic agents that have been approved by the FDA for use in humans in the treatment of TNFα-mediated diseases or disorders such as, e.g., rheumatoid arthritis, or inflammatory bowel disease (IBD), which agents include adalimumab (HUMIRA™), infliximab (REMICADE™) etanercept (ENBREL™), and certolizumab pegol (CIMZIA®, UCB, Inc.).

The term "size exclusion chromatography" (SEC) is intended to include a chromatographic method in which molecules in solution are separated based on their size and/or hydrodynamic volume. It is applied to large molecules or macromolecular complexes such as proteins and their conjugates. Typically, when an aqueous solution is used to transport the sample through the column, the technique is known as gel filtration chromatography.

The terms "complex," "immuno-complex," "conjugate," and "immunoconjugate" include, but are not limited to, TNFα bound (e.g., by non-covalent means) to an anti-TNFα drug, an anti-TNFα drug bound (e.g., by non-covalent means) to an autoantibody against the anti-TNFα drug, and an anti-TNFα drug bound (e.g., by non-covalent means) to both TNFα and an autoantibody against the anti-TNFα drug.

As used herein, an entity that is modified by the term "labeled" includes any entity, molecule, protein, enzyme, antibody, antibody fragment, cytokine, or related specie that is conjugated with another molecule or chemical entity that is empirically detectable. Chemical species suitable as labels for labeled-entities include, but are not limited to, fluorescent dyes, e.g. Alexa Fluor® dyes such as Alexa Fluor® 647, quantum dots, optical dyes, luminescent dyes, and radionuclides, e.g. $^{125}$I.

The term "effective amount" includes a dose of a drug that is capable of achieving a therapeutic effect in a subject in need thereof as well as the bioavailable amount of a substance. The term "bioavailable" includes the fraction of an administered dose of a drug that is available for therapeutic activity. For example, an effective amount of a drug useful for treating diseases and disorders in which TNF-α has been implicated in the pathophysiology, e.g., but not limited to, shock, sepsis, infections, autoimmune diseases, RA, Crohn's disease, transplant rejection and graft-versus-host disease, can be the amount that is capable of preventing or relieving one or more symptoms associated therewith.

The phrase "area-under-the-curve" is a mathematical term of art used to describe an integration of a portion of a two dimensional plot. For example, in a plot of signal intensity as a function of elution time from a size exclusion chromatography, various peaks in the plot indicate the detection of particular molecules. The integration of these peaks includes the area circumscribed by a minimum y-axis value, e.g. the baseline of the two dimensional plot, and circumscribed by the two dimensional plot itself. The integration of a peak is also equally described by the calculus formula, Area-under-the-curve=$\int_a^b f(x)dx$, where f(x) is a function describing the two dimensional plot and variables "a" and "b" indicate the x-axis limits of the integrated peak.

The phrase "fluorescence label detection" includes a means for detecting a fluorescent label. Means for detection include, but are not limited to, a spectrometer, a fluorimeter, a photometer, a detection device commonly incorporated with a chromatography instrument such as, but not limited to, a size exclusion-high performance liquid chromatography, such as, but not limited to, an Agilent-1200 HPLC System.

Brackets, "[ ]" indicate that the species within the brackets are referred to by their concentration.

The phrase "optimize therapy" includes optimizing the dose (e.g., the effective amount or level) and/or the type of a particular therapy. For example, optimizing the dose of an anti-TNFα drug includes increasing or decreasing the amount of the anti-TNFα drug subsequently administered to a subject. In certain instances, optimizing the type of an anti-TNFα drug includes changing the administered anti-TNFα drug from one drug to a different drug (e.g., a different anti-TNFα drug). In certain other instances, optimizing therapy include co-administering a dose of an anti-TNFα drug (e.g., at an increased, decreased, or same dose as the previous dose) in combination with an immunosuppressive drug.

The term "co-administer" includes to administer more than one active agent, such that the duration of physiological effect of one active agent overlaps with the physiological effect of a second active agent.

The term "subject," "patient," or "individual" typically refers to humans, but also to other animals including, e.g., other primates, rodents, canines, felines, equines, ovines, porcines, and the like.

The term "course of therapy" includes any therapeutic approach taken to relieve or prevent one or more symptoms associated with a TNFα-mediated disease or disorder. The term encompasses administering any compound, drug, procedure, and/or regimen useful for improving the health of an individual with a TNFα-mediated disease or disorder and includes any of the therapeutic agents described herein. One skilled in the art will appreciate that either the course of therapy or the dose of the current course of therapy can be changed (e.g., increased or decreased) based upon the presence or concentration level of an anti-TNFα drug and/or an autoantibody to the anti-TNFα drug.

The term "immunosuppressive drug" or "immunosuppressive agent" includes any substance capable of producing an immunosuppressive effect, e.g., the prevention or diminution of the immune response, as by irradiation or by administration of drugs such as anti-metabolites, anti-lymphocyte sera, antibodies, etc. Examples of suitable immunosuppressive drugs include, without limitation, thiopurine drugs such as azathioprine (AZA) and metabolites thereof; anti-metabolites such as methotrexate (MTX); sirolimus (rapamycin); temsirolimus; everolimus; tacrolimus (FK-506); FK-778; anti-lymphocyte globulin antibodies, anti-thymocyte globulin antibodies, anti-CD3 antibodies, anti-CD4 antibodies, and antibody-toxin conjugates; cyclosporine; mycophenolate; mizoribine monophosphate; scoparone; glatiramer acetate; metabolites thereof; pharmaceutically acceptable salts thereof; derivatives thereof; prodrugs thereof; and combinations thereof.

The term "thiopurine drug" includes azathioprine (AZA), 6-mercaptopurine (6-MP), or any metabolite thereof that has therapeutic efficacy and includes, without limitation, 6-thioguanine (6-TG), 6-methylmercaptopurine riboside, 6-thioinosine nucleotides (e.g., 6-thioinosine monophosphate, 6-thioinosine diphosphate, 6-thioinosine triphosphate), 6-thioguanine nucleotides (e.g., 6-thioguanosine monophosphate, 6-thioguanosine diphosphate, 6-thioguanosine triphosphate), 6-thioxanthosine nucleotides (e.g., 6-thioxanthosine monophosphate, 6-thioxanthosine diphosphate, 6-thioxanthosine triphosphate), derivatives thereof, analogues thereof, and combinations thereof.

The term "sample" includes any biological specimen obtained from an individual. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). In a preferred embodiment, the sample is a serum sample. One skilled in the art will appreciate that samples such as serum samples can be diluted prior to the analysis. In certain instances, the term "sample" includes, but is not limited to blood, body tissue, blood serum, lymph fluid, lymph node tissue, spleen tissue, bone marrow, or an immunoglobulin enriched fraction derived from one or more of these tissues. In certain other instances, the term "sample" includes blood serum or is an immunoglobulin enriched fraction derived from blood serum or blood. In certain instances, the term "sample" includes a bodily fluid.

III. Description of the Embodiments

The steps of the methods of the present invention do not necessarily have to be performed in the particular order in which they are presented. A person of ordinary skill in the art would understand that other orderings of the steps of the methods of the present invention are encompassed within the scope of the present invention.

In one embodiment, the present invention provides a method for detecting the presence or level of an anti-TNFα drug in a sample, comprising:

(a) contacting labeled TNFα with a sample having or suspected of having an anti-TNFα drug to form a labeled complex with the anti-TNFα drug;

(b) subjecting the labeled complex to size exclusion chromatography to separate the labeled complex; and (c) detecting the labeled complex, thereby detecting the anti-TNFα drug.

In certain instances, the methods are especially useful for the following anti-TNFα antibodies: REMICADE™ (infliximab), ENBREL™ (etanercept), HUMIRA™ (adalimumab), and CIMZIA® (certolizumab pegol).

Tumor necrosis factor α (TNFα) is a cytokine involved in systemic inflammation and is a member of a group of cytokines that stimulate the acute phase reaction. The primary role of TNFα is in the regulation of immune cells. TNFα is also able to induce apoptotic cell death, to induce inflammation, and to inhibit tumorigenesis and viral replication. TNF is primarily produced as a 212-amino acid-long type II transmembrane protein arranged in stable homotrimers.

The term "TNF-α," as used herein, is intended to include a human cytokine that exists as a 17 kDa secreted form and a 26 kDa membrane associated form, the biologically active form of which is composed of a trimer of noncovalently bound 17 kDa molecules. The structure of TNF-α is described further in, for example, Jones, et al. (1989) Nature, 338:225-228. The term TNF-α is intended to include human, a recombinant human TNF-α (rhTNF-α), or at least about 80% identity to the human TNFα protein. Human TNFα consists of a 35 amino acid (aa) cytoplasmic domain, a 21 aa transmembrane segment, and a 177 aa extracellular domain (ECD) (Pennica, D. et al. (1984) Nature 312:724). Within the ECD, human TNFα shares 97% aa sequence identity with rhesus and 71% 92% with bovine, canine, cotton rat, equine, feline, mouse, porcine, and rat TNFα. TNFα can be prepared by standard recombinant expression methods or purchased commercially (R & D Systems, Catalog No. 210-TA, Minneapolis, Minn.).

In certain embodiments, "TNF-α" is an "antigen," which is a molecule or a portion of the molecule capable of being bound by an anti-TNF-α antibody. TNF-α can have one or more than one epitope. In certain instances, TNF-α will react, in a highly selective manner, with an anti-TNF-α antibody. Preferred antigens that bind antibodies, fragments and regions of anti-TNF antibodies of the present invention include at least 5 amino acids of SEQ ID NO: 1. In certain instances, TNF-α is a sufficient length having an epitope of TNF α that is capable of binding anti-TNF-α antibodies, fragments and regions thereof.

In certain embodiments, the length of TNF-α having an epitope of sufficient length to bind an anti-TNF-α antibody, fragments and regions thereof is at least 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220 amino acids in length. In one embodiment, the TNF-α used includes residues 77-233 of SEQ ID NO: 1.

In certain instances, at least one amino acid in the soluble portion of TNF-α is labeled i.e., residues 77-233 of SEQ ID NO:1. In certain instances, an amine reactive fluorophore derivative is used. In most instances, the amine reactive group is an acylating reagent that forms carboxamides, sulfonamides or thioureas upon reaction with amines. Virtually all proteins have lysine residues, and most have a free amine at the N-terminus and thus can be used as a point of attachment to label. In a preferred embodiment, residue 77 is labeled, and the TNF-α used includes residues 77-233 of SEQ ID NO: 1. In other embodiments, many primary amines are labeled and the TNF-α is multiply labeled.

In certain instances, a portion of TNF-α is not labeled, i.e., portions that are recognized by antibodies, and fragments and regions thereof. In other words, certain portions of TNF-α antigens provide a topographical or three dimensional epitope of TNF which is recognized by, and/or binds with anti-TNF activity, an antibody, and fragments, and variable regions thereof. These portions are preferably free to bind, and thus are not labeled. They include residues 136-157 and 164-185 of SEQ ID NO: 1:

```
                                           (SEQ ID NO: 2)
Tyr-Ser-Gln-Val-Leu-Phe-Lys-Gly-Gln-Gly-Cys-Pro-
Ser-Thr-His-Val-Leu-Leu-Thr-His-Thr-Ile;
and
                                           (SEQ ID NO: 3)
Tyr-Gln-Thr-Lys-Val-Asn-Leu-Leu-Ser-Ala-Ile-Lys-
Ser-Pro-Cys-Gln-Arg-Glu-Thr-Pro-Glu-Gly.
```

TNFα or an anti-TNFα drug can be labeled with a variety of detectable group(s). Preferably, TNFα or an anti-TNFα drug is labeled with a fluorophore or a fluorescent dye. Exemplary fluorophores suitable for use in the present invention include those listed in the Molecular Probes Catalogue, which is herein incorporated by reference (see, R. Haugland, *The Handbook—A Guide to Fluorescent Probes and Labeling Technologies*, 10$^{th}$ Edition, Molecular probes, Inc. (2005)). Such exemplary fluorophores include, but are not limited to, Alexa Fluor® dyes such as Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, and/or Alexa Fluor® 790, as well as other fluorophores such as, for example, Dansyl Chloride (DNS-Cl), 5-(iodoacetamida) fluoroscein (5-IAF), fluoroscein 5-isothiocyanate (FITC), tetramethylrhodamine 5- (and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids (e.g., 1-anilinonaphthalene-8-sulfonic acid (ANS), 6-(p-toluidinyl)naphthalene-2-sulfonic acid (TNS), and the like), Anthroyl fatty acid, DPH, Parinaric acid, TMA-DPH, Fluorenyl fatty acid, fluorescein-phosphatidylethanolamine, Texas Red-phosphatidylethanolamine, Pyrenyl-phophatidylcholine, Fluorenyl-phosphotidylcholine, Merocyanine 540,1-(3-sulfonatopropyl)-4-[β-[2[(di-n-butylamino)-6 naphthyl]vinyl]pyridinium betaine (Naphtyl Styryl), 3,3'dipropylthiadicarbocyanine (diS-C$_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1, 4', 6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, metal-ligand complexes, IRDye® 700DX, IRDye® 700, IRDye® 800RS, IRDye® 800CW, IRDye® 800, Cy5, Cy5.5, Cy7, DY 676, DY680, DY682, DY780, and mixtures thereof. Additional suitable fluorophores include enzyme-cofactors; lanthanide, green fluorescent protein, yellow fluorescent protein, red fluorescent protein, or mutants and derivates thereof. In one embodiment of the invention, the second member of the specific binding pair has a detectable group attached thereto.

Typically, the fluorescent group is a fluorophore selected from the category of dyes comprising polymethines, pthalocyanines, cyanines, xanthenes, fluorenes, rhodamines, coumarins, fluoresceins and BODIPY™.

In one embodiment, the fluorescent group is a near-infrared (NIR) fluorophore that emits in the range of between about 650 to about 900 nm. Use of near infrared fluorescence technology is advantageous in biological assays as it substantially eliminates or reduces background from auto fluorescence of biosubstrates. Another benefit to the near-IR fluorescent technology is that the scattered light from the excitation source is greatly reduced since the scattering intensity is proportional to the inverse fourth power of the wavelength.

Low background fluorescence and low scattering result in a high signal to noise ratio, which is essential for highly sensitive detection. Furthermore, the optically transparent window in the near-IR region (650 nm to 900 nm) in biological tissue makes NIR fluorescence a valuable technology for in vivo imaging and subcellular detection applications that require the transmission of light through biological components. Within aspects of this embodiment, the fluorescent group is preferably selected form the group consisting of IRDye® 700DX, IRDye® 700, IRDye® 800RS, IRDye® 800CW, IRDye® 800, Alexa Fluor® 660, Alexa Fluor® 680, Alexa Fluor® 700, Alexa Fluor® 750, Alexa Fluor® 790, Cy5, Cy5.5, Cy7, DY 676, DY680, DY682 and DY780. In certain embodiments, the near infrared group is IRDye® 800CW, IRDye® 800, IRDye® 700DX, IRDye® 700, or Dynomic DY676.

Fluorescent labeling is accomplished using a chemically reactive derivative of a fluorophore. Common reactive groups include amine reactive isothiocyanate derivatives such as FITC and TRITC (derivatives of fluorescein and rhodamine), amine reactive succinimidyl esters such as NHS-fluorescein, and sulfhydryl reactive maleimide activated fluors such as fluorescein-5-maleimide, many of which are commercially available. Reaction of any of these reactive dyes with TNFα or an anti-TNFα drug results in a stable covalent bond formed between a fluorophore and TNFα or an anti-TNFα drug.

In certain instances, following a fluorescent labeling reaction, it is often necessary to remove any nonreacted fluorophore from the labeled target molecule. This is often accomplished by size exclusion chromatography, taking advantage of the size difference between fluorophore and labeled protein.

Reactive fluorescent dyes are available from many sources. They can be obtained with different reactive groups for attachment to various functional groups within the target molecule. They are also available in labeling kits that contain all the components to carry out a labeling reaction. In one preferred aspect, Alexa Fluor® 647 C2 maleimide is used from Invitrogen (Cat. No. A-20347).

Specific immunological binding of an anti-TNFα antibody to TNFα or of an anti-drug antibody (ADA) to an anti-TNFα antibody can be detected directly or indirectly. Direct labels include fluorescent or luminescent tags, metals, dyes, radionuclides, and the like, attached to the antibody. In certain instances, TNFα or an anti-TNFα antibody labeled with iodine-125 ($^{125}$I) can be used for determining the concentration levels of anti-TNFα antibody or ADA in a sample, respectively. In other instances, a chemiluminescence assay using a chemiluminescent TNFα or anti-TNFα antibody specific for anti-TNFα antibody or ADA in a sample, respectively, is suitable for sensitive, non-radioactive detection of anti-TNFα antibody or ADA concentration levels. In particular instances, TNFα or an anti-TNFα antibody labeled with a fluorochrome is also suitable for determining the concentration levels of anti-TNFα antibody or ADA in a sample, respectively. Examples of fluorochromes include, without limitation, Alexa Fluor® dyes, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of anti-TNFα antibody or ADA levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

In certain embodiments, size exclusion chromatography is used. The underlying principle of SEC is that particles of different sizes will elute (filter) through a stationary phase at different rates. This results in the separation of a solution of particles based on size. Provided that all the particles are loaded simultaneously or near simultaneously, particles of the same size elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

In certain aspects, the eluent is collected in constant volumes, or fractions. The more similar the particles are in size, the more likely they will be in the same fraction and not detected separately. Preferably, the collected fractions are examined by spectroscopic techniques to determine the concentration of the particles eluted. Typically, the spectroscopy detection techniques useful in the present invention include, but are not limited to, fluorometry, refractive index (RI), and ultraviolet (UV). In certain instances, the elution volume decreases roughly linearly with the logarithm of the molecular hydrodynamic volume (i.e., heaver moieties come off first).

In certain aspects, the methods are useful in detecting the amount of anti-TNFα drugs such as, e.g., antibodies including REMICADE™ (infliximab), a chimeric anti-TNFα mAb, ENBREL™ (etanercept), a TNFR-Ig Fc fusion protein, HUMIRA™ (adalimumab), a human anti-TNFα mAb, and CIMZIA® (certolizumab pegol), a PEGylated Fab fragment.

In certain instances, after the anti-TNFα drug (e.g., anti-TNFα antibody) is detected, the anti-TNF α drug is measured using a standard curve.

In another embodiment, the present invention provides a method for detecting the presence or level of an autoantibody to an anti-TNFα drug in a sample, the method comprising:

(a) contacting labeled anti-TNFα drug with the sample to form a labeled complex with the autoantibody;

(b) subjecting the labeled complex to size exclusion chromatography to separate the labeled complex; and (c) detecting the presence or level labeled complex, thereby detecting the autoantibody.

In certain instances, the autoantibodies include human anti-chimeric antibodies (HACA), human anti-humanized antibodies (HAHA), and human anti-mouse antibodies (HAMA).

In yet another embodiment, the present invention provides a method for detecting the presence or level of an autoantibody to an anti-TNFα drug in a sample, comprising:

(a) contacting a labeled anti-TNFα drug and labeled TNFα with a sample having or suspected of having an autoantibody to the anti-TNFα drug to form a first labeled complex between the labeled anti-TNFα drug, the labeled TNFα, and the autoantibody and a second labeled complex between the labeled anti-TNFα drug and the autoantibody, wherein the labeled anti-TNFα drug and the labeled TNFα comprise different labels;

(b) subjecting the first labeled complex and the second labeled complex to size exclusion chromatography to separate the first labeled complex and the second labeled complex; and (c) detecting the first labeled complex and the second labeled complex, thereby detecting a non-neutralizing form of the autoantibody when both the first labeled complex and the second labeled complex are present, and detecting a neutralizing form of the autoantibody when only the second labeled complex is present.

In certain instances, the autoantibodies include human anti-chimeric antibodies (HACA), human anti-humanized antibodies (HAHA), and human anti-mouse antibodies (HAMA).

In a related embodiment, the present invention provides a method for detecting the presence or level of an autoantibody to an anti-TNFα drug in a sample, comprising:

(a) contacting a labeled anti-TNFα drug with a sample having or suspected of having an autoantibody to the anti-TNFα drug to form a first labeled complex between the labeled anti-TNFα drug and the autoantibody;

(b) subjecting the first labeled complex to a first size exclusion chromatography to separate the first labeled complex;

(c) detecting the first labeled complex, thereby detecting the presence or level of the autoantibody;

(d) contacting labeled TNFα with the first labeled complex to form a second labeled complex between the labeled anti-TNFα drug and the labeled TNFα, wherein the labeled anti-TNFα drug and the labeled TNFα comprise different labels;

(e) subjecting the second labeled complex to a second size exclusion chromatography to separate the second labeled complex; and (f) detecting the second labeled complex, thereby detecting the presence or level of a neutralizing form of the autoantibody.

In certain instances, the autoantibodies include human anti-chimeric antibodies (HACA), human anti-humanized antibodies (HAHA), and human anti-mouse antibodies (HAMA).

In other embodiments, the assay methods described herein can be used to predict responsiveness to a TNF α inhibitor, especially to an anti-TNF α antibody in a subject having an autoimmune disorder (e.g., rheumatoid arthritis, Crohn's Disease, and the like.). In this method, by assaying the subject for the correct or therapeutic dose of anti-TNF α antibody, i.e., the therapeutic concentration level, it is possible to predict whether the individual will be responsive to the therapy.

In another embodiment, the present invention provides methods for monitoring an autoimmune disorder in a subject having the autoimmune disorder, wherein the method comprises assaying the subject for the correct or therapeutic dose of anti-TNF α antibody, i.e., the therapeutic concentration level, over time. In this manner, it is possible to predict whether the individual will be responsive to the therapy over the given time period.

In another embodiment, the present invention provides a method for determining an effective amount of an anti-TNFα drug for a subject receiving therapy with the anti-TNFα drug, the method comprising:
  (a) measuring the level of the anti-TNFα drug in a first sample from the subject, comprising:
    (i) contacting the first sample with an amount of a labeled TNFα to form a first complex comprising the labeled TNFα with the anti-TNFα drug; and
    (ii) detecting the first complex by size exclusion chromatography,
  thereby measuring the level of the anti-TNFα drug;
  (b) measuring the level of an autoantibody to the anti-TNFα drug in a second sample from the subject, comprising:
    (i) contacting the second sample with an amount of a labeled anti-TNFα drug to form a second complex comprising the labeled anti-TNFα drug with the autoantibody; and
    (ii) detecting the second complex by size exclusion chromatography,
  thereby measuring the level of the autoantibody; and
  (c) subtracting the level of the autoantibody measured in step (b) from the level of the anti-TNFα drug measured in step (a),
thereby determining the effective amount of the anti-TNFα drug.

In a related embodiment, the present invention further provides that the detection in step (a)(ii) comprises:
  (1) integrating the area-under-the curve for a peak of the labeled TNFα from a first plot of signal intensity as a function of elution time from the size exclusion chromatography;
  (2) integrating the area-under-the curve for a peak of the first complex from the first plot;
  (3) determining a ratio by dividing the resultant integration from step (2) by the resultant integration from step (1); and
  (4) multiplying the amount of the labeled TNFα by the ratio of step (3).

In a related embodiment, the present invention further provides that the detection in step (b)(ii) comprises:
  (1) integrating the area-under-the curve for a peak of the labeled anti-TNFα drug from a second plot of signal intensity as a function of elution time from the size exclusion chromatography;
  (2) integrating the area-under-the curve for a peak of the second complex from the second plot;
  (3) determining a ratio by dividing the resultant integration from step (2) by the resultant integration from step (1); and
  (4) multiplying the amount of the labeled anti-TNFα drug by the ratio of step (3).

In a related embodiment, the present invention further provides that both the first and second samples are serum samples. In another related embodiment, the present invention further provides that both the first and second samples are obtained from the subject during therapy with the anti-TNFα drug. In yet another related embodiment, the present invention further provides that the detection in step (a)(ii) and/or step (b)(ii) comprises fluorescence label detection.

In another embodiment, the present invention provides a method for optimizing the therapeutic amount of an anti-TNFα drug in a subject receiving therapy with the anti-TNFα drug, the method comprising:
  (a) determining an effective amount of the anti-TNFα drug in accordance with the methods of the present invention;
  (b) comparing the effective amount of the anti-TNFα drug with the level of the anti-TNFα drug; and
  (c) determining a subsequent dose of the anti-TNFα drug for the subject based upon the comparison of step (c),
thereby optimizing the therapeutic amount of the anti-TNFα drug.

In a related embodiment, the present invention further provides increasing the subsequent dose of the anti-TNFα drug when the effective amount of the anti-TNFα drug is less than the level of the anti-TNFα drug. In a related embodiment, the present invention provides that the subsequent dose of the anti-TNFα drug is increased such that the effective amount of the anti-TNFα drug is about equal to the level of the anti-TNFα drug.

In some other embodiments, the present invention further provides that the anti-TNFα drug is a member selected from the group consisting of REMICADE™ (infliximab), ENBREL™ (etanercept), HUMIRA™ (adalimumab), CIMZIA® (certolizumab pegol), and combinations thereof.

In some embodiments, the anti-TNFα drug is infliximab (REMICADE™). In some other embodiments, the anti-TNFα drug is adalimumab (HUMIRA™). In other embodiments, the anti-TNFα drug is etanercept (ENBREL™). In some other embodiments, the anti-TNFα drug is CIMZIA® (certolizumab pegol). In other embodiments, the labeled TNFα is a fluorophore labeled TNFα. In some other embodiments, the measured anti-TNFα drug is quantitated.

In some embodiments, the measured TNFα is quantitated. In other embodiments, the labeled complex is eluted first, followed by free labeled TNFα. In some other embodiments, the labeled complex is eluted first, followed by free labeled anti-TNFα antibody. In some embodiments, the size exclusion chromatography is size exclusion-high performance liquid chromatography (SE-HPLC). In some other embodiments, the autoantibody is a member selected from human anti-mouse antibody (HAMA), human anti-chimeric antibody (HACA), human anti-humanized antibody (HAHA), or combinations thereof. In some embodiments, the measured autoantibody is quantitated.

In another embodiment, the present invention provides a method for optimizing therapy and/or reducing toxicity to an anti-TNFα drug in a subject receiving therapy with the anti-TNFα drug, the method comprising:
(a) measuring the level of the anti-TNFα drug in a first sample from the subject;
(b) measuring the level of an autoantibody to the anti-TNFα drug in a second sample from the subject; and
(c) determining a subsequent course of therapy for the subject based upon the levels of the anti-TNFα drug and the autoantibody,
thereby optimizing therapy and/or reducing toxicity to the anti-TNFα drug.

In a related embodiment, the subsequent course of therapy comprises co-administering an immunosuppressive drug with the anti-TNFα drug when the level of the anti-TNFα drug is a high level and the level of the autoantibody is a low level. In another related embodiment, the subsequent course of therapy comprises increasing the level of the anti-TNFα drug and co-administering an immunosuppressive drug when the level of the anti-TNFα drug is a medium level and the level of the autoantibody is a low level. In another related embodiment, the subsequent course of therapy comprises administering a different anti-TNFα drug when the level of the anti-TNFα drug is a medium level and the level of the autoantibody is a medium level. In yet another related embodiment, the subsequent course of therapy comprises administering a different anti-TNFα drug when the level of the anti-TNFα drug is a low level and the level of the autoantibody is a high level. In another related embodiment, adalimumab (HUMIRA™) is administered instead of infliximab (REMICADE™).

In some embodiments, the phrase "high level of an anti-TNFα drug" includes drug levels of about 10 to about 100 ng/10 µL, about 10 to about 70 ng/10 µL, or about 10 to about 50 ng/10 µL. In other embodiments, the phrase "high level of anti-TNFα drug" includes drug levels greater than about 10, 20, 30, 40, 50, 60, 70, 80, 90, or 100 ng/10 µL.

In some embodiments, the phrase "medium level of an anti-TNFα drug" includes drug levels of about 5.0 to about 50 ng/10 µL, about 5.0 to about 30 ng/10 µL, about 5.0 to about 20 ng/10 µL, or about 5.0 to about 10 ng/10 µL. In other embodiments, the phrase "medium level of anti-TNFα drug" includes drug levels of about 10, 9, 8, 7, 6, 5, 4, 3, 2, or 1 ng/10 µL.

In some embodiments, the phrase "low level of an anti-TNFα drug" includes drug levels of about 0 to about 10 ng/10 µL, about 0 to about 8 ng/10 µL, or about 0 to about 5 ng/10 µL. In other embodiments, the phrase "low level of an anti-TNFα drug" includes drug levels of about less than about 10, 9.0, 8.0, 7.0, 6.0, 5.0, 4.0, 3.0, 2.0, 1.0, or 0.5 ng/10 µl The acronym "ADA" includes the phrase "anti-drug antibody."

In some embodiments, the phrase "high level of an anti-drug antibody" includes anti-drug antibody levels of about 3.0 to about 100 ng/10 µL, about 3.0 to about 50 ng/10 µL, about 10 to about 100 ng/10 µL, about 10 to about 50 ng/10 µL, or about 20 to about 50 ng/10 µL. In some other embodiments, the phrase "high level of anti-drug antibody" includes anti-drug antibody levels of about greater than about 10, 20, 30, 40, 50, 60, 70, 80, 90, or 100 ng/10 µl.

In some embodiments, the phrase "medium level of an anti-drug antibody" includes anti-drug antibody levels of about 0.5 to about 20 ng/10 al, about 0.5 to about 10 ng/10 al, about 2.0 to about 20 ng/10 µL, about 2.0 to about 10 ng/10 µL, about 2.0 to about 5.0 ng/10 µL, or about 2.0 to about 5.0 ng/10 µl.

In some embodiments, the phrase "low level of an anti-drug antibody" includes anti-drug antibody levels of about 0.0 to about 5.0 ng/10 µl, about 0.1 to about 5.0 ng/10 µl, about 0.0 to about 2.0 ng/10 µl, about 0.1 to about 2.0 ng/10 µl, or about 0.5 to about 2.0 ng/10 µl. In other embodiments, the phrase "low level of anti-drug antibody" includes anti-drug antibody levels of about less than about 5.0, 4.0, 3.0, 2.0, 1.0, or 0.5 ng/10 µl.

In some embodiments, the methods of the present invention further provide that anti-TNFα drug is measured with an assay comprising:
(i) contacting the first sample with an amount of a labeled TNFα to form a first complex comprising the labeled TNFα with the anti-TNFα drug; and
(ii) detecting the first complex by size exclusion chromatography,
thereby measuring the level of the anti-TNFα drug.

In some embodiments, the methods of the present invention further provide that the autoantibody is measured with an assay comprising:
(i) contacting the second sample with an amount of a labeled anti-TNFα drug to form a second complex comprising the labeled anti-TNFα drug with the autoantibody; and
(ii) detecting the second complex by size exclusion chromatography,
thereby measuring the level of the autoantibody.

In a related embodiment, the methods of the present invention further provide that the anti-TNFα drug is a member selected from the group consisting of REMICADE™ (infliximab), ENBREL™ (etanercept), HUMIRA™ (adalimumab), CIMZIA® (certolizumab pegol), and combinations thereof. In a related embodiment, the methods of the present invention further provide that the anti-TNFα drug is infliximab (REMICADE™). In some other embodiments, the anti-TNFα drug is adalimumab (HUMIRA™). In some other embodiments, the anti-TNFα drug is etanercept (ENBREL™). In another related embodiment, the methods of the present invention further provide that the anti-TNFα drug is CIMZIA® (certolizumab pegol). In another related embodiment, the methods of the present invention further provide that the measured anti-TNFα drug is quantitated. In another related embodiment, the methods of the present invention further provide that both the first and second samples are serum. In another related embodiment, the methods of the present invention further provide that both the first and second samples are obtained from the subject during therapy with the anti-TNFα drug. In another related embodiment, the methods of the present invention further provide that the autoantibody is a member selected from human anti-mouse antibody (HAMA), human anti-chimeric antibody (HACA), human anti-humanized antibody (HAHA), or combinations thereof. In another related embodiment, the methods of the present invention further provide that the measured autoantibody is quantitated.

In some embodiments, the present invention provides a method for determining the presence or level of an anti-TNFα drug with reference to an internal control in a sample having or suspected of having the anti-TNFα drug, the method comprising:
(a) contacting an amount of a labeled TNFα and an amount of a labeled internal control with the sample to form a complex of the labeled TNFα and the anti-TNFα drug;
(b) detecting the labeled TNFα and the labeled internal control by size exclusion chromatography;
(c) integrating the area-under-the curve for a peak of the labeled TNFα from a plot of signal intensity as a function of elution time from the size exclusion chromatography;
(d) integrating the area-under-the curve for a peak of the labeled internal control from the plot of signal intensity as a function of elution time from the size exclusion chromatography;
(e) determining a first ratio by dividing the amount of labeled TNFα by the amount of labeled internal control;
(f) determining a second ratio by dividing the resultant integration from step (c) by the resultant integration from step (d); and
(g) comparing the first ratio determined in step (e) with the second ratio determined in step (f), thereby determining the presence or level of the anti-TNFα drug with reference to an internal control.

In a related embodiment, the present invention further provides that the first ratio determined in step (e) is from about 80:1 to about 100:1. In another related embodiment, the present invention further provides that the first ratio determined in step (e) is about 100:1. In a related embodiment, the present invention further provides that the labeled internal control is Biocytin-Alexa 488. In certain embodiments, the amount of the labeled internal control (e.g., Biocytin-Alexa 488) is from about 1 to about 25 ng per 100 µL of sample analyzed. In certain other embodiments, the amount of the labeled internal control (e.g., Biocytin-Alexa 488) is from about 5 to about 25 ng per 100 µL, from about 5 to about 20 ng per 100 µL, from about 1 to about 20 ng per 100 µL, from about 1 to about 10 ng per 100 µL, or from about 1 to about 5 ng per 100 µL of sample analyzed. In further embodiments, the amount of the labeled internal control (e.g., Biocytin-Alexa 488) is about 1, 5, 10, 15, 20, or 25 ng per 100 µL of sample analyzed.

In some embodiments, the present invention provides a method for optimizing the therapeutic amount of an anti-TNFα drug in a subject receiving therapy with the anti-TNFα drug, the method comprising: determining a subsequent dose of the anti-TNFα drug for the subject based upon the comparison of the first and second ratios in accordance with the methods of the present invention, thereby optimizing the therapeutic amount of the anti-TNFα drug. In a related embodiment, the present invention further provides that the method further comprises: increasing the subsequent dose of the anti-TNFα drug when the first ratio is about 100:1 and the second ratio is less than about 95:1, thereby optimizing the therapeutic amount of the anti-TNFα drug. In another related embodiment, the present invention further provides that the anti-TNFα drug is a member selected from the group consisting of REMICADE™ (infliximab), ENBREL™ (etanercept), HUMIRA™ (adalimumab), CIMZIA® (certolizumab pegol), and combinations thereof. In a related embodiment, the present invention further provides that the anti-TNFα drug is infliximab (REMICADE™). In a related embodiment, the present invention further provides that the anti-TNFα drug is adalimumab (HUMIRA™). In a related embodiment, the present invention further provides that the anti-TNFα drug is etanercept (ENBREL™). In a related embodiment, the present invention further provides that the anti-TNFα drug is CIMZIA® (certolizumab pegol). In a related embodiment, the present invention further provides that the labeled TNFα is a fluorophore labeled TNFα. In a related embodiment, the present invention further provides that the detected anti-TNFα drug is quantitated. In a related embodiment, the present invention further provides that the labeled complex is eluted first, followed by free labeled TNFα. In a related embodiment, the present invention further provides that the sample is serum. In a related embodiment, the present invention further provides that the sample is obtained from a subject receiving therapy with the anti-TNFα drug. In a related embodiment, the present invention further provides that the size exclusion chromatography is size exclusion-high performance liquid chromatography (SE-HPLC).

In some embodiments, the present invention provides a method for determining the presence or level of an autoantibody to an anti-TNFα drug with reference to an internal control in a sample having or suspected of having the autoantibody, the method comprising:
(a) contacting an amount of labeled anti-TNFα drug and an amount of labeled internal control with the sample to form a complex of the labeled anti-TNFα drug and the autoantibody;
(b) detecting the labeled anti-TNFα and the labeled internal control by size exclusion chromatography;
(c) integrating the area-under-the curve for a peak of the labeled anti-TNFα drug from a plot of signal intensity as a function of elution time from the size exclusion chromatography;
(d) integrating the area-under-the curve for a peak of the labeled internal control from the plot of signal intensity as a function of elution time from the size exclusion chromatography;
(e) determining a first ratio by dividing the amount of labeled anti-TNFα drug by the amount of labeled internal control; and
(f) determining a second ratio by dividing the resultant integration from step (c) and (d); and
(g) comparing the first ratio determined in step (e) with the second ratio determined in step (f), thereby determining the presence or level of the autoantibody with reference to an internal control.

In a related embodiment, the first ratio determined in step (e) is from about 80:1 to about 100:1. In another related embodiment, the first ratio determined in step (e) is about 100:1. In a related embodiment, the labeled internal control is Biocytin-Alexa 488. In certain embodiments, the amount of the labeled internal control (e.g., Biocytin-Alexa 488) is from about 50 to about 200 pg per 100 µL of sample analyzed. In certain other embodiments, the amount of the labeled internal control (e.g., Biocytin-Alexa 488) is from about 100 to about 200 pg per 100 µL, from about 150 to about 200 pg per 100 µL, from about 50 to about 150 pg per 100 µL, or from about 50 to about 100 pg per 100 µL of sample analyzed. In further embodiments, the amount of the labeled internal control (e.g., Biocytin-Alexa 488) is about 50, 75, 100, 125, 150, 175, or 200 pg per 100 µL of sample analyzed.

In a related embodiment, the anti-TNFα drug is a member selected from the group consisting of REMICADE™ (infliximab), ENBREL™ (etanercept), HUMIRA™ (adalimumab), CIMZIA® (certolizumab pegol), and combinations thereof. In a related embodiment, the anti-TNFα drug is infliximab (REMICADE™). In a related embodiment, the anti-TNFα drug is adalimumab (HUMIRA™). In a related embodiment, the anti-TNFα drug is etanercept (ENBREL™). In a related embodiment, the anti-TNFα drug is CIMZIA® (certolizumab pegol). In a related embodiment, the detected autoantibody is quantitated. In a related embodiment, the labeled complex is eluted first, followed by free labeled anti-TNFα antibody. In a related embodiment, the sample is serum. In a related embodiment, the sample is obtained from a subject receiving therapy with the anti-TNFα drug. In a related embodiment, the size exclusion chromatography is size exclusion-high performance liquid chromatography (SE-HPLC). In a related embodiment, the autoantibody is a member selected from the group consisting of human anti-mouse antibody (HAMA), human anti-chimeric antibody (HACA), human anti-humanized antibody (HAHA), and combinations thereof. In a related embodiment, the detected autoantibody is quantitated.

In a related embodiment, the methods of the present invention further provide determining a subsequent course of therapy. The subsequent course of therapy comprises co-administering an immunosuppressive drug with the anti-TNFα drug when the level of the anti-TNFα drug is a high level and the level of the autoantibody is a low level. In another related embodiment, the subsequent course of therapy comprises increasing the level of the anti-TNFα drug and co-administering an immunosuppressive drug when the level of the anti-TNFα drug is a medium level and the level of the autoantibody is a low level. In another related embodiment, the subsequent course of therapy comprises administering a different anti-TNFα drug when the level of the anti-TNFα drug is a medium level and the level of the autoantibody is a medium level. In yet another related embodiment, the subsequent course of therapy comprises administering a different anti-TNFα drug when the level of the anti-TNFα drug is a low level and the level of the autoantibody is a high level. In another related embodiment, the adalimumab (HUMIRA™) is administered instead of infliximab (REMICADE™).

In some embodiments, the present invention provides a kit for measuring the presence or level of an anti-TNFα drug and the presence or level of an autoantibody to an anti-TNFα drug in a sample, the kit comprising:
(a) a first measuring substrate comprising an amount of a labeled TNFα;
(b) a second measuring substrate comprising an amount of a labeled anti-TNFα drug;
(c) optionally a third measuring substrate comprising an amount of a labeled TNFα and an amount of a labeled internal control;
(d) optionally a fourth measuring substrate comprising an amount of a labeled anti-TNFα drug and an amount of a labeled internal control;
(e) optionally a means for extracting a sample from a subject; and
(f) optionally a pamphlet of instructions for using the kit.

In a related embodiment, the substrate comprises any material that can be deposited with the chemicals of the present invention and include, but are not limited to, nitrocellulose, silica gel, thin-layer chromatography substrates, wooden sticks, cellulose, cotton, polyethylene, combinations thereof, and the like. In another related embodiment, the chemicals of the present invention can be deposited on the aforementioned materials in an ordered array, matrix, or matrix array.

In a related embodiment, the kit further comprises a means for detecting the labeled TNFα, the labeled anti-TNFα drug, and/or the labeled internal control. In a related embodiment, the kit further comprises means for detection including, but not limited to, fluorescence label detection, UV-radiation detection, or iodine exposure. In a related embodiment, the kit further comprises a size exclusion-high performance liquid chromatography (SE-HPLC) instrument. In a related embodiment, the first, second, third, and fourth measuring substrates are selected from nitrocellulose, silica gel, and a size-exclusion chromatographic medium. In a related embodiment, the anti-TNFα drug is a member selected from the group consisting of REMICADE™ (infliximab), ENBREL™ (etanercept), HUMIRA™ (adalimumab), CIMZIA® (certolizumab pegol), and combinations thereof. In a related embodiment, the labeled TNFα is a fluorophore labeled TNFα. In a related embodiment, the sample is serum. In a related embodiment, the sample is obtained from a subject receiving therapy with the anti-TNFα drug. In a related embodiment, the autoantibody is a member selected from the group consisting of human anti-mouse antibody (HAMA), human anti-chimeric antibody (HACA), human anti-humanized antibody (HAHA), and combinations thereof.

IV. Physiological Ranges and Levels of Species Relevant to the Present Invention Therapeutically effective levels of REMICADE™ in a patient treated with REMICADE™ are in the range of about 1 to 10 mg REMICADE™ per kg patient body weight. In some embodiments, the therapeutically effective levels of REMICADE™ are in the range of 3 to 8 mg REMICADE™ per kg patient body weight. In some other embodiments, the therapeutic effective levels of REMICADE™ are about 5 mg REMICADE™ per kg of patient body weight.

A typical dose of REMICADE™ (infliximab) is in the range of about 0.05 µg to about 80 µg per ml. In some embodiments, a dose of REMICADE™ is in the range of about 0.05 µg to about 50 µg per ml. In some other embodiments, a dose of REMICADE™ is about 0.05 µg to about 30 µg per ml. In some embodiments, a dose of REMICADE™ is about 30 µg per ml. In some other embodiments, a dose of REMICADE™ is about 50 µg per ml.

Therapeutically effective levels of HUMIRA™ in a patient treated with HUMIRA™ are in the range of about 0.1 to 10 mg HUMIRA™ per kg patient body weight. In some embodiments, the therapeutically effective levels of HUMIRA™ are in the range of 0.1 to 8 mg HUMIRA™ per kg patient body weight. In some other embodiments, the therapeutic effective levels of HUMIRA™ are about 1 mg HUMIRA™ per kg of patient body weight. In some embodiments, the therapeutic effective levels of HUMIRA™ are about 0.8 mg HUMIRA™ per kg of patient body weight.

A typical dose of HUMIRA™ is in the range of about 0.05 µg to about 150 µg per ml. In some embodiments, a dose of HUMIRA™ is in the range of about 0.05 µg to about 100 µg per ml. In some other embodiments, a dose of HUMIRA™ is about 0.05 µg to about 50 µg per ml. In some embodiments, a dose of HUMIRA™ is about 30 µg per ml. In some embodiments, a dose of HUMIRA™ is about 32 µg per ml. In some other embodiments, a dose of HUMIRA™ is about 50 µg per ml.

V. Exemplary Diseases and Therapeutic Antibodies for the Treatment Thereof

In certain embodiments, the present invention may employ therapeutic monoclonal antibodies. Table 1 provides an exemplary list of therapeutic monoclonal antibodies which have either been approved or are currently in development. An extensive list of monoclonal antibody therapeutics in clinical development and approved products are disclosed in the 2006 PhRMA Report entitled 418 Biotechnology Medicines in Testing Promise to Bolster the Arsenal Against Disease.

Particularly preferred therapeutic antibodies include, but are not limited to, anti-TNFα monoclonal antibodies such as, e.g., (1) Remicade™ (infliximab), a mouse-human IgG I-kappa antiTNFα monoclonal antibody, (2) Enbrel™ (etanercept), a fusion protein of human TNF receptor 2 and human IgG I, and (3) Humira™ (adalimumab), a fully human IgG1-kappa antiTNFα monoclonal antibody. Two other anti-TNFα antibody constructs have shown promise in pivotal phase III trials in patients with some of the same diseases: (4) Cimzia™ CDP870 (certolizlunab pegol), a PEGylated Fab fragment of a humanized anti-TNFα monoclonal antibody, and (5) CNTO 148 (golimlunab), a fully human IgG I-kappa antiTNFα monoclonal antibody.

A preferred class of therapeutic antibodies are anti-TNFα single chain monoclonal antibodies used in treatment of numerous autoimmune diseases, such as rheumatoid arthritis, juvenile idiopathic arthritis, ankylosing spondylitis (Bechterew's disease), inflammatory bowel diseases (Crohn's diseases and ulcerative colitis), severe psoriasis, chronic uveitis, severe sarcoidosis, and Wegener's granulomatosis.

In addition to being useful in determining the bioavailability/concentration of anti-TNFα antibodies, the present invention is also suitable for use in the determination of the bioavailability/concentration of any therapeutic antibody used within the body, such as for therapeutic or diagnostic purposes. Table 1 below also provides a list of medical indications which correlate with various therapeutic monoclonal antibodies used in vivo.

In further embodiments, the methods of the present invention are suitable for use in the determination of the presence or concentration levels of autoantibodies to the therapeutic antibodies.

The present invention can therefore be used in methods of optimizing therapy where the treatment (or diagnosis) comprises administering a therapeutic antibody to the subject. The methods can be for optimizing the treatment (or diagnosis) of one or more of the diseases or disorders referred to herein, including one or more of the following:

Infectious diseases, such as respiratory syncytial virus (RSV), HIV, anthrax, candidiasis, staphylococcal infections, hepatitis C.

Autoimmune diseases, such as rheumatoid arthritis, Crohn's disease, B-cell non hodgkin's lymphoma, Multiple scleorisis, SLE, ankylosing spondylitis, lupus, psoriatic arthritis, erythematosus.

Inflammatory disorders such as rheumatoid arthritis (RA), juvenile idiopatmc arthritis, ankylosing spondylitis (Bechterew's disease), inflammatory bowel diseases (Crohn's diseases and ulcerative colitis), severe psoriasis, chronic uveitis, sarcoidosis, Wegener's granulomatosis, and other diseases with inflammation as a central feature.

Blood disorders, such as sepsis, septic shock, paroxysmal nocturnal hemoglobinuria, and hemolytic uremic syndrome.

Cancer, such as colorectal cancer, non-Hodgkin's lymphoma, B-cell chronic lymphocytic leukemia, anaplastic large-cell-lymphoma, squamous cell cancer of the head and neck, treatment of HER2-overexpressing metastatic breast cancer, acute myeloid leukemia, prostate cancer (e.g., adenocarcinoma), small-cell lung cancer, thyroid cancer, malignant melanoma, solid tumors, breast cancer, early stage HER2-positive breast cancer, first-line non-squamous NSCLC cancers, AML, hairy cell leukemia, neuroblastoma, renal cancer, brain cancer, myeloma, multiple myeloma, bone metastases, SCLC, head/neck cancer, first-line pancreatic, SCLC, NSCLC, head and neck cancer, hematologic and solid tumors, advanced solid tumors, gastrointestinal cancer, pancreatic cancers, cutaneous T-cell lymphoma, non-cutaneous T-cell lymphoma, CLL, ovarian, prostate, renal cell cancers, mesothelin-expressing tumors, glioblastoma, metastatic pancreatic, hematologic malignancies, cutaneous anaplastic large-cell MAb lymphoma, AML, myelodysplastic syndromes.

Cardiovascular disease, such as atherosclerosis acute myocardial infarction, cardiopulmonary bypass, angina.

Metabilic disorders such as diabetes, such as type-I diabetes mellitus.

Digestive disorders, such as Crohn's disease, *C. difficile* disease, ulcerative colitis.

Eye disorders such as uveitis.

Genetic disorders such as paroxysmal nocturnal hemoglobinuria (PNH).

Neurological disorders such as osteoarthritis pain and Alzheimer's disease.

Respiratory disorders such as respiratory diseases, asthma, chronic obstructive pulmonary disorders (COPD, nasal polyposis, pediatric asthma.

Skin diseases, such as psoriasis, including chronic moderate to severe plaque psoriasis.

Transplant rejection, such as acute kidney transplant rejection, reversal of heart and liver transplant rejection, prevention of renal transplant rejection, prophylaxis of acute kidney transplant rejection, renal transplant rejection.

Other disorders, such as diagnosis of appendicitis, kidney inflammation, postmenopausal osteoporosis (bone disorders), hypereosinophilic syndrome, eosinophilic esophagitis and peanut allergy.

In one embodiment, the disease is selected from one or more of the above groups of specific diseases and disorders.

TABLE 1

| Therapeutic and diagnostic monoclonal antibodies | | |
| --- | --- | --- |
| Product Name | Sponsor | Indication |
| Infectious diseases | | |
| Synagis ® palivizumab | MedImmune | prevention of respiratory syncytial virus (RSV) |
| anti-HIV-1 MAb | Polymun Scientific Vienna, Austria | HIV infection treatment |

TABLE 1-continued

Therapeutic and diagnostic monoclonal antibodies

| Product Name | Sponsor | Indication |
|---|---|---|
| CCR5 MAb | Hunan Genome Sciences Rockville, MD | HIV infection |
| Cytolin ® anti-CD8 MAb | CytoDyn Santa Fe, NM | HIV infection |
| NM01 | SRD Pharmaceuticals Los Angeles, CA | HIV infection |
| PRO 140 | Progenics Pharmaceuticals Tarrytown, NY | HIV infection |
| TNX | 355 Tanox MAb HIV infection Please II | 355 Tanox MAb HIV infection Phase II |
| ABthrax ™ raxibacumab | Human Genome Sciences | anthrax |
| Anthim ™ (ETI-204) (Orphan Drug) | Elusys Therapeutics | anthrax |
| anti-hsp90 MAb | NeuTec Pharma | candidiasis |
| anti-staph MAb | MedImmune | Prevention of staphylococcal infections |
| Aurexis tefibazumab | Inhibitex | prevention and treatment of *S. aureus* bacteremia |
| Bavituximab | Peregrine Pharmaceuticals | hepatitis C treatment |
| MDX-1303 | Medarex PharmAthene | anthrax |
| Numax ™ motavizumab | MedImmune | RSV |
| Tarvacin ™ bavituximab | Peregrine Pharmaceuticals | hepatitis C |
| XTL 6865 | XTL Biopharmaceuticals | hepatitis C |

Autoimmune disorders

| | | |
|---|---|---|
| Humira ® adalimumab | Abbott Laboratories | rheumatoid arthritis |
| Remicade ™ infliximab | Centocor | Crohn's disease, rheumatoid arthritis |
| Rituxan ® ritiximab | Genentech Biogen Idec | B-cell non hodgkin's lymphoma, relapse in patients following rituxan treatment. Rheumatoid arthritis |
| Tysarbi ® natalizumab | Biogen Idec | Multiple sclerosis |
| ART 874 | Abbott Laboratories | multiple sclerosis |
| Actemra | Roche | rheumatoid arthritis |
| AME 527 | Applied Molecular | rheumatoid arthritis |
| AMG 108 | Amgen | rheumatoid arthritis |
| AMG 714 | Amgen | rheumatoid arthritis |
| anti-CD16 MAb | MacroGenics | immune thrombocytopenic |
| CNTO 1275 | Centocor Horham, PA | multiple sclerosis |
| daclizumab (anti-CD25 MAb) | PDL BioPharma Fremont, CA Biogen Idec Cambridge, MA | multiple sclerosis (see also respiratory) |
| denosumah (AMG 162) | Amgen Thousand Oaks, CA | rheumatoid arthritis |
| ETI-201 | Elusys Therapeutics Pine Brook, NJ | SLE |
| golimumab | Centocor Horsham, PA | rheumatoid arthritis |
| HuMax-CD20 (ofatumumab) | Genmab Princeton, NJ | rheumatoid arthritis |
| Humira ® adalimumab | Abbott Laboratories | ankylosing spondylitis juvenile rheumatoid arthritis |
| HuZAF ™ fontolizumab | PDL BioPharma Fremont, CA Biogen Idec Cambridge, MA | rheumatoid arthritis |
| IMMU-106 (hCD20) | Immunomedics Morris Plains, NJ | autoimmune disease |
| LymphoStat-B ™ belimumab | Human Genome Sciences Rockville, MD | rheumatoid arthritis, SLE |
| MEDI-545 (MDX-1103) | Medarex Princeton, NJ MedImmune Gaithersburg, MD | lupus |

TABLE 1-continued

Therapeutic and diagnostic monoclonal antibodies

| Product Name | Sponsor | Indication |
|---|---|---|
| MLN 1202 | Millennium Pharmaceuticals Cambridge, MA | multiple sclerosis |
| ocrelizumab (2nd anti-CD20) (R1594) | Genentech South San Francisco, CA Biogen Idec Cambridge, MA Roche Nutley, NJ | rheumatoid arthritis |
| OKT3-gamma-1 | Johnson & Johnson Pharmaceutical Research & Development Raritan, NJ | psoriatic arthritis |
| Rituxan ® rituximab | Genentech South San Francisco, CA Biogen Idec Cambridge, MA | rheumatoid arthritis (DMARD inadequate responders), lupus, primary progressive multiple sclerosis, SLE (see also cancer) relapsing-remitting multiple sclerosis |
| TRX 1 (anti CD4) | TolerRx Cambridge, MA | cutaneous lupus erythethnatosus |
| Blood disorders | | |
| ReoPro ® | Centocor | anti-platelet prevention of blood clots |
| abciximab | Eli Lilly | (PTCA), angina (PTCA) |
| urtoxazumab | Teijin Pharma | hemolytic uremic |
| Afelimomab | Abbot Laboratories | Sepsis, septic shock |
| Eculizumab | Alexion Pharmaceuticals | Paroxysmal nocturnal hemoglobinurea |
| Cancer | | |
| Avastin ™ bevacizumab | Genentech | metastatic colorectal cancer |
| Bexxar ® tositumomab, iodine I131 tositumomab | GlaxoSmithKline | non-Hodgkin's lymphoma |
| Campath ® alemtuzumab | Berlex Laboratories Genzyme | B-cell chronic lymphocytic leukemia |
| Erbitux ™ cetuximab | Bristol-Myers Squibb Medarex | colorectal cancer squamous cell cancer of the head and neck |
| Herceptin ® trastuzumab | Genentech | treatment of HER2-overexpressing metastatic breast cancer |
| Mylotarg ™ gemtuzumab ozogamicin | Wyeth | Acute myeloid leukemia |
| OncoScint ® CR/OV satumomab pendetide | CYTOGEN | detection, staging and follow-up of colorectal cancers |
| ProstaScint ® capromab pentetate | CYTOGEN | detection, staging and follow-up of prostate adenocarcinoma |
| Rituxan ® ritiximab | Genentech Biogen Idec | B-cell non hodgkin's lymphoma, relapse in patients following rituxan treatment. |
| Verluma ® noletumomab | DuPont Pharmaceuticals | detection of small-cell lung cancer |
| Zevalin ™ ibritumomab tiuxetan | IDFC Pharmaceuticals | Non-hodgkin's lymphoma |
| 1311 huA33 | Life Science Pharmaceuticals Greenwich, CT | colorectal cancer |
| 1D09C3 | GPC Biotech Waltham, MA | relapsed/refractory B-cell lymphomas |
| AGS PSCA MAb | Agensys Santa Monica, CA Merck Whitehouse Station, NJ | prostate cancer |
| AMG 102 | Amgen Thousand Oaks, CA | cancer |

TABLE 1-continued

Therapeutic and diagnostic monoclonal antibodies

| Product Name | Sponsor | Indication |
| --- | --- | --- |
| AMG 479 | Amgen Thousand Oaks, CA | cancer |
| AMG 623 | Amgen Thousand Oaks | B-cell chronic lymphocytic leukemia (CLL) (see also autoimmune) |
| AMG 655 | Amgen Thousand Oaks | cancer |
| AMG 706 | Amgen Thousand Oaks | imatinib-resistant GIST, advanced thyroid cancer |
| AMG 706 | Arngen Thousand Oaks, CA | imatinib resistant GIST, advanced thyroid cancer |
| anti-CD23 MAb | Biogen Idec Cambridge, MA | CLL |
| anti-CD80 MAb | Biogen Idec Cambridge, MA | non-Hodgkin's B |
| anti-idiotype cancer vaccine | Viventia Biotech Toronto, Ontario | malignant melanoma |
| anti-lymphotoxin beta receptor MAb | Biogen Idec Cambridge, MA. | solid tumors |
| anti-PEM MAb | Somanta Pharmaceuticals Irvine, CA | cancer |
| anti-Tac(Fv)-PE38 immunotoxin | National Cancer Institute Bethesda, MD | leukemia, lymphoma. |
| Avastin ® bevacizumab | Genentech South San Francisco, CA | relapsed metastatic colorectal cancer first line metastatic breast, first-line non-squamous NSCLC cancers |
| AVE 9633 maytansin-loaded anti-CD33 MAb | sanofi aventis Bridgewater, NJ | AML |
| bavituximab | Peregrine Pharmaceuticals Tustin, CA | solid cancers (see also infectious) |
| CAT 3888 | Cambridge Antibody Technology | hairy cell leukemia |
| chimeric MAb | National Cancer Institute | neuroblastoma |
| CNTO 328 | Centocor | renal cancer |
| Cotara ™ | Peregrine Pharmaceuticals | brain cancer |
| bivatuzumab | Boehringer Ingelheim Pharmaceuticals Ridgefield, CT | cancer |
| CP-751,871 | Pfizer Daiichi | multiple myeloma cancer |
| CS 1008 | Sankyo Sankyo Sankyo Pharma Development Parsippany, NJ | |
| BrevaRex ™ antibody based immunotherapy | ViRexx Edmonton, Alberta | breast cancer, multiple myeloma |
| denosumab | Amgen | bone loss induced by hormone ablation therapy for breast or prostate cancer, prolonging bonemetastases-free survival (see also autoimmune, other) bone metastases in breast cancer |
| ecromeximab | Kyowa Hakko USA | malignant melanoma |
| EMD 273063 | EMD Lexigen | solid tumors malignant melanoma, neuroblastoma, SCLC |
| Erbitux ™ | Bristol Myers Squibb | head/neck cancer, first-line palicreatic, first-line NSCLC, -second-line NSCLC, first line colorectal, second-line colorectal cancers |
| GMK | Progenies Pharmaceuticals | prevention of recurrence following surgery to remove primacy melanoma in high-risk patients |
| Campath ® alemtuzumab | National Cancer Institute Bethesda, MD Berlex Laboratories Montville, NJ | leukemia, lymphoma |

TABLE 1-continued

Therapeutic and diagnostic monoclonal antibodies

| Product Name | Sponsor | Indication |
| --- | --- | --- |
| Herceptin ® trastuzumab | Genentech South San Francisco, CA | early stage HER2-positive breast cancer first-line metastatic HER2-positive breast cancer in combination with Taxotere ® |
| HGS-ETR1 | Human Genome Sciences Rockville, MD | hematologic and solid tumors |
| HGS ETR2 (mapatumumab) | Human Genome Sciences Rockville, MD | hematologic and solid tumors |
| HGS-TR2J | Human Genome Sciences Rockville, MD | advanced solid tumors |
| HuC242-DM4 | ImmunoGen Cambridge, MA | colorectal, gastrointestinal, NSCLC, pancreatic cancers |
| HuMax-CD4 (zanolimumab) | Genmab Princeton, NJ Serono Rockland, MA | cutaneous T-cell lymphoma non-cutaneous T-cell lymphoma |
| HuMax CD20 (ofatumumab) | Gemnab Princeton, NJ | CLL, non-Hodgkin's lymphoma (see also autoimmune) |
| HuMax-EGFr | Genmab Princeton, NJ | head and neck cancer |
| huN901-DM1 | ImmunoGen Cambridge, MA | SCLC multiple myeloma |
| ipilimumab (MDX | Bristol-Myers Squibb Medarex, Princeton | melanoma monotherapy leukemia, lymphoma, ovarian, prostate, renal cell cancers melanoma (MCX-010 +/− DTIC) second-line metastatic melanoma (MDX-010 disomotide/overnotide MDX-1379) |
| M195-bismuth 213 conjugate | Actinium Pharmaceuticals Florham Park, NJ | AML |
| M200 (volocixirnab) | PDL BioPharma Fremont, CA Biogen Idec Cambridge, MA | advanced solid tumors |
| MAb HeFi-1 | National Cancer Institute Bethesda, MD | lymphoma, non-Hodgkin's lymphoma |
| MDX-060 (iratumumab) | Medarex Princeton, NJ | Hodgkin's disease, anaplastic large-cell-lymphoma |
| MDX-070 | Medarex Princeton, NJ | prostate cancer |
| MDX-214 | Medarex Princeton, NJ | ECFR-expressing cancers |
| MEDI-507 siplizumab | MedImmune Gaithersburg, MD | T-cell lymphoma infections melanoma, prostate cancer |
| MEDI-522 | MedImmune Gaithersburg, MD National Cancer Institute Bethesda, MD MedImmune Gaithersburg, MD | solid tumors |
| MORAb 003 | Morphotek Exton, PA | ovarian cancer |
| MORAb 009 | Morphotek Exton, PA | mesothelin-expressing tumors |
| neuradiab | Bradmer Pharmaceuticals Louisville, KY | glioblastoma |
| nimotuzumab (Orphan Drug) | YM Biosciences Mississauga, Ontario | metastatic pancreatic, NSCLC hematologic malignancies |
| ocrelizumab (2nd anti-CD20) (R1594) | Genentech South San Francisco, CA Biogen Idec Cambridge, MA Roche Nutley, NJ | (see also autoimmune) |
| Omnitarg ™ pertuzumab | Genentech South San Francisco, CA | ovarian cancer |
| OvaRex ® oregovomab | ViRexx MAb Edmonton, Alberta | ovarian cancer |
| PAM 4 | Merck Whitehouse Station, NJ | pancreatic cancer |

TABLE 1-continued

Therapeutic and diagnostic monoclonal antibodies

| Product Name | Sponsor | Indication |
|---|---|---|
| panitumumab (rHuMAb EGFr) | Abgenix | colorectal cancer |
| Proleukin ® | Chiron Emeryville, CA | Non-hodgkin's lymphoma |
| PSMA | Progenics Pharmaceuticals Tarrytown, NY | prostate cancer |
| R1550 | Roche Nutley, NJ YM YM | metastatic breast cancer |
| RadioTheraCIM | BioSciences Mississauga, Ontario | glioma |
| RAV 12 | Raven Biotechnologies South San Francisco, CA | cancer |
| Renearex ® G250 | Wilex Miulich, Germany | renal cancer |
| Rituxan ® rituximab | Genentech South San Francisco, CA Biogen Idec Cambridge, MA | indolent non-Hodgkin's lymphoma induction therapy (see also autoimmune) relapsed or refractory CLL |
| SGN30 (Orphan Drug) | Seattle Genetics Bothell, WA | cutaneous anaplastic large-cell MAb lyrphoma, systemic anaplastic large-cell lymphoma, Hodgkin's disease |
| SGN-33 (lintuzumab) | Seattle Genetics Bothell, WA | AML, myelodysplastic syndromes CLL multiple myeloma, non Hodgkin's lymphoma |
| SGN-40 | Seattle Genetics Bothell, WA | |
| sibroturtunab | Life Science Pharmaceuticals Greenwich, CT | colorectal, head and neck, lung cancers |
| Tarvacin ™ bavituximab | Peregrine Pharmaceuticals Tustin, CA | solid tumors (see also infectious) |
| ticilimumab | Pfizer New York, NY | metastatic melanoma prostate cancer ticilimumab |
| TNX-650 Zevalin ™ ibritumomab tiuxetan | Tanox Houston, TX National Cancer Institute Bethesda Biogen | Hodgkin's disease leukemia, lymphoma non-Hodgkin's lymphoma |

Cardiovascular disease

| MLN 1202 | Millennium Pharmaceuticals Cambridge, MA | atherosclerosis (see also autoimmune) |
|---|---|---|
| pexelizumab | Alexion Pharmaceuticals Cheshire, CT Procter & Gamble Pharmaceuticals Mason, OH | acute myocardial infarction, cardiopulmonary bypass |

Diabetes and Related Conditions

| anti-CD3 MAb | MacroGenics Rockville, MD | type-1 diabetes mellitus |
|---|---|---|
| OKT3-gamma-1 | Johnson & Johnson Pharmaceutical Research & Development | type-1 diabetes mellitus |
| TRX 4 (anti-CD3) | TolerRx Cambridge, MA | type-1 diabetes mellitus |

Digestive Disorders

| Remicade ™ infliximab | Centocor | Crohn's disease |
|---|---|---|
| ABT 874 | Abbott Laboratories Abbott Park, IL, | Crohn's disease (see also autoimmmune) |
| CNTO 1275 | Centocor Horsham, PA | Crolin's disease Phase II (see also autoinunurle, skin) (610) 651-6000 |
| Humira ® adalimumab | Abbott Laboratories Abbott Park, IL | Crohn's disease Phase III (see also autoimmune, skin) |
| MDX-066 (CDA-1) | Medarex Princeton, NJ | (847) 9361189 C. difficile disease |
| MDX-1100 | Millennium Pharmaceuticals Cambridge, MA | ulcerative colitis |
| Nuvion ® visilizumab | PDT, BioPharma Fremont, CA | I.V. steroid-refractory ulcerative colitis Crohn's disease |
| Tysarbi ® natalizumab | Biogen Idec Cambridge, MA | Crohn's disease |

TABLE 1-continued

Therapeutic and diagnostic monoclonal antibodies

| Product Name | Sponsor | Indication |
|---|---|---|
| Eye Conditions | | |
| golimumab | Centocor Horsham, PA | uveitis (see also autoimmune) |
| Genetic Disorders | | |
| Soliris ™ eculizumab (Orphan Drug) | Alexion Pharmaceuticals Cheshire, CT | paroxysmal nocturnal hemoglobinuria (PNH) |
| Neurological Disorders | | |
| RN624 | Rinat Neuroscience South San Francisco, CA | osteoarthritis pain |
| RN1219 | Rinat Neuroscience South San Francisco, CA | Alzheimer's disease |
| Respiratory Disorders | | |
| ABN 912 | Novartis Pharmaceuticals East Hanover, NJ | asthma, chronic obstructive pulmonary disorders (COPD) |
| ABX-IL8 | Amgen Thousand Oaks, CA | COPD |
| AMG 317 | Amgen Thousand Oaks, CA | asthma |
| daclizumab (anti-CD25 MAb) | Protein Design Labs Fremont, CA Roche Nutley, NJ | asthma (see also autoimmune) |
| MEDI-528 anti-TL-9 MAb | MedImmune Gaithersburg, MD | asthma |
| mepolizumab (anti-TL5 MAb) | GlaxoSmithKline Philadelphia, PA Rsch. Triangle Park, NC | asthma and nasal polyposis (see also other) |
| TNX-832 | Tanox Houston, TX | respiratory diseases |
| Xolair ® omalizumab | Genentech South San Francisco, CA Novartis Pharmaceuticals | pediatric asthma (see also other) |
| Skin Disorders | | |
| Raptiva ® efalizumab | Genentech | chronic moderate to severe plaque psoriasis |
| CNTO1275 | XOMA Centocor | psoriasis see also autoimmune, digestive) |
| Humira ® adalimumab | Abbott Laboratories | psoriasis see also autoimmune, digestive) |
| TRX 4 | TolerRx | psoriasis (see also diabetes) |
| Transplatation | | |
| ORTHOCLONE OKT ® 3 muromonab-CD3 | Ortho Biotech | acute kidney transplant rejection, reversal of heart and liver transplant rejection |
| Simulect ® basiliximab | Novartis Pharmaceuticals | prevention of renal transplant rejection |
| Zenapax ® daclizumab OKT3-gamma-1 | Roche Protein Design Labs Johnson & Johnson | prophylaxis of acute kidney transplant rejection renal transplant rejection (see also autoimmune, diabetes) |
| Other | | |
| NeutroSpec ™ technetium 99m Tc fanolesomab | Palatin Technologies | diagnosis of appendicitis |
| CR 0002 | CuraGen | kidney inflammation |
| denosumab (AMG 162) | Amgen | Postmenopausal osteoporosis, see also autoimmune and cancer |
| mepolizumab (anti-IL5 MAb) | GlaxoSmithKllne | hypereosinophilic syndrome, eosinophlic esophagitis (see also respiratory) |
| Xolair ® omalizumab | Genentech Tanox | peanut allergy (see also respiratory) |

VI. Therapy and Therapeutic Monitoring

Once the diagnosis or prognosis of a subject receiving anti-TNFα drug therapy has been determined or the likelihood of response to anti-TNFα drug has been predicted in an individual diagnosed with a disease and disorder in which TNFα has been implicated in the pathophysiology, e.g., but not limited to, shock, sepsis, infections, autoimmune diseases, RA, Crohn's disease, transplant rejection and graft-versus-host disease, according to the methods described herein, the present invention may further comprise recommending a course of therapy based upon the diagnosis, prognosis, or prediction. In certain instances, the present invention may further comprise administering to the individual a therapeutically effective amount of an anti-TNFα drug useful for treating one or more symptoms associated with disease and disorder in which TNF-α has been implicated in the pathophysiology. For therapeutic applications, the anti-TNFα drug can be administered alone or co-administered in combination with one or more additional anti-TNFα drugs and/or one or more drugs that reduce the side-effects associated with the anti-TNFα drug (e.g., an immunosuppressive agent). Examples of anti-TNFα drugs are described herein include, but are not limited to, REMICADE™ (infliximab), ENBREL™ (etanercept), HUMIRA™ (adalimumab), CIMZIA® (certolizumab pegol), biologic agents, conventional drugs, and combinations thereof. As such, the present invention advantageously enables a clinician to practice "personalized medicine" by guiding treatment decisions and informing therapy selection and optimization for anti-TNFα drugs such that the right drug is given to the right patient at the right time.

Anti-TNFα drug can be administered with a suitable pharmaceutical excipient as necessary and can be carried out via any of the accepted modes of administration. Thus, administration can be, for example, intravenous, topical, subcutaneous, transcutaneous, transdermal, intramuscular, oral, buccal, sublingual, gingival, palatal, intra-joint, parenteral, intra-arteriole, intradermal, intraventricular, intracranial, intraperitoneal, intralesional, intranasal, rectal, vaginal, or by inhalation. By "co-administer" it is meant that an anti-TNFα drug is administered at the same time, just prior to, or just after the administration of a second drug (e.g., another anti-TNFα drug, a drug useful for reducing the side-effects of the anti-TNFα drug, etc.).

A therapeutically effective amount of an anti-TNFα drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" includes physically discrete units suitable as unitary dosages for human subjects and other mammals, each unit containing a predetermined quantity of an anti-TNFα drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the anti-TNFα drug.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an anti-TNFα drug, any of the following: a diluent such as lactose, sucrose, dicalcium phosphate, and the like; a disintegrant such as starch or derivatives thereof, a lubricant such as magnesium stearate and the like; and a binder such a starch, gum acacia, polyvinylpyrrolidone, gelatin, cellulose and derivatives thereof. An anti-TNFα drug can also be formulated into a suppository disposed, for example, in a polyethylene glycol (PEG) carrier.

Liquid dosage forms can be prepared by dissolving or dispersing an anti-TNFα drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An anti-TNFα drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an anti-TNFα drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In therapeutic use for the treatment of diseases and disorders in which TNFα has been implicated in the pathophysiology, an anti-TNFα drug can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of disease, disorder, or symptoms, and the anti-TNFα drug being employed. For example, dosages can be empirically determined considering the type and severity of the disease, disorder, and/or symptoms according to the methods described herein. The dose administered to an individual, in the context of the present invention, should be sufficient to affect a beneficial therapeutic response in the individual over time. The size of the dose can also be determined by the existence, nature, and extent of any adverse side-effects that accompany the administration of a particular anti-TNFα drug in an individual. Determination of the proper dosage for a particular situation is within the skill of the practitioner. Generally, treatment is initiated with smaller dosages which are less than the optimum dose of the anti-TNFα drug. Thereafter, the dosage is increased by small increments until the optimum effect under circumstances is reached. For convenience, the total daily dosage may be divided and administered in portions during the day, if desired.

As used herein, the term "anti-TNFα drug" includes all pharmaceutically acceptable forms of a drug that is useful for treating one or more symptoms associated with the diseases and disorders in which TNF-α has been implicated in the pathophysiology. For example, the anti-TNFα drugs can be in a racemic or isomeric mixture, a solid complex bound to an ion exchange resin, or the like. In addition, the anti-TNFα drugs can be in a solvated form. The term is also intended to include all pharmaceutically acceptable salts, derivatives, and analogs of the anti-TNFα drugs being described, as well as combinations thereof. For example, the pharmaceutically acceptable salts of an anti-TNFα drugs include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of an anti-TNFα drugs is suitable for use in the methods of the present invention, e.g., a pharmaceutically acceptable salt of an anti-TNFα drugs, a free base of an anti-TNFα drugs, or a mixture thereof. Examples of suitable anti-TNFα drugs include, but are not limited to, biologic agents, conventional drugs, and combinations thereof.

Therapeutic agents include, e.g., anti-cytokine and chemokine antibodies such as anti-tumor necrosis factor alpha (TNFα) antibodies. Non-limiting examples of anti-TNFα antibodies include: chimeric monoclonal antibodies such as infliximab (Remicade®) (Centocor, Inc.; Horsham, Pa.), which is a chimeric IgG1 anti-TNFα monoclonal antibody; humanized monoclonal antibodies such as CDP571 and the PEGylated CDP870; fully human monoclonal antibodies such as adalimumab (Humira®) (Abbott Laboratories; Abbott Park, Ill.); p75 fusion proteins such as etanercept (Enbrel®) (Amgen; Thousand Oaks, Calif.; Wyeth Pharmaceuticals Inc.; Collegeville, Pa.), small molecules (e.g., MAP kinase inhibitors); and combinations thereof. See, Ghosh, *Novartis Found Symp.*, 263:193-205 (2004).

Other biologic agents include, e.g., anti-cell adhesion antibodies such as natalizumab (Tysabri®) (Elan Pharmaceuticals, Inc.; Dublin, Ireland; Biogen Idec; Cambridge, Mass.), which is a humanized monoclonal antibody against the cellular adhesion molecule α4-integrin, and MLN-02 (Millennium Pharmaceuticals; Cambridge, Mass.), which is a humanized IgG1 anti-α407-integrin monoclonal antibody; anti-T cell agents; anti-CD3 antibodies such as visilizumab (Nuvion®) (PDL BioPharma; Incline Village, Nev.), which is a humanized IgG2M3 anti-CD3 onoclonal antibody; anti-CD4 antibodies such as priliximab (cM-T412) (Centocor, Inc.; Horsham, Pa.), which is a chimeric anti-CD4 monoclonal antibody; anti-IL-2 receptor alpha (CD25) antibodies such as daclizumab Zenapax®) (PDL BioPharma; Incline Village, Nev.; Roche; Nutley, N.J.), which is a humanized IgG1 anti-CD25 monoclonal antibody, and basiliximab (Simulect®) (Novartis; Basel, Switzerland), which is a chimeric IgG1 anti-CD25 monoclonal antibody; and combinations thereof.

An individual can also be monitored at periodic time intervals to assess the efficacy of a certain therapeutic regimen once diagnostic, prognostic and/or predictive information has been obtained from the individual's sample. For example, the presence or concentration level of a therapeutic antibody and/or an autoantibody directed to the therapeutic antibody may change based on the therapeutic effect of treatment with the therapeutic antibody. In certain embodiments, the patient can be monitored to assess response and understand the effects of certain drugs or treatments in an individualized approach. Additionally, patients may not respond to a drug, but the antibody levels may change, suggesting that these patients belong to a special population (not responsive) that can be identified by their antibody levels. These patients can be discontinued on their current therapy and alternative treatments prescribed.

An individual can also be monitored at periodic time intervals to assess the concentrations or levels of various antibodies. The antibody levels at various time points, as well as the rate of change of the antibody levels over time is significant. In certain instances, the rate of increase of one or more antibodies (e.g., autoantibodies to anti-TNFα antibodies) in an individual over a threshold amount indicates the individual has a significantly higher risk of developing complications or risk of side-effects. Information obtained from serial testing in the form of a marker velocity (i.e., the change in antibody levels over a time period) may be associated with the severity of the disease, the risk of complications of disease, and/or the risk of side-effects.

The methods of the present invention also provide for identifying primary non- or low-responders, e.g, for treatment with a therapeutic monoclonal antibody. These primary non- or low-responders may, for example, be patients that happen to have an innate or a pre-developed immunoglobulin response to the therapeutic agent. Where the therapeutic agent is a diagnostic antibody, the identification of primary non- or -low responders can ensure the selection of a suitable therapeutic agent for each individual patient.

The method according to the invention may, for example, be used for identifying patients with secondary response failure. Secondary response failures can be asymptomatic, i.e, the only symptoms are that the treatment has become less effective or even non-effective. In certain instances, the methods of the present invention are useful for identifying the development of secondary response failure before the patient or medical practitioner has noticed that the treatment is less effective. A higher dosage of treatment may be applied to ensure the correct in vivo concentration is achieved, or an alternative treatment can be selected, or a combination thereof. Where the therapeutic agent is a diagnostic agent, the development of secondary response failure can be particularly catastrophic. Radio-labeled monoclonal antibodies are routinely used in the monitoring of diseases such as cancers, and some infectious diseases, where it is important to determine the size and/or location of the disease/agent, e.g., in identifying the presence and/or location of any secondary metastases. When the development of response failure (either primary or secondary) occurs unnoticed, the patient may be given the 'all clear', i.e., a false negative result, which can lead to the cessation of treatment and the latter reappearance of the disease, often in a far more developed and possibly untreatable condition.

A further category of response failure is the development of (e.g., secondary) response failure associated with adverse side-effects. The development of a host-immune response in a subject can be accompanied by deleterious or unpleasant side-effects. These may be caused by the development of antibodies which recognize the human or humanized therapeutic agents but which fail to distinguish between other host immunoglobulins. The methods of the present invention are therefore suitable to identify subjects who have either an innate or previously-developed immune response to the therapeutic agent and who may, for example, be vulnerable to adverse side-effects associated with response failure.

The methods of the present invention are suitable for the selection and management of treatment regimes which involve the administration of monoclonal therapeutic agents to patients. Accordingly, the methods for determining the concentration or bioavailability of a therapeutic antibody as described herein can be incorporated into a method of treatment of a disease or a disorder. By monitoring the immunological status of a patient using the methods of the present invention during the course of therapeutic treatment, the selection and/or administration of the therapeutic agent can be tailored to ensure maximum therapeutic benefit to the patient, while ensuring the cost-effective use of expensive therapeutic agents.

The methods of the present invention may be used to determine whether a patient requires either an altered dosage regime of the therapeutic agent (e.g., therapeutic antibody) or an alternative pharmaceutical therapy.

The methods of the present invention may further involve a periodic assessment of the serum concentration or bioavailability of the therapeutic agent (e.g., therapeutic antibody) in the patient.

The methods of the present invention also provide for determining whether a subject has developed an immune response to a therapeutic agent such as a therapeutic antibody.

The present invention also provides for a method of determining whether the lack of treatment response in a patient is due to the formation of patient-derived immunoglobulins against a therapeutic antibody such as, e.g., an anti-TNFα antibody.

The present invention further provides for a method of selecting the appropriate drug treatment for a patient suffering from a disease which is treatable with a therapeutic antibody.

The present invention also provides for a prognostic method for the determination of the likelihood of whether a patient will develop secondary response failure to a therapeutic antibody.

VII. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Novel Mobility Shift Assay for Measuring Levels of Anti-TNFα Biologics This example illustrates a novel homogeneous assay for measuring anti-TNFα drug concentration in a patient sample (e.g., serum) using size exclusion chromatography to detect the binding of the anti-TNFα drug to fluorescently labeled TNFα. The assay is advantageous because it obviates the need for wash steps, uses fluorophores that allow for detection on the visible and/or fluorescent spectra which decreases background and serum interference issues, increases the ability to detect anti-TNFα drugs in patients with a low titer due to the high sensitivity of fluorescent label detection, and occurs as a liquid phase reaction, thereby reducing the chance of any changes in the epitope by attachment to a solid surface such as an ELISA plate.

In one exemplary embodiment, TNFα is labeled with a fluorophore (e.g., Alexa$_{647}$), wherein the fluorophore can be detected on either or both the visible and fluorescent spectra.

The labeled TNFα is incubated with human serum in a liquid phase reaction to allow the anti-TNFα drug present in the serum to bind. The labeled TNFα can also be incubated with known amounts of the anti-TNFα drug in a liquid phase reaction to create a standard curve.

Following incubation, the samples are loaded directly onto a size exclusion column. Binding of the anti-TNFα drug to the labeled TNFα results in a leftward shift of the peak compared to labeled TNFα alone. The concentration of the anti-TNFα drug present in the serum sample can then be compared to the standard curve and controls.

FIG. 1 shows an example of the assay of the present invention wherein size exclusion HPLC is used to detect the binding between TNFα-Alexa$_{647}$ and HUMIRA™ (adalimumab). As shown in FIG. 1, the binding of HUMIRA™ to TNFα-Alexa$_{647}$ caused a shift of the TNFα-Alexa$_{647}$ peak to the left.

Figure 2:
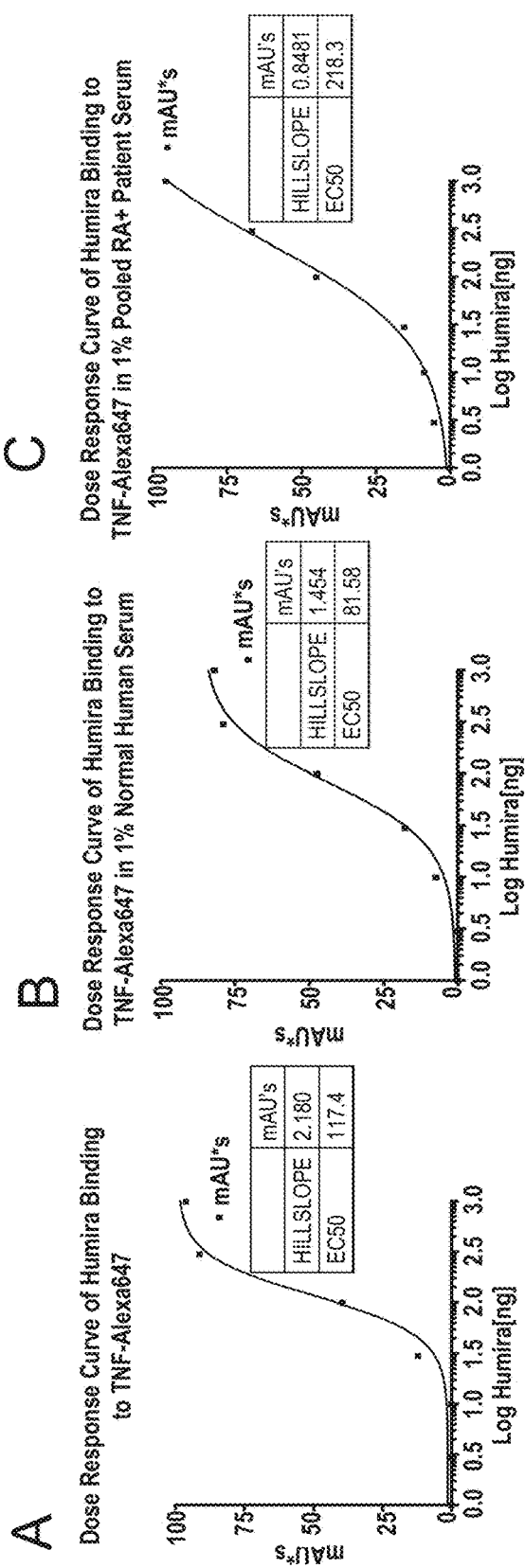
FIG. 2 shows dose response curves of HUMIRA™ binding to TNFα-Alexa$_{647}$.

FIG. 2 shows dose response curves of HUMIRA™ binding to TNFα-Alexa$_{647}$. In particular, FIG. 2A shows that HUMIRA™ dose-dependently increased the shift of TNFα-Alexa$_{647}$ in the size exclusion chromatography assay. FIG. 2B shows that the presence of 1% human serum did not have a significant effect on the shift of TNFα-Alexa$_{647}$ in the size exclusion chromatography assay. FIG. 2C shows that the presence of pooled RF-positive serum did not have a significant effect on the shift of TNFα-Alexa$_{647}$ in the size exclusion chromatography assay.

As such, this example demonstrates the utility of the present invention in monitoring patients receiving an anti- TNFα drug such as HUMIRA™: (1) to guide in the determination of the appropriate drug dosage; (2) to evaluate drug pharmacokinetics, e.g., to determine whether the drug is being cleared from the body too quickly; and (3) to guide treatment decisions, e.g., whether to switch from the current anti-TNFα drug to a different TNFα inhibitor or to another type of therapy.

Example 2. Novel Mobility Shift Assay for Measuring HACA and HAHA Levels

This example illustrates a novel homogeneous assay for measuring autoantibody (e.g., HACA and/or HAHA) concentrations in a patient sample (e.g., serum) using size exclusion chromatography to detect the binding of these autoantibodies to fluorescently labeled anti-TNFα drug. The assay is advantageous because it obviates the need for wash steps which remove low affinity HACA and HAHA, uses fluorophores that allow for detection on the visible and/or fluorescent spectra which decreases background and serum interference issues, increases the ability to detect HACA and HAHA in patients with a low titer due to the high sensitivity of fluorescent label detection, and occurs as a liquid phase reaction, thereby reducing the chance of any changes in the epitope by attachment to a solid surface such as an ELISA plate.

The clinical utility of measuring autoantibodies (e.g., HACA, HAHA, etc.) that are generated against TNFα inhibitors is illustrated by the fact that HACAs were detected in 53%, 21%, and 7% of rheumatoid arthritis patients treated with 1 mg/kg, 3 mg/kg, and 10 mg/kg infliximab. When infliximab was combined with methotrexate, the incidence of antibodies was lower 15%, 7%, and 0%, which indicates that concurrent immunosuppressive therapy is effective in lowering anti-drug responses, but also indicates that a high dose of anti-TNFα drug might lead to tolerance. In Crohn's disease, a much higher incidence was reported; after the fifth infusion, 61% of patients had HACA. The clinical response was shortened when HACAs were present. See, Rutgeerts, *N. Engl. J Med.*, 348:601-608 (2003). A retrospective study of infliximab and HACA levels measured over a 3 year period from 2005 to 2008 in 155 patients demonstrated that HACAs were detected in 22.6% (N=35) of patients with inflammatory bowel disease. See, Afif et al., "Clinical Utility of Measuring Infliximab and Human Anti-Chimeric Antibody Levels in Patients with Inflammatory Bowel Disease"; paper presented at Digestive Disease Week; May 30-Jun. 3, 2009; Chicago, Ill. The authors concluded that changing treatment based on clinical symptoms alone may lead to inappropriate management.

Figure 3:
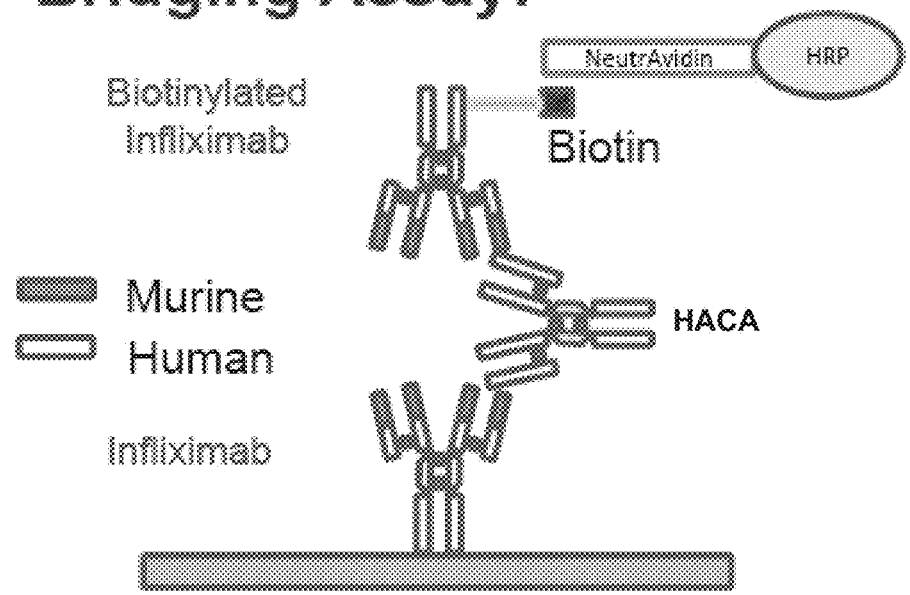
FIG. 3 shows a current ELISA-based method for measuring HACA levels, known as the bridging assay.

The homogeneous mobility shift assay is advantageous over current methods such as the bridging assay shown in FIG. 3 for measuring autoantibody (e.g., HACA and/or HAHA) concentrations in a patient sample because the inventive method is capable of measuring the concentration of autoantibodies such as HACA without non-specific binding and solid phase interference from the ELISA plate, without interference from the anti-TNFα drug (e.g., with the bridging assay, HACA measurements must be taken at anti-TNFα drug trough levels), and without any dependency on the multivalency of the antibody (e.g., IgG4 antibodies are not detected using the bridging assay because IgG4 antibodies are bispecific and cannot cross-link the same antigen). As such, the present invention has at least the following advantages over current methods: avoids attachment of antigens to solid surfaces (denaturation avoided); eliminates the IgG4 effect; overcomes therapeutic antibody trough issues; detects antibodies with weak affinities; eliminates non-specific binding of irrelevant IgGs; and increases the sensitivity and specificity of detection.

Figure 4:
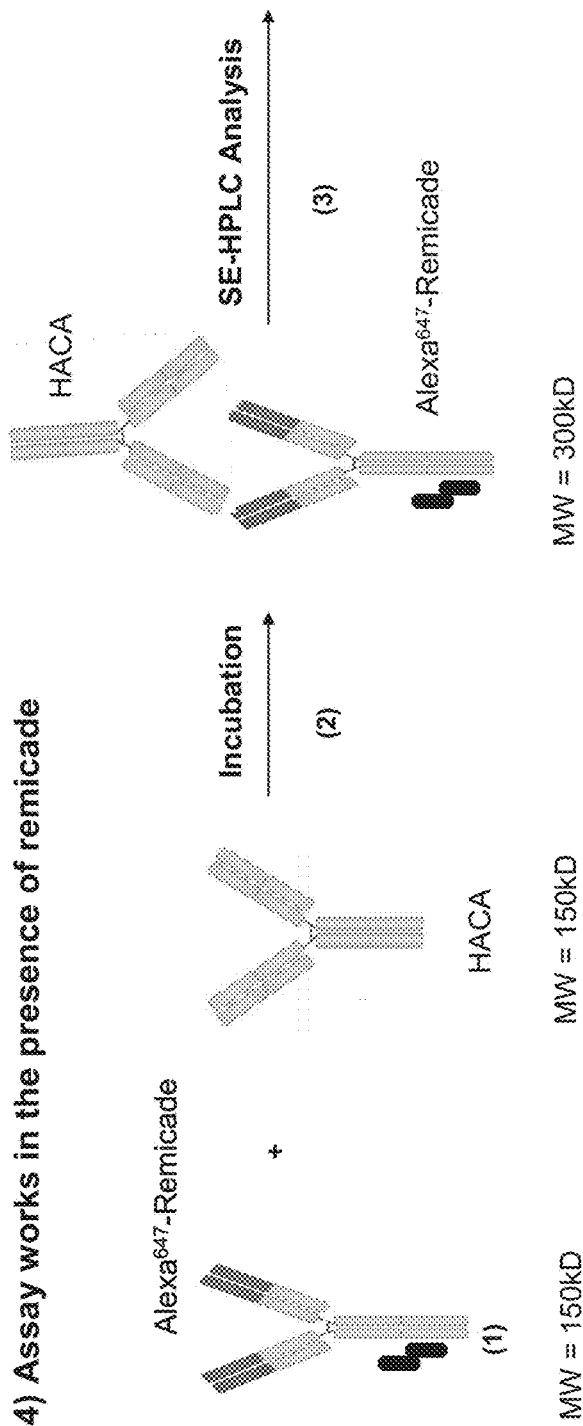
FIG. 4 illustrates an exemplary outline of the autoantibody detection assays of the present invention for measuring the concentrations of HACA/HAHA generated against REMICADE™.

In one exemplary embodiment, an anti-TNFα drug (e.g., REMICADE™) is labeled with a fluorophore (e.g., Alexa$_{647}$), wherein the fluorophore can be detected on either or both the visible and fluorescent spectra. The labeled anti-TNFα drug is incubated with human serum in a liquid phase reaction to allow HACA and HAHA present in the serum to bind. The labeled anti-TNFα drug can also be incubated with known amounts of an anti-IgG antibody in a liquid phase reaction to create a standard curve. Following incubation, the samples are loaded directly onto a size exclusion column. Binding of the autoantibodies to the labeled anti-TNFα drug results in a leftward shift of the peak compared to labeled drug alone. The concentration of HACA and HAHA present in the serum sample can then be compared to the standard curve and controls. FIG. 4 illustrates an exemplary outline of the autoantibody detection assays of the present invention for measuring the concentrations of HACA/HAHA generated against REMICADE™. In certain instances, high HACA/HAHA levels indicate that the current therapy with REMICADE™ should be switched to another anti-TNFα drug such as HUMIRA™.

The principle of this assay is based on the mobility shift of the antibody bound Alexa$_{647}$-labeled REMICADE™ complex versus free Alexa$_{647}$-labeled REMICADE™ on size exclusion-high performance liquid chromatography (SE-HPLC) due to the increase in molecular weight of the complex.

The chromatography in this example was performed on an Agilent-1200 HPLC System, using a Bio-Sep 300×7.8 mm SEC-3000 column (Phenomenex) with a molecular weight fractionating range of 5,000-700,000 and a mobile phase of 1×PBS, pH 7.4, at a flow-rate of 0.5 mL/min with UV detection at 650 nm. In front of the Agilent-1200 HPLC System with a Bio-Sep 300×7.8 mm SEC-3000 column is a analytical pre-column which is a BioSep 75×7.8 mm SEC-3000. A 100 µL sample volume is loaded onto the column for each analysis.

The antibody bound Alexa$_{647}$-labeled REMICADE™ complex is formed by incubating a known amount of the antibody and Alexa$_{647}$-labeled REMICADE™ in the 1×PBS, pH 7.3, elution buffer at room temperature for 1 hour before SE-HPLC analysis.

Figure 5:
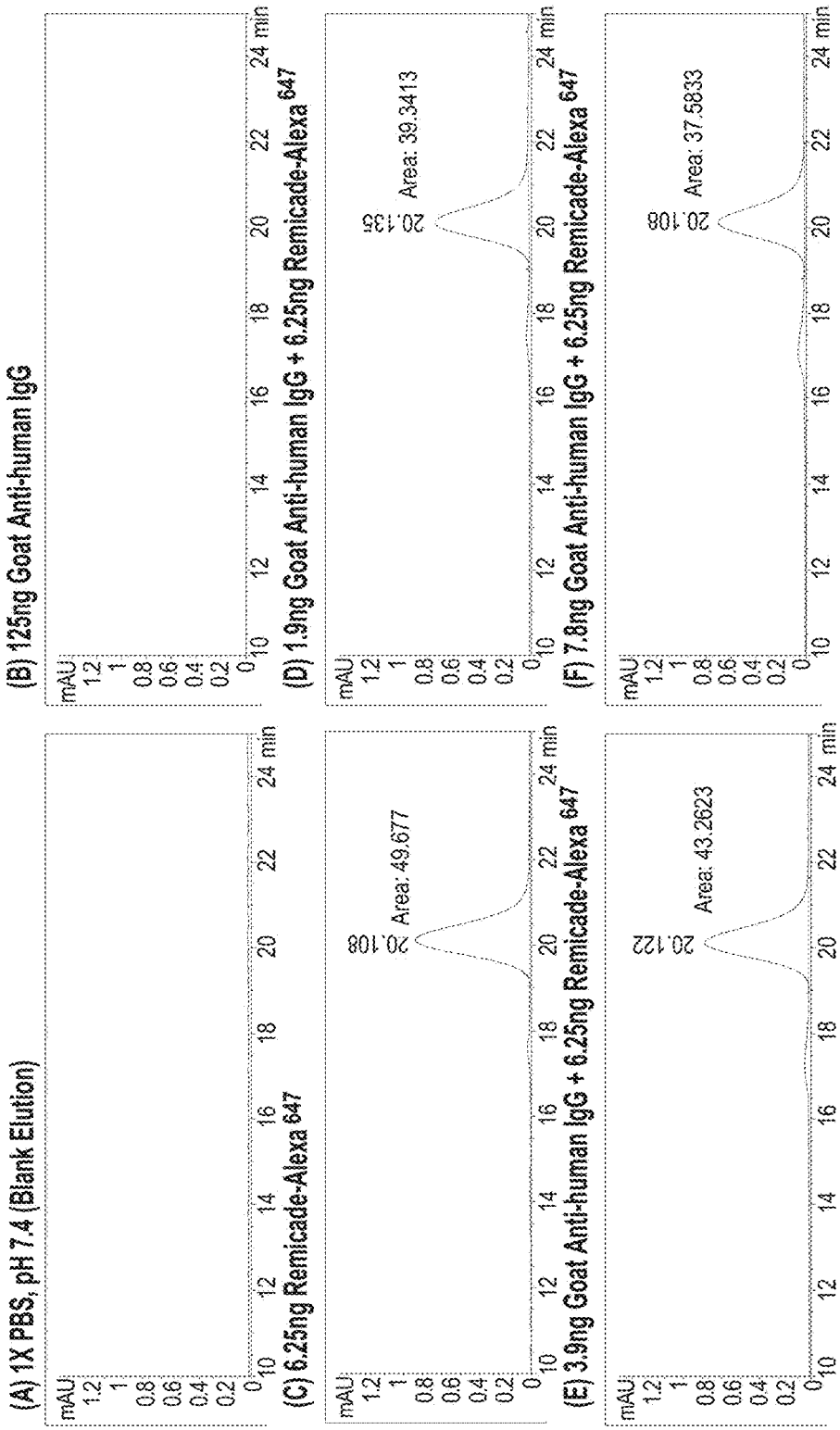
FIG. 5 shows a dose response analysis of anti-human IgG antibody binding to REMICADE™-Alexa$_{647}$.
Figure 5:
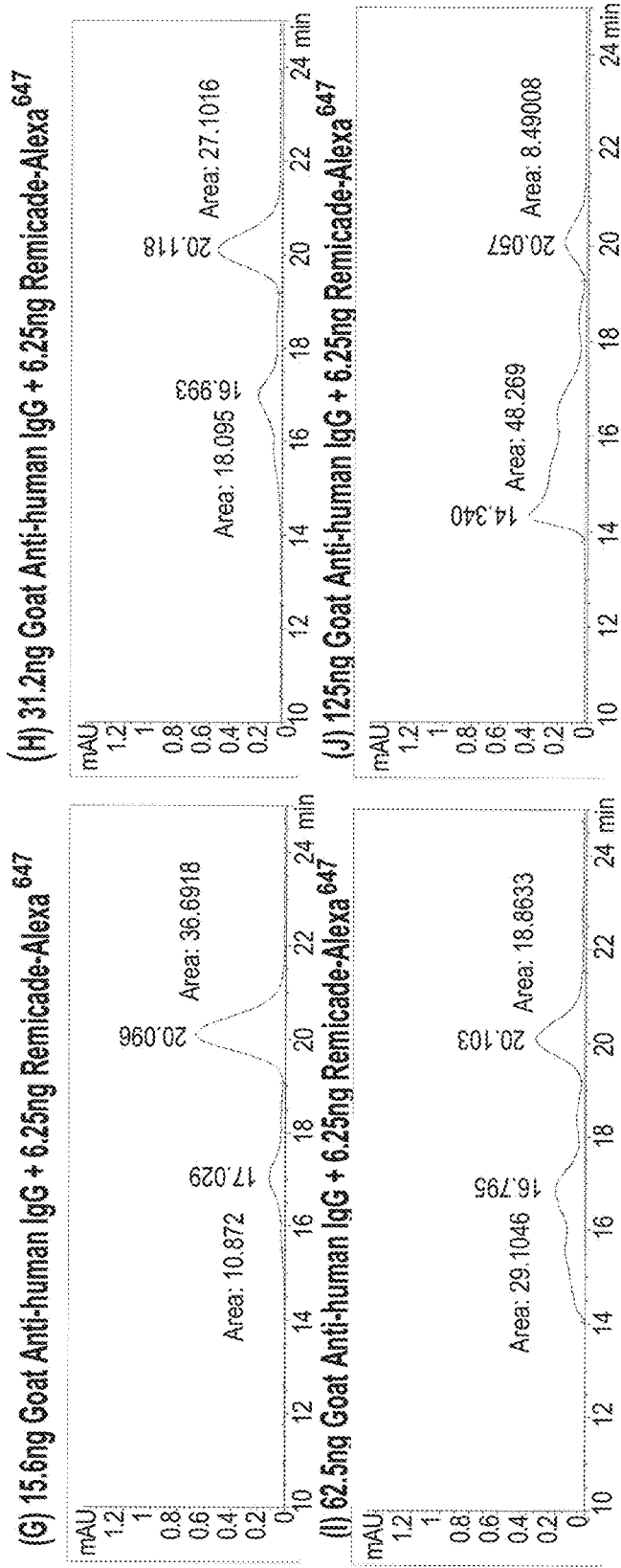
Figure 6:
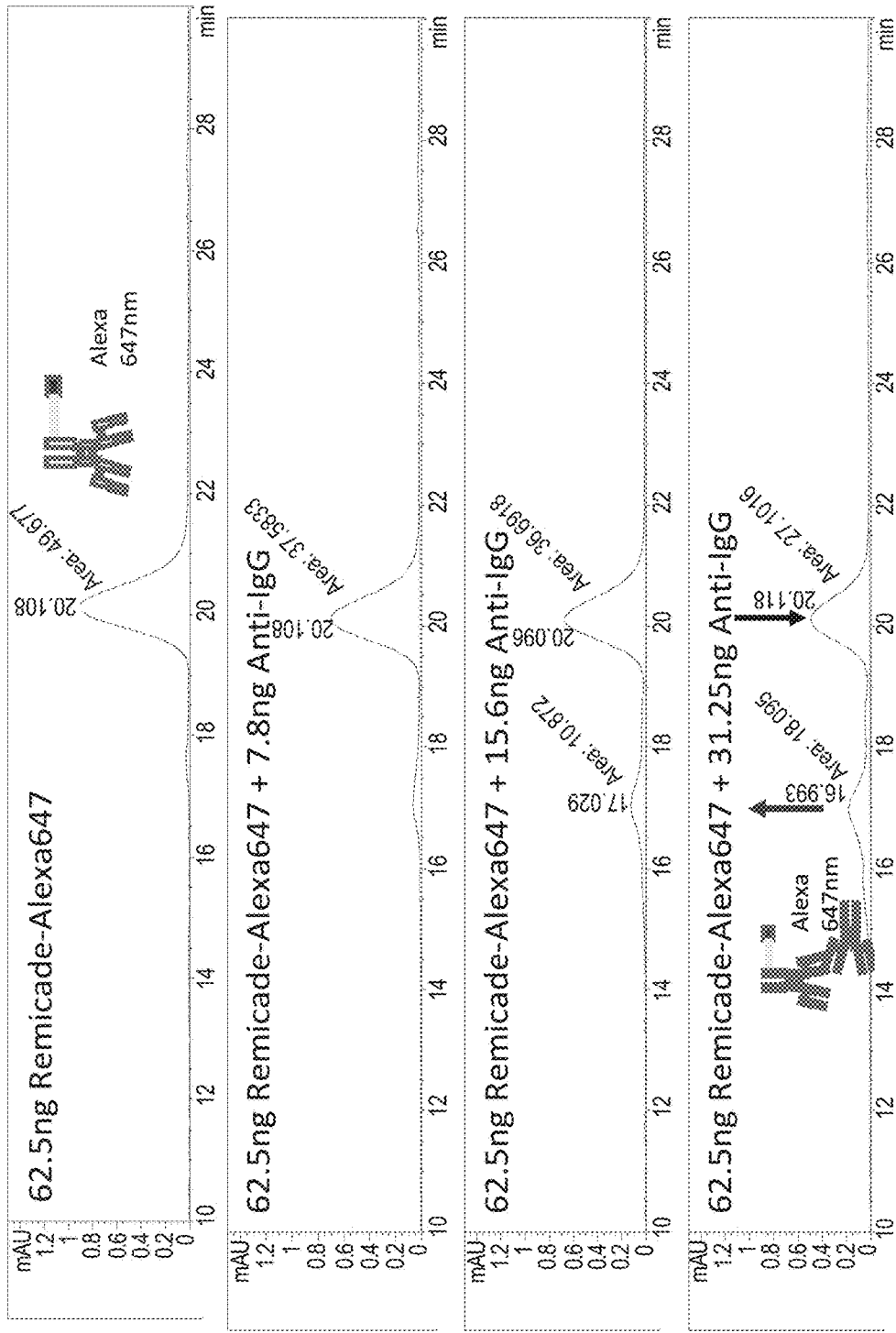
FIG. 6 shows a second dose response analysis of anti-human IgG antibody binding to REMICADE™-Alexa$_{647}$.

FIG. 5 shows a dose response analysis of anti-human IgG antibody binding to REMICADE™-Alexa$_{647}$ as detected using the size exclusion chromatography assay of the present invention. The binding of anti-IgG antibody to REMICADE™-Alexa$_{647}$ caused a shift of the REMICADE™-Alexa$_{647}$ peak to the left. FIG. 6 shows a second dose response analysis of anti-human IgG antibody binding to REMICADE™-Alexa$_{647}$ as detected using the size exclusion chromatography assay of the present invention. Higher amounts of anti-IgG antibody resulted in a dose-dependent increase in the formation of anti-IgG/REMICADE™-Alexa$_{647}$ complexes, as indicated by a shift of the REMICADE™-Alexa$_{647}$ peak to the left. FIG. 7 shows dose response curves of anti-IgG antibody binding to REMICADE™-Alexa$_{647}$.

Figure 8:
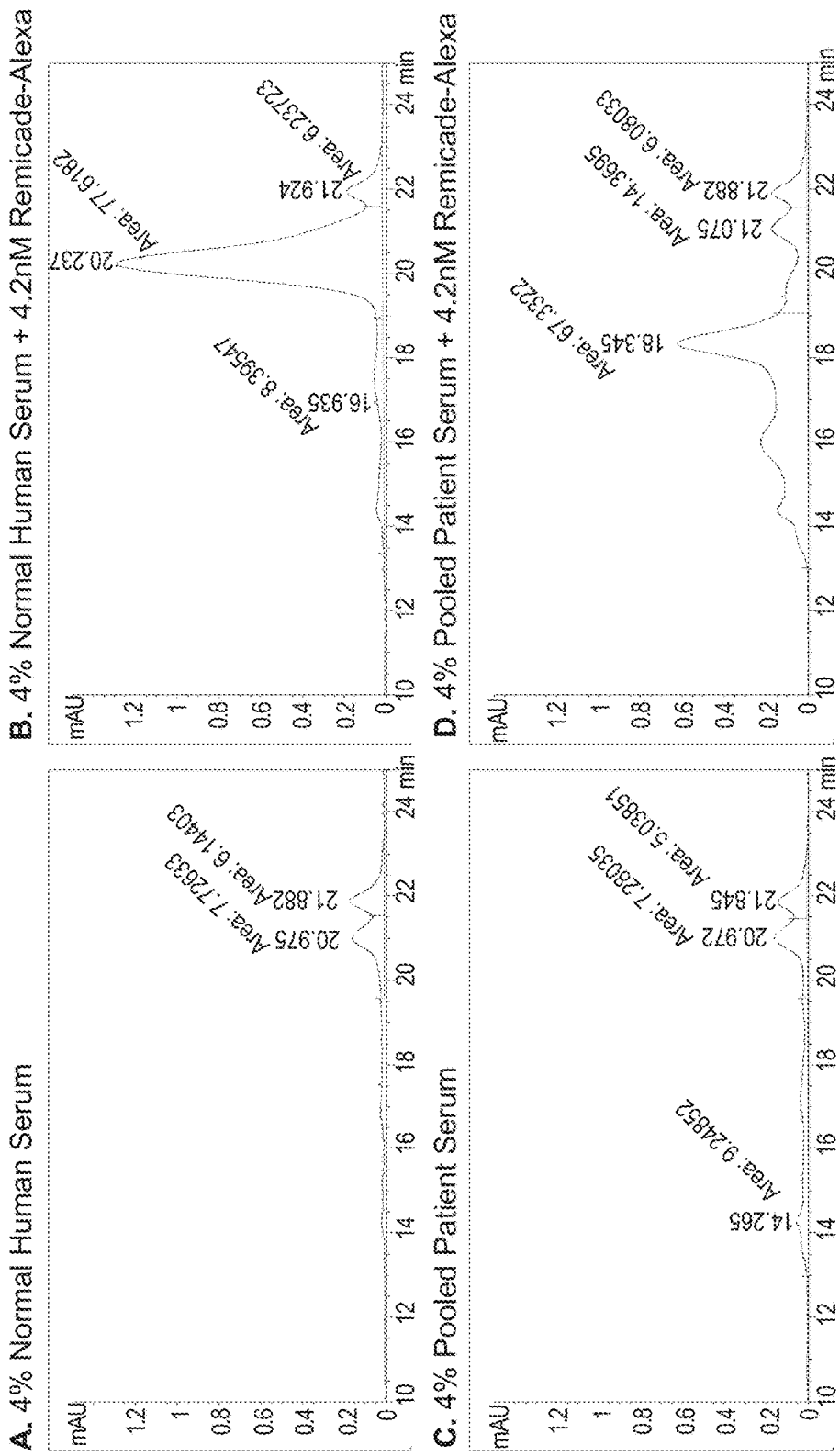
FIG. 8 shows REMICADE™-Alexa$_{647}$ immunocomplex formation in normal human serum and HACA positive serum.

FIG. 8 shows REMICADE™-Alexa$_{647}$ immunocomplex formation in normal human serum and HACA positive serum as detected using the size exclusion chromatography assay of the present invention with 100 µl of injected sample. As shown in FIG. 8, the binding of HACA present in patient samples to REMICADE™-Alexa$_{647}$ caused a shift of the REMICADE™-Alexa$_{647}$ peak to the left. As such, the size exclusion chromatography assay of the invention is particularly advantageous because it measures HACA in the presence of REMICADE™, can be utilized while the patient is on therapy, measures both weak and strong HACA binding, is a mix and read mobility shift assay, and can be extended to other approaches which use labeled REMICADE™ to equilibrate with HACA and REMICADE™

FIG. 9 provides a summary of HACA measurements from 20 patient serum samples that were performed using the bridging assay or the mobility shift assay of the present invention. This comparative study demonstrates that the present methods have increased sensitivity over current methods because 3 samples that were negative for HACA as measured using the bridging assay were actually HACA positive when measured using the mobility shift assay of the present invention (see, Patient # SK07070305, SK07070595, and SK07110035).

As such, this example demonstrates the utility of the present invention in monitoring patients receiving an anti-TNFα drug (e.g., REMICADE™) to detect the presence or level of autoantibodies (e.g., HACA and/or HAHA) against the drug, because such immune responses can be associated with hypersensitive reactions and dramatic changes in pharmacokinetics and biodistribution of the anti-TNFα drug that preclude further treatment with the drug.

In conclusion, Examples 1 and 2 demonstrate that TNFα and anti-TNFα antibodies can be efficiently labeled with Alexa$_{647}$. When labeled TNFα-Alexa$_{647}$ was incubated with anti-TNFα antibodies, the retention time of the labeled TNFα/anti-TNFα drug complex was shifted, and the amount of anti-TNFα drug that caused the shift could be quantitated with HPLC. Furthermore, when labeled anti-TNFα drug was incubated with anti-human IgG antibody, the retention time of the labeled anti-TNFα drug/anti-IgG antibody complex was shifted, and the amount of anti-IgG antibody that caused the shift could be quantitated with HPLC. Moreover, low serum content in the assay system was shown to have little effect on HPLC analysis. Finally, a standard curve could be generated for the anti-TNFα drug and HACA/HAHA assays and could be used to quantitate patient serum anti-TNFα drug or HACA/HAHA levels. Advantageously, the present invention provides in certain aspects a mobility shift assay, such as a homogeneous mix and read assay developed to measure both drug and antibodies against the drug. A standard curve was generated for the anti-TNFα biologic REMICADE™ and HUMIRA and also for the HACA antibodies against REMICADE™. The mobility shift assay format, unlike ELISA, eliminates coating of antigens to solid surface and is not affected by non-specific binding of irrelevant IgGs. The assay format is simple, but very sensitive and can be used to detect all anti-TNFα biologic drugs (e.g., REMICAD™, HUMIRA, Enbrel and Cimzia) as well as the neutralizing antibody (anti-REMICADE™) in patient serum.

Example 3. Measurement of Human Anti-Chimeric Antibodies (HACA) and Infliximab (IFX) Levels in Patient Serum Using a Novel Mobility Shift Assay Abstract Background:

Infliximab (IFX) is a chimeric monoclonal antibody therapeutic against TNFα that has been shown to be effective in treating autoimmune diseases such as rheumatoid arthritis (RA) and inflammatory bowel disease (IBD). However, antibodies against IFX were found in some IFX-treated patients through the detection of human anti-chimeric antibodies (HACA), which may reduce the drug's efficacy or induce adverse effects. Monitoring of HACA and IFX levels in individual patients may help to optimize the dosing and treatment with IFX. Current methods for detecting HACA are based on solid-phase assays, which are limited by the fact that the presence of IFX in the circulation may mask the presence of HACA and, therefore, measurement can only be done at least 8 weeks following a dose of IFX. Moreover, this time-lapse further confounds the assays because of the rapid clearance of the high molecular weight immune complexes in the blood circulation. To overcome these drawbacks, we have developed and evaluated a new method to measure serum IFX and HACA levels in patients treated with IFX.

Methods:

A novel non-radiolabeled, liquid-phase, size-exclusion (SE)-HPLC mobility shift assay was developed to measure the HACA and IFX levels in serum from patients treated with IFX. The immuno-complex (e.g., TNFα/IFX or IFX/HACA), free TNFα or IFX, and the ratio of bound/free can be resolved and calculated with high sensitivity. Serum concentrations of IFX or HACA were determined with standard curves generated by incubating with different concentrations of IFX or pooled HACA-positive serum. Using this novel assay, we have measured IFX and HACA levels in sera collected from IBD patients treated with IFX who had relapsed and compared the results with those obtained by the traditional Bridge ELISA assay.

Results:

Dose-response curves were generated from the novel assay with high sensitivity. Detection of HACA was demonstrated in the presence of excess IFX. In the 117 serum samples from patients treated with IFX, 65 samples were found to have IFX levels above the detection limit and the average was 11.0+6.9 mg/mL. For HACA levels, 33 (28.2%) samples were found to be positive while the Bridge ELISA assay detected only 24 positive samples. We also identified 9 false negatives and 9 false positives from the samples determined by the Bridge assay. HACA levels were found to be increased in 11 patients during the course of IFX treatment while the IFX levels were found to be significantly decreased.

Conclusions:

A novel non-radiolabeled, liquid-phase, mobility shift assay has been developed to measure the IFX and HACA levels in serum from patients treated with IFX. The assay has high sensitivity and accuracy, and the obtained results were reproducible. This novel assay can advantageously be used to measure HACA and IFX levels while patients are on therapy.

Introduction

Tumor necrosis factor-alpha (TNFα) plays a pivotal role in the pathogenesis of autoimmune diseases such as Crohn's disease (CD) and rheumatoid arthritis (RA). It is well documented that blocking TNFα with therapeutic antibodies such as Infliximab (human-murine chimeric monoclonal IgG1K) or adalimumab (fully human monoclonal antibody) reduces disease activity in CD and RA. However, about 30-40% of the patients do not respond to anti-TNFα therapy and some patients need higher doses or dosing frequency adjustments due to lack of sufficient response. Differences of drug bioavailability and pharmacokinetics in individual patients may contribute to the failure of the treatment. Immunogenicity of the drugs, which causes patients to develop HACA/HAHA, could result in a range of adverse reactions from mild allergic response to anaphylactic shock. These problems are now recognized by many investigators, drug-controlling agencies, health insurance companies, and drug manufacturers. Furthermore, many patients with secondary response failure to one anti-TNFα drug benefit from a switch to other anti-TNFα drugs, suggesting a role of neutralizing antibodies directed specifically against the protein used for treatment (Radstake et al., *Ann. Rheum. Dis.*, 68(11): 1739-45 (2009)). Monitoring of patients for drug and HACA/HAHA levels is therefore warranted so that drug administration can be tailored to the individual patient and prolonged therapies can be given effectively and economically with little or no risk to patients (Bendtzen et al., *Scand. J. Gastroenterol.*, 44(7):774-81 (2009)).

Several enzyme-linked immunoassays have been used to assess the circulating levels of drugs and HACA/HAHA. FIG. 10 provides a summary of the current assays available for the measurement of HACA in comparison to the novel HACA assay of the present invention. One of the limitations of current methodologies is that antibody levels are difficult to measure when there is a measurable amount of drug in the circulation. In contrast to current solid-phase methods for detecting HACA in which measurements can only be performed at least 8 weeks following a dose of IFX, the novel assay of the present invention is a non-radiolabeled, liquid-phase, size-exclusion (SE)-HPLC assay that is capable of measuring HACA and IFX levels in serum from patients while being treated with IFX.

The following are rationales for measuring the serum concentrations of anti-TNFα biologic drugs and antibodies against TNFα biologic drugs in patients: (1) for PK studies in clinical trials; (2) it may be required by the FDA during clinical trials to monitor a patient's immune response to the biologic drug; (3) to monitor a patient's response to the biologic drug by measuring HACA or HAHA to guide the drug dosage for each patient; and (4) for use as a guide for switching to a different biologic drug when the initial drug fails.

Methods

SE-HPLC Analysis of Infliximab (IFX) Levels in Patient Serum.

Human recombinant TNFα was labeled with a fluorophore ("Fl" such as, e.g., Alexa Fluor® 488) according to the manufacture's instructions. Labeled TNFα was incubated with different amounts of IFX or patient serum for one hour at room temperature. Samples of 100 µL volume were analyzed by size-exclusion chromatography on an HPLC system. FLD was used to monitor the free TNFα-Fl and the bound TNFα-Fl immuno-complex based on their retention times. Serum IFX levels were calculated from the standard curve.

SE-HPLC Analysis of HACA Levels in Patient Serum.

Purified IFX was labeled with Fl. Labeled IFX was incubated with different dilutions of pooled HACA-positive serum or diluted patient serum for one hour at room temperature. Samples of 100 µL volume were analyzed by size-exclusion chromatography on an HPLC system. FLD was used to monitor the free IFX-Fl and the bound IFX-Fl immuno-complex based on their retention times. The ratio of bound and free IFX-Fl was used to determine the HACA level.

Mobility Shift Assay Procedure to Measure HACA in Serum.

The principle of this assay is based on the mobility shift of the HACA bound Fl-labeled Infliximab (IFX) complex versus free Fl-labeled IFX on size exclusion-high performance liquid chromatography (SE-HPLC) due to the increase in molecular weight of the complex. The chromatography is performed in an Agilent-1200 HPLC System, using a Bio-Sep 300×7.8 mm SEC-3000 column (Phenomenex) with a molecular weight fractionating range of 5,000-700,000 and a mobile phase of 1×PBS, pH 7.3, at a flow-rate of 0.5 mL/min with FLD detection. In front of the Agilent-1200 HPLC System with a Bio-Sep 300×7.8 mm SEC-3000 column is a analytical pre-column which is a BioSep 75×7.8 mm SEC-3000. A 100 µL sample volume is loaded onto the column for each analysis. The HACA bound Fl-labeled IFX complex is formed by incubating serum from IFX treated patient and Fl-labeled IFX in the 1×PBS, pH 7.3, elution buffer at room temperature for 1 hour before SE-HPLC analysis.

Results

Figure 11:
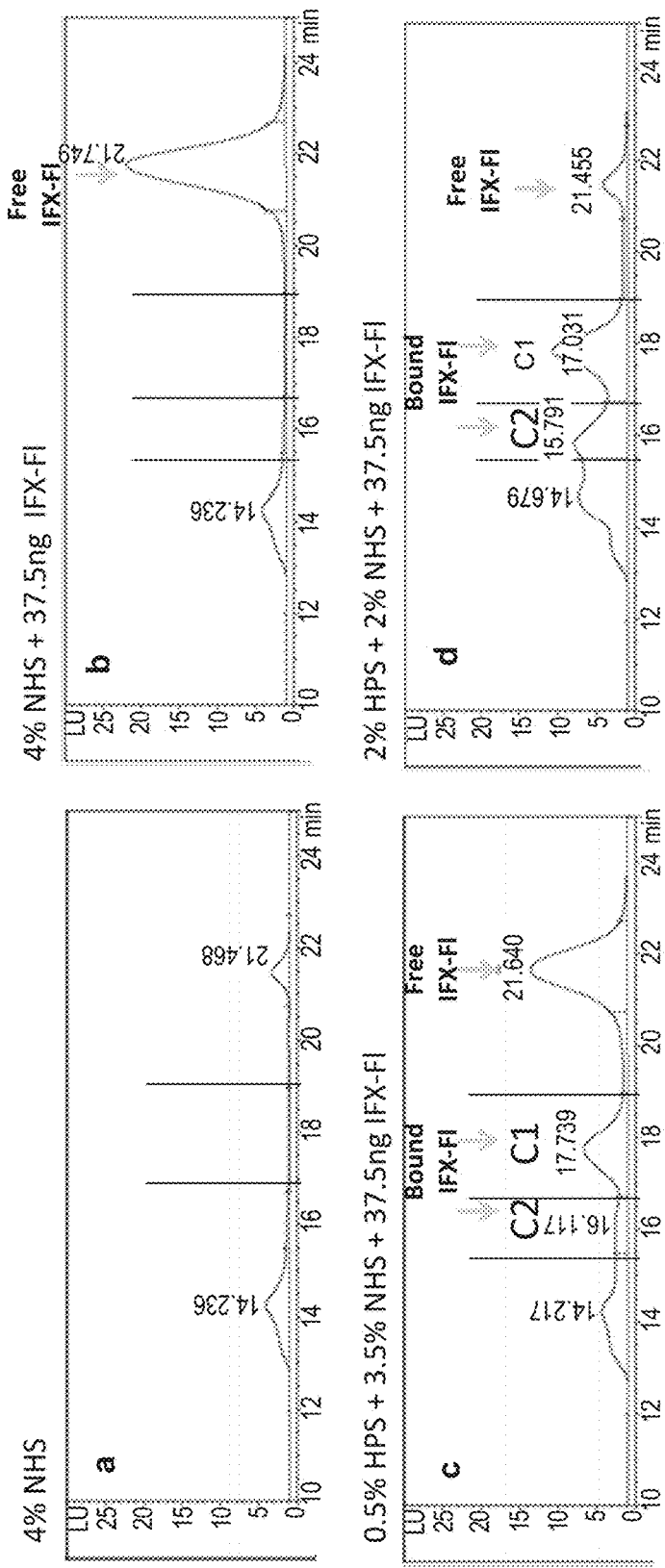
FIG. 11 shows SE-HPLC profiles of fluorophore (Fl)-labeled IFX incubated with normal (NHS) or HACA-positive (HPS) serum. The addition of increasing amounts of HACA-positive serum to the incubation mixture dose-dependently shifted the IFX-Fl peak to the higher molecular mass eluting positions, C1 and C2.
Figure 12:
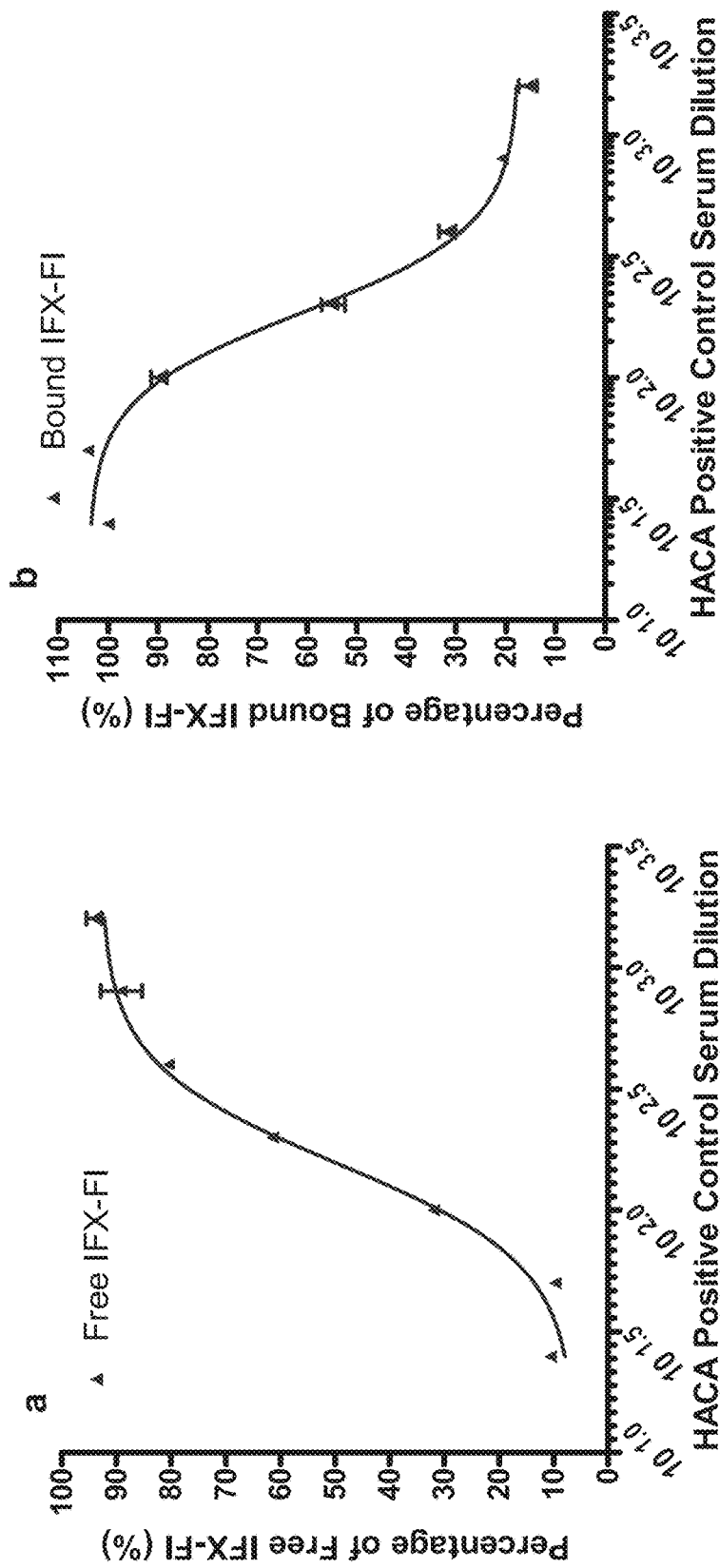
FIG. 12 shows dose-response curves of the bound and free IFX-Fl generated with increasing dilutions of HACA-positive serum as determined by the mobility shift assay. (A) Increasing dilutions of HACA-positive serum were incubated with 37.5 ng of IFX-Fl. The higher the dilution (less HACA) the more free IFX-Fl was found in the SE-HPLC analysis. (B) Increasing dilutions of HACA-positive serum were incubated with 37.5 ng of IFX-Fl. The higher the dilution (less HACA) the less HACA bound IFX-Fl was found in the SE-HPLC analysis.

FIG. 11 shows the separation of the HACA bound IFX-Fl complex from the free IFX-Fl due to the mobility shift of the high molecular weight complex. As seen in panels c and d, the retention time of the fluorescent peak shifted from 21.8 min to 15.5-19.0 min. The more the HACA is present in the reaction mixture, the less the free IFX-Fl remains in the chromatogram and the more the immuno-complex is formed. FIG. 12 shows the dose-response curves of the fluorescent peak shift caused by the addition of HACA. Using the HACA positive sample, we could detect the peak shift with 1:1000 dilutions of the serum.

Figure 13:
FIG. 13 shows SE-HPLC profiles of TNFα-Fl incubated with normal (NHS) or IFX-spiked serum. The addition of increasing amounts of IFX-spiked serum to the incubation mixture dose-dependently shifted the fluorescent TNFα peak to the higher molecular mass eluting positions.
Figure 14:
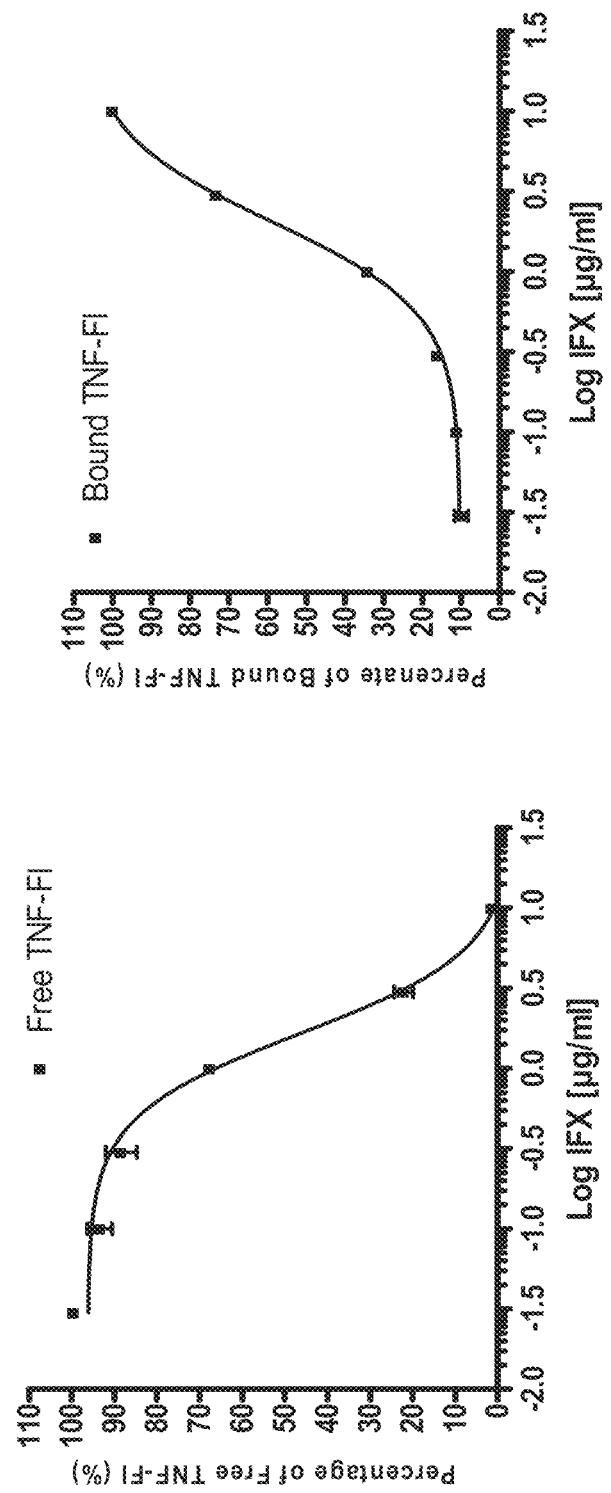
FIG. 14 shows dose-response curves of the bound and free TNFα generated with increasing dilutions of IFX-spiked serum as determined by the mobility shift assay. Increasing concentrations of IFX added to the incubation mixture decreases the percentage of free TNFα while increasing the percentage of bound TNFα.

FIG. 13 shows the separation of the IFX bound TNFα-Fl complex from the free TNFα-Fl due to the mobility shift of the high molecular weight complex. As seen in panels c and d, the retention time of the fluorescent peak shifted from 24 min to 13-19.5 min. The more the IFX is present in the reaction mixture, the less the free TNFα-Fl remains in the chromatogram and the more the immuno-complex is formed. FIG. 14 shows the dose-response curves of the TNFα-Fl peak shift caused by the addition of IFX. Based on the added IFX, the detection limit is 10 ng/mL of IFX in serum.

The novel mobility shift assay of the present invention was validated by testing serum samples from HACA positive and negative patients measured by the Bridge assay (Table 2). Using this assay, we have analyzed serum samples from 50 healthy subjects and 117 IBD patients treated with IFX. All 50 healthy subject samples have an IFX level below the limit of detection, whereas 65 of the patient samples have an average IFX concentration of 11.0 µg/ml. Table 3 shows the HACA levels in the serum of healthy controls and IBD patients treated with IFX measured by the Bridge assay and the mobility shift assay. The Bridge assay detected less HACA-positive patients than the mobility shift assay and more false negatives as well as more false positives.

TABLE 2

Correlation of Relative HACA Levels in Patient Serum from Strong Positive and Negative on Bridge Assay to SE-HPLC Assay.

|  | Bridge assay | HPLC shift assay | Correlation |
| --- | --- | --- | --- |
| Positive | 82 | 81 | 99% |
| Negative | 12 | 12 | 100% |

TABLE 3

Patient Sample Analysis on Serum Levels of HACA with
Bridge Assay (Cut Off 1.69 µg/ml) and HPLC Shift
Assay (Cut Off 0.19, Ratio of Bound and Free IFX).

|  | | HACA Positive | | Bridge Assay | |
| --- | --- | --- | --- | --- | --- |
|  | Subjects (n) | Bridge Assay | HPLC Assay | False Negative | False Positive |
| Healthy Control | 50 | N/A | 0 | N/A | N/A |
| Patient treated with IFX | 117 | 24 (20.5%) | 33 (28.2%) | 9 (High IFX) | 9 |

False negative results are caused by patient serum containing high levels of IFX which interferes with the Bridge assay on HACA determination while the SE-HPLC assay is not affected. False positive results are caused by patient serum containing high levels of non-specific interference substance which may interfere with the Bridge assay.

Figure 15:
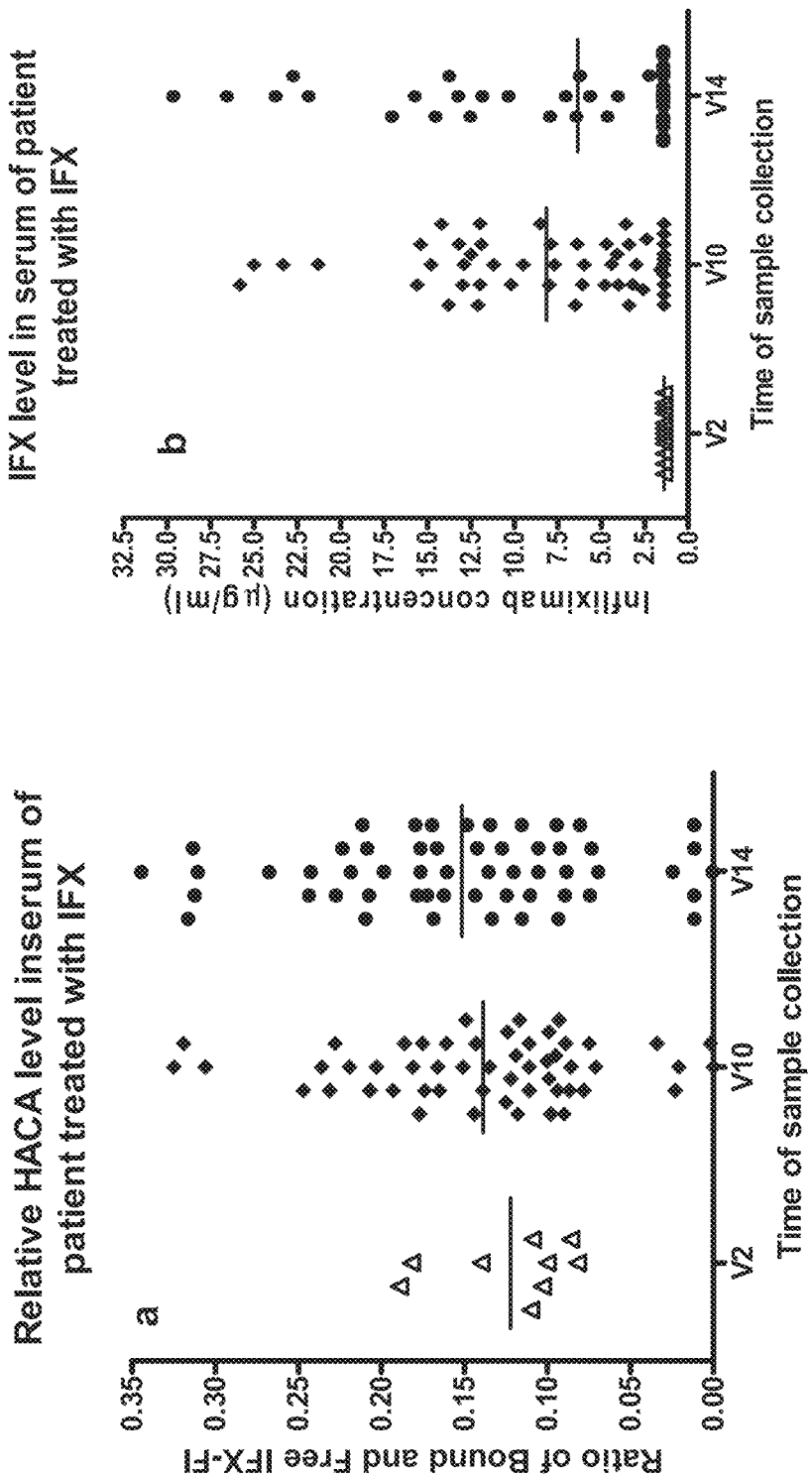
FIG. 15 shows the measurement of relative HACA level and IFX concentration in IBD patients treated with IFX at different time points by the mobility shift assay.
Figure 16:
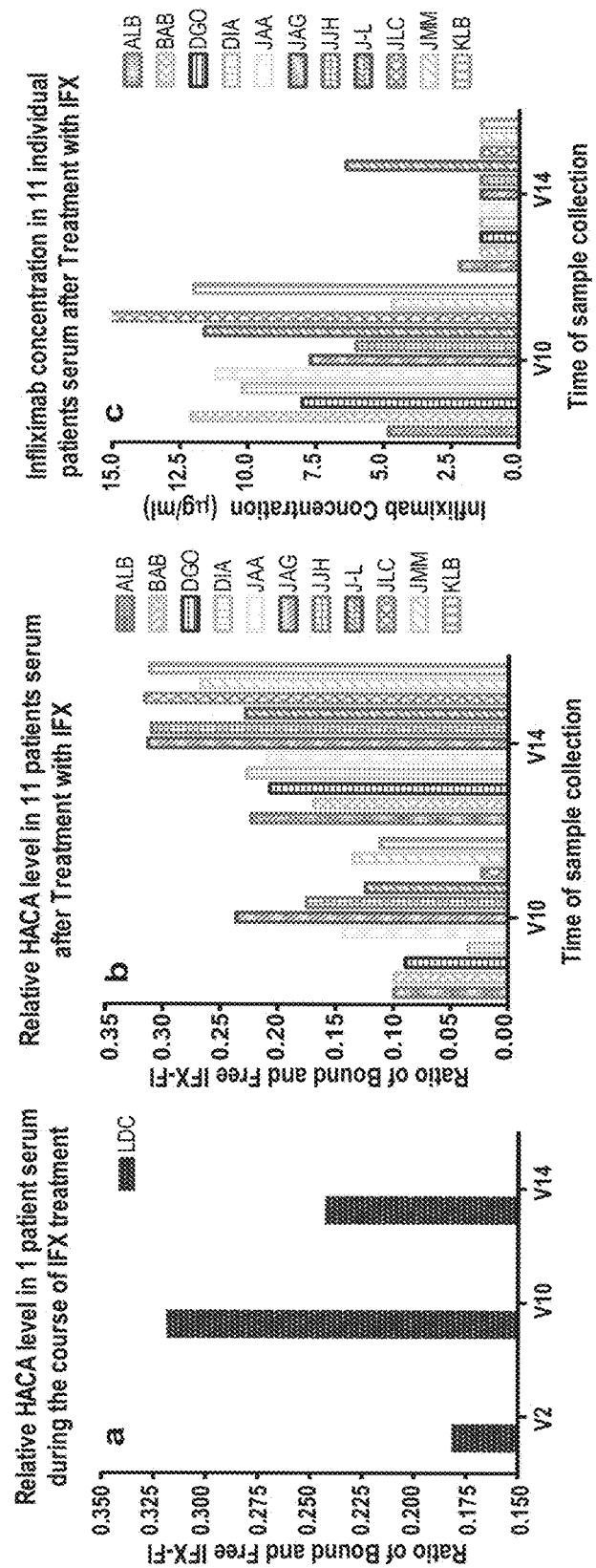
FIG. 16 shows patient management-measurement of HACA level and IFX concentration in the sera of IBD patients treated with IFX at different time points.

FIG. 15 shows the relationship of the HACA level and IFX concentration in IBD patients during the course of IFX treatment. HACA could be detected as early as V10 (30 Weeks) and continued to increase in some patients during IFX treatment. FIG. 16 shows that HACA can be detected in the presence of IFX using the assay of the present invention. A higher level of HACA in the serum was associated with a lower level of IFX that could be detected (e.g., reduced bioavailability). As such, early detection of HACA while on treatment with IFX can guide the physician and/or patient to switch to other anti-TNF drugs or increase the dose of IFX.

Conclusion

Anti-TNFα biologic drugs can be readily labeled with a fluorophore ("Fl") and the mobility shift assay format used for measuring HACA/HAHA is a homogeneous assay without the coating of antigens to a solid surface and multiple washing and incubation steps like a typical ELISA. Incubation of Fl-labeled IFX with HACA-positive serum results in the formation of an immune complex which elutes at a different position compared to free Fl-labeled IFX in SE-HPLC and thus the amount of HACA can be quantitated. The presence of other serum components has little effect on the mobility shift assay. The mobility shift assay format, unlike ELISA, is not affected by non-specific binding of irrelevant IgGs and detects the IgG4 isotype. Healthy serum samples do not cause mobility shift of the Fl-labeled IFX and 28.2% of the patients treated with IFX were found to have HACA by the assay of the present invention. As such, the assay format described herein is very sensitive and can be applied to detect all biologic drugs (e.g., REMICADE™, HUMIRA, Enbrel and Cimzia) as well as their antibodies (e.g., anti-REMICADE™, anti-HUMIRA, anti-Enbrel and anti-Cimzia) in patient serum. Notably, since HACA can be detected in the presence of IFX using the mobility shift assay of the invention, early detection of HACA while on treatment with IFX can guide the physician and/or patient to switch to other anti-TNF drugs or increase the subsequent dose of IFX.

We have developed a novel non-radiolabeled, liquid-phase, SE-HPLC assay to measure the IFX and HACA levels in serum samples obtained from patients treated with IFX. The novel assay has high sensitivity, accuracy, and precision, and the results are highly reproducible, which makes this assay suitable for routine testing of a large number of human serum samples. The new assay format, unlike ELISA, eliminates coating of antigens to solid surfaces and is not affected by non-specific binding of irrelevant IgGs. These advantages of the assay format described herein reduce the false negative and false positive results of the test. Advantageously, the assay format of the present invention is very sensitive and can be used to detect all biologic drugs as well as their antibodies present in the serum while the patient is on therapy.

Example 4. Differentiation Between Neutralizing and Non-Neutralizing Human Anti-Chimeric Antibodies (HACA) in Patient Serum Using Novel Mobility Shift Assays This example illustrates novel homogeneous assays for measuring autoantibody (e.g., HACA) concentrations in a patient sample (e.g., serum) and for determining whether such autoantibodies are neutralizing or non-neutralizing autoantibodies using size exclusion chromatography to detect the binding of these autoantibodies to fluorescently labeled anti-TNFα drug in the presence of fluorescently labeled TNFα. These assays are advantageous because they obviate the need for wash steps which remove low affinity HACA, use distinct fluorophores that allow for detection on the visible and/or fluorescent spectra which decreases background and serum interference issues, increase the ability to detect neutralizing or non-neutralizing HACA in patients with a low titer due to the high sensitivity of fluorescent label detection, and occur as a liquid phase reaction, thereby reducing the chance of any changes in the epitope by attachment to a solid surface such as an ELISA plate.

In one exemplary embodiment, an anti-TNFα drug (e.g., REMICADE™) is labeled with a fluorophore "F1" (see, e.g., FIG. 17A), wherein the fluorophore can be detected on either or both the visible and fluorescent spectra. Similarly, TNFα is labeled with a fluorophore "F2" (see, e.g., FIG. 17A), wherein the fluorophore can also be detected on either or both the visible and fluorescent spectra, and wherein "F1" and "F2" are different fluorophores. The labeled anti-TNFα drug is incubated with human serum in a liquid phase reaction and the labeled TNFα is added to the reaction to allow the formation of complexes (i.e., immuno-complexes) between the labeled anti-TNFα drug, labeled TNFα, and/or HACA present in the serum. Following incubation, the samples are loaded directly onto a size exclusion column. Binding of both the autoantibody (e.g., HACA) and the labeled TNFα to the labeled anti-TNFα drug results in a leftward shift of the peak (e.g., "Immuno-Complex 1" in FIG. 17A) compared to a binary complex between the autoantibody and the labeled anti-TNFα drug (e.g., "Immuno-Complex 2" in FIG. 17A), the labeled drug alone, or the labeled TNFα alone. The presence of this ternary complex of autoantibody (e.g., HACA), labeled TNFα, and labeled anti-TNFα drug indicates that the autoantibody present in the serum sample is a non-neutralizing form of the autoantibody (e.g., HACA), such that the autoantibody does not interfere with the binding between the anti-TNFα drug and TNFα. In one particular embodiment, as shown in FIG. 17A, if non-neutralizing HACA is present in the serum, a shift will be observed for both F1-REMICADE™ and F2-TNFα, resulting in an increase in both the Immuno-Complex 1 and Immuno-Complex 2 peaks and a decrease in the free F1-REMICADE™ and free F2-TNFα peaks. However, the presence of the binary complex between the autoantibody (e.g., HACA) and the labeled anti-TNFα drug (e.g., "Immuno-Complex 2" in FIG. 17B) in the absence of the ternary complex of autoantibody (e.g., HACA), labeled TNFα, and labeled anti-TNFα drug indicates that the autoantibody present in the serum sample is a neutralizing form of the autoantibody (e.g., HACA), such that the autoantibody interferes with the binding between the anti-TNFα drug and TNFα. In one particular embodiment, as shown in FIG. 17B, if neutralizing HACA is present in the serum, a shift will be observed for F1-REMICADE™, resulting in an increase in the Immuno-Complex 2 peak, a decrease in the free F1-REMICADE™ peak, and no change in the free F2-TNFα peak. In certain instances, the presence of neutralizing HACA indicates that the current therapy with REMICADE™ should be switched to another anti-TNFα drug such as HUMIRA™.

Figure 18:
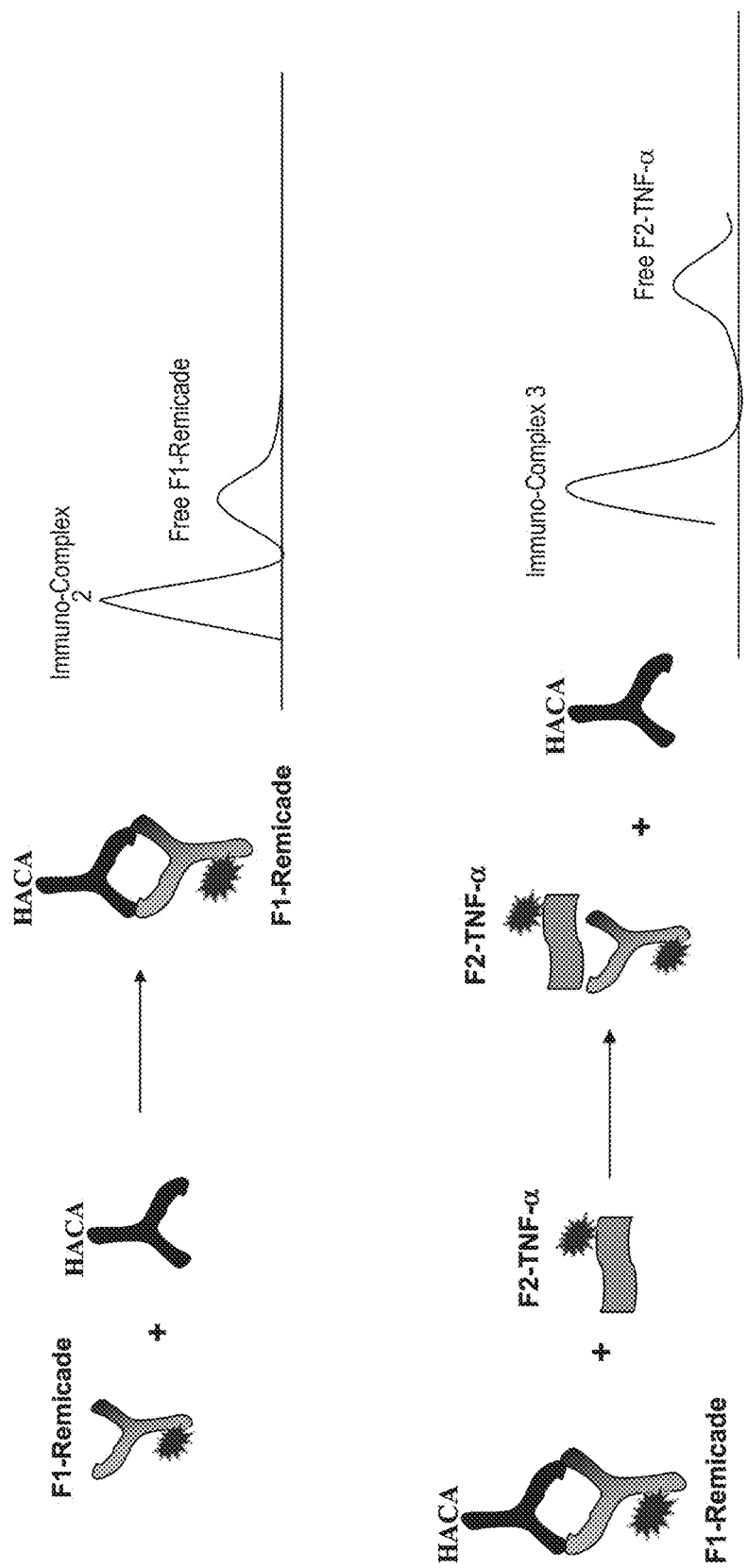
FIG. 18 shows an alternative embodiment of the assays of the present invention to detect the presence of neutralizing autoantibodies such as HACA.

In an alternative embodiment, the labeled anti-TNFα drug is first incubated with human serum in a liquid phase reaction to allow the formation of complexes (i.e., immuno-complexes) between the labeled anti-TNFα drug and HACA present in the serum. Following incubation, the samples are loaded directly onto a first size exclusion column. Binding of the autoantibody (e.g., HACA) to the labeled anti-TNFα drug results in a leftward shift of the peak (e.g., "Immuno-Complex 2" in FIG. 18) compared to the labeled drug alone. The labeled TNFα is then added to the reaction to determine whether it is capable of displacing (e.g., competing with) the autoantibody (e.g., HACA) for binding to the labeled anti-TNFα drug, to thereby allow the formation of complexes (i.e., immuno-complexes) between the labeled anti-TNFα drug and the labeled TNFα. Following incubation, the samples are loaded directly onto a second size exclusion column. Binding of the labeled anti-TNFα drug to the labeled TNFα results in a leftward shift of the peak (e.g., "Immuno-Complex 3" in FIG. 18) compared to the labeled TNFα alone. Disruption of the binding between the autoantibody (e.g., HACA) and the labeled anti-TNFα drug by the addition of the labeled TNFα indicates that the autoantibody present in the serum sample is a neutralizing form of the autoantibody (e.g., HACA), such that the autoantibody interferes with the binding between the anti-TNFα drug and TNFα. In certain instances, the presence of neutralizing HACA indicates that the current therapy with REMICADE™ should be switched to another anti-TNFα drug such as HUMIRA™.

Example 5. Analysis of Human Anti-Drug Antibodies (ADA) to Adalimumab in Patient Serum Using a Novel Homogeneous Mobility Shift Assay Background and Aim:

Monoclonal antibodies against TNF-α such as infliximab (IFX), adalimumab (HUMIRA™), and certolizumab have been shown to be effective in treating inflammatory bowel disease (IBD) and other inflammatory disorders. Anti-drug antibodies (ADA) may reduce the drug's efficacy and/or induce adverse effects. However, ADAs have been found not only in patients treated with the chimeric antibody infliximab, but also in patients treated with the humanized antibody adalimumab. Monitoring of ADA and drug levels in individual patients may help optimize treatment and dosing of the patient. We have developed a non-radio labeled liquid-phase homogeneous mobility shift assay to accurately measure in the serum both HACA (Human Anti-Chimeric Antibody) and IFX from patients. This assay method overcomes a major limitation of the current solid-phase assays for detecting HACA, namely the inability to accurately detect HACA in the presence of IFX in circulation. In the present study, we have evaluated this new method for measuring serum ADA and drug levels in patients treated with the humanized antibody drug, adalimumab.

Methods:

The mobility shift assay was based on the shift in retention time of a free antigen versus antigen-antibody immunocomplex on size-exclusion separation. Fluorophore-labeled adalimumab or TNF-α and internal control were mixed with serum samples to measure the mobility shift of free adalimumab and TNF-α in the presence of ADA or drug. The changes in the ratio of free adalimumab or TNF-α to internal control are indicators of immunocomplex formation. Serum concentrations of ADA or adalimumab were determined with standard curves generated by incubating with different concentrations of anti-human IgG antibody or purified adalimumab. Using the mobility shift assay, we measured adalimumab and ADA levels in sera collected from IBD patients treated with adalimumab who had lost response.

Results:

Dose-response curves were generated with anti-human IgG antibody for the measurement of mobility shift of labeled adalimumab. The detection limit of the assay was 1 ng of anti-human IgG. Sera from fifty healthy controls were tested for ADA and all of the samples had ADA levels below the detection limit (i.e., no shift of the free labeled-adalimumab). Detection of ADA was also demonstrated in the presence of exogenously added adalimumab. To measure the drug concentration in patients treated with adalimumab, we generated a standard curve with different amounts of adalimumab on the mobility shift of labeled TNF-α, and the detection limit of adalimumab was 10 ng.

Conclusions:

The non-radio labeled liquid-phase homogeneous mobility shift assay of the present invention has been applied to measure ADA and adalimumab levels in serum samples from patients treated with adalimumab. The assay is found to be reproducible with high sensitivity and accuracy, and can be used to evaluate ADA levels in serum samples from patients treated with adalimumab.

Example 6. Analysis of Anti-Drug Antibodies (ADA) to Adalimumab in Patient Serum Using a Novel Proprietary Mobility Shift Assay Abstract Background:

Anti-TNF-α drugs such as infliximab (IFX) and adalimumab (ADL) have been shown to be effective in treating inflammatory bowel disease (IBD). However, induction of ADA in the treated patients may reduce the drug's efficacy and/or induce adverse effects. Indeed, ADAs have been found not only in patients treated with IFX, but also in patients treated with ADL. Monitoring of ADA and drug levels in individual patients may help to optimize treatment and dosing of the patient. We have developed a proprietary mobility shift assay to accurately measure in the serum both HACA (Human Anti-Chimeric Antibody) and IFX from IFX-treated patients. This assay overcomes the major limitation of the current solid-phase assays for detecting HACA, namely the inability to accurately detect HACA in the presence of IFX in circulation. In the present study, we have evaluated this new assay to measure serum ADA and drug levels in patients treated with the fully human antibody drug, ADL.

Methods:

The mobility shift assay was based on the shift in retention time of the antigen-antibody immunocomplex versus free antigen on size-exclusion chromatography. Fluorophore-labeled ADL or TNF-α and internal control were mixed with serum samples to measure the mobility shift of labeled ADL and TNF-α in the presence of ADA or drug. The changes in the ratio of free ADL or TNF-α to internal control are the indicators of the immunocomplex formation.

Serum concentrations of ADA or ADL were determined with standard curves generated by incubating with different concentrations of anti-human IgG antibody or purified ADL. Using this assay, we measured ADL and ADA levels in sera collected from IBD patients treated with ADL.

Results:

Dose-response curves were generated with anti-human IgG antibody for the measurement of mobility shift of labeled ADL. The detection limit of the assay was 10 ng of anti-human IgG. Sera from 100 healthy controls were tested for the ADA and all of the samples had an ADA level below detection limit (no shift of free labeled ADL). Detection of ADA was demonstrated in five out of 114 IBD patient samples treated with ADL. To measure the drug concentration in patients treated with ADL, we generated a standard curve with different amounts of ADL on the shift of labeled TNF-α with the detection limit of 10 ng.

Conclusions:

We have applied our proprietary non-radio labeled liquid-phase homogeneous mobility shift assay to measure the ADA and ADL levels in serum from patients treated with ADL. The assays are reproducible with high sensitivity and accuracy, and are useful for evaluating ADA levels in serum samples from patients treated with ADL.

Introduction

Anti-tumor necrosis factor-alpha (TNF-α) biologics such as infliximab (IFX), etanercept, adalimumab (ADL) and certolizumab pegol have been shown to reduce disease activity in a number of autoimmune diseases, including Crohn's Disease (CD) and rheumatoid arthritis (RA). However, some patients do not respond to anti-TNF-α therapy, while others need higher or more frequent dosage due to lack of sufficient response, or develop infusion reactions.

Immunogenicity of therapeutic antibodies which causes the patients to develop antibodies against the drugs may contribute to the failure of the treatments and infusion reactions. Chimeric antibodies like IFX have a higher potential of inducing antibody generation compared to fully humanized antibodies such as ADL. The prevalence of antibodies to IFX (HACA) in RA patients varies from 12% to 44% and seems to be inversely proportional to the level of IFX in patient serum and therapeutic response. While the fully humanized ADL is supposed to be less immunogenic than murine or chimeric antibodies, several studies have reported the formation of human anti-humanized antibodies (HAHA) and showed the prevalence of antibody generation from 1% to 87% in RA and CD patients (Aikawa et al., Immunogenicity of Anti-TNF-alpha agents in autoimmune diseases. *Clin. Rev. Allergy Immunol.*, 38(2-3):82-9 (2010)).

Many patients with secondary response failure to one anti-TNF-α drug may benefit from switching to another anti-TNF-α drug or increasing dosage and/or dosing frequency. Monitoring of patients for drug and anti-drug antibody (ADA) levels is therefore warranted so that drug administration can be tailored to the individual patient. This approach allows dose adjustment when warranted or cessation of medication when ADA levels are present. (Bendtzen et al., Individual medicine in inflammatory bowel disease: monitoring bioavailability, pharmacokinetics and immunogenicity of anti-tumour necrosis factor-alpha antibodies. *Scand. J. Gastroenterol.*, 44(7):774-81 (2009); Afif et al., Clinical utility of measuring infliximab and human antichimeric antibody concentrations in patients with inflammatory bowel disease. *Am. J. Gastroenterol.*, 105(5):1133-9 (2010)).

A number of assays have been developed to measure HACA and HAHA. One of the limitations of the current methodologies is that ADA levels cannot be reliably measured when there is a high level of drugs in the circulation.

We have developed a proprietary non-radiolabeled, liquid-phase, mobility shift assay to measure the ADA and ADL levels in serum from patients treated with ADL which is not affected by the presence of the drug in the serum.

Methods

Fluorophore (Fl)-labeled ADL was incubated with patient serum to form the immunocomplex. A Fl-labeled small peptide was included as an internal control in each reaction. Different amounts of anti-human IgG were used to generate a standard curve to determine the serum ADA level. Free Fl-labeled ADL was separated from the antibody bound complex based on its molecular weight by size-exclusion chromatography. The ratio of free Fl-labeled ADL to internal control from each sample was used to extrapolate the HAHA concentration from the standard curve. A similar methodology was used to measure ADL levels in patient serum samples with Fl-labeled TNF-α.

Results

Figure 19:
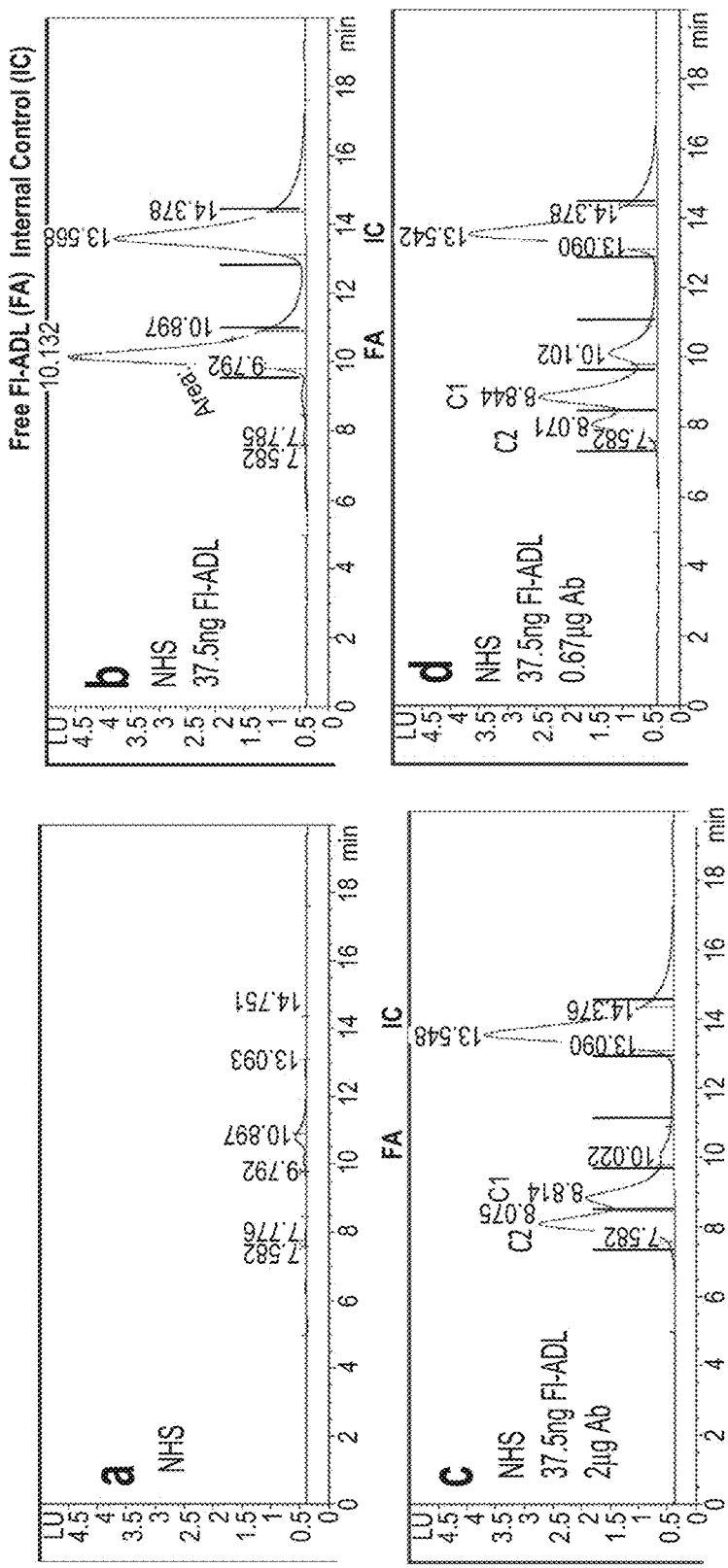
FIG. 19 shows mobility shift profiles of Fl-labeled ADL incubated with normal human serum (NHS) in the presence of different amounts of anti-human IgG. The addition of increasing amounts of anti-human IgG to the incubation mixture dose-dependently shifted the free Fl-ADL peak (FA) to the higher molecular mass eluting positions, C1 and C2, while the internal control (IC) did not change.
Figure 19:
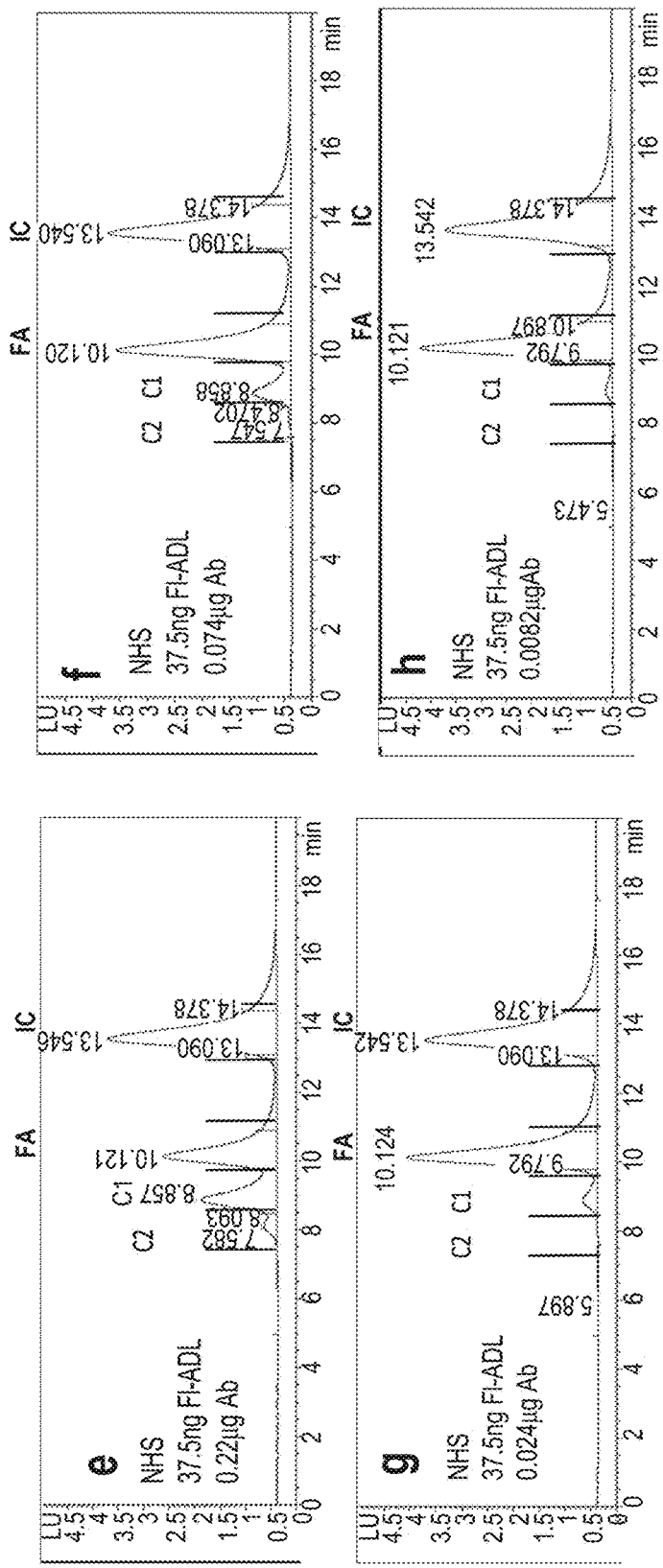

FIG. 19 shows the separation of the anti-human IgG bound Fl-ADL complex from the free Fl-ADL due to the mobility shift of the high molecular weight complex. As seen in panels c to h, the retention time of the fluorescent peak shifted from 10.1 min to 7.3-9.5 min. The more the anti-human IgG is added in the reaction mixture, the less the free ADL remains in the chromatogram and the more the immunocomplex is formed (h to c). The retention time for the internal control is 13.5 min.

Figure 20:
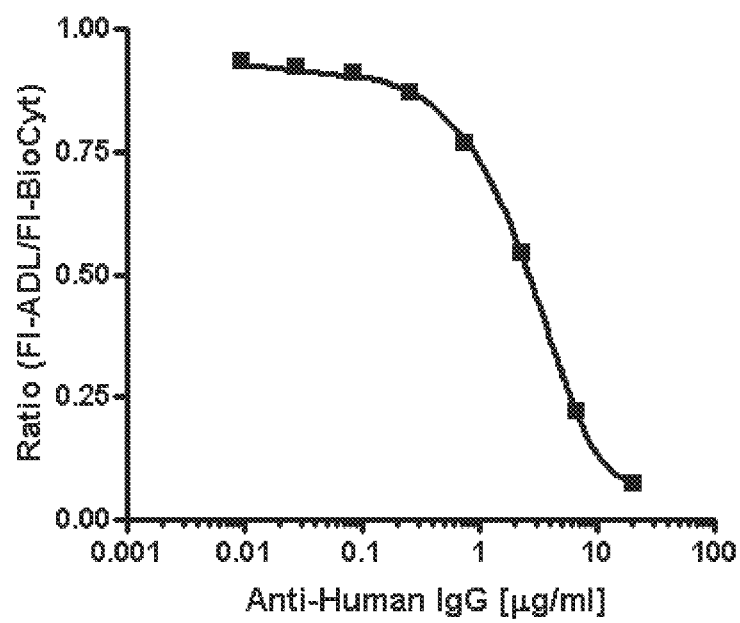
FIG. 20 shows a dose-response curve of anti-human IgG on the shift of free Fl-ADL. Increasing amounts of anti-human IgG were incubated with 37.5 ng of Fl-ADL and internal control. The more the antibody was added to the reaction mixture the lower the ratio of free Fl-ADL to internal control.

FIG. 20 shows the dose-response curve of the fluorescent peak shift caused by the addition of anti-human IgG. Increasing the concentration of anti-human IgG reduces the ratio of free ADL to internal control due to the formation of the immunocomplex. The assay sensitivity is 10 ng/ml of anti-human IgG. The internal control "Fl-BioCyt" corresponds to an Alexa Fluor® 488-biocytin (BioCyt) which combines the green-fluorescent Alexa Fluor® 488 fluorophore with biotin and an aldehyde-fixable primary amine (lysine) (Invitrogen Corp.; Carlsbad, Calif.).

Figure 21:
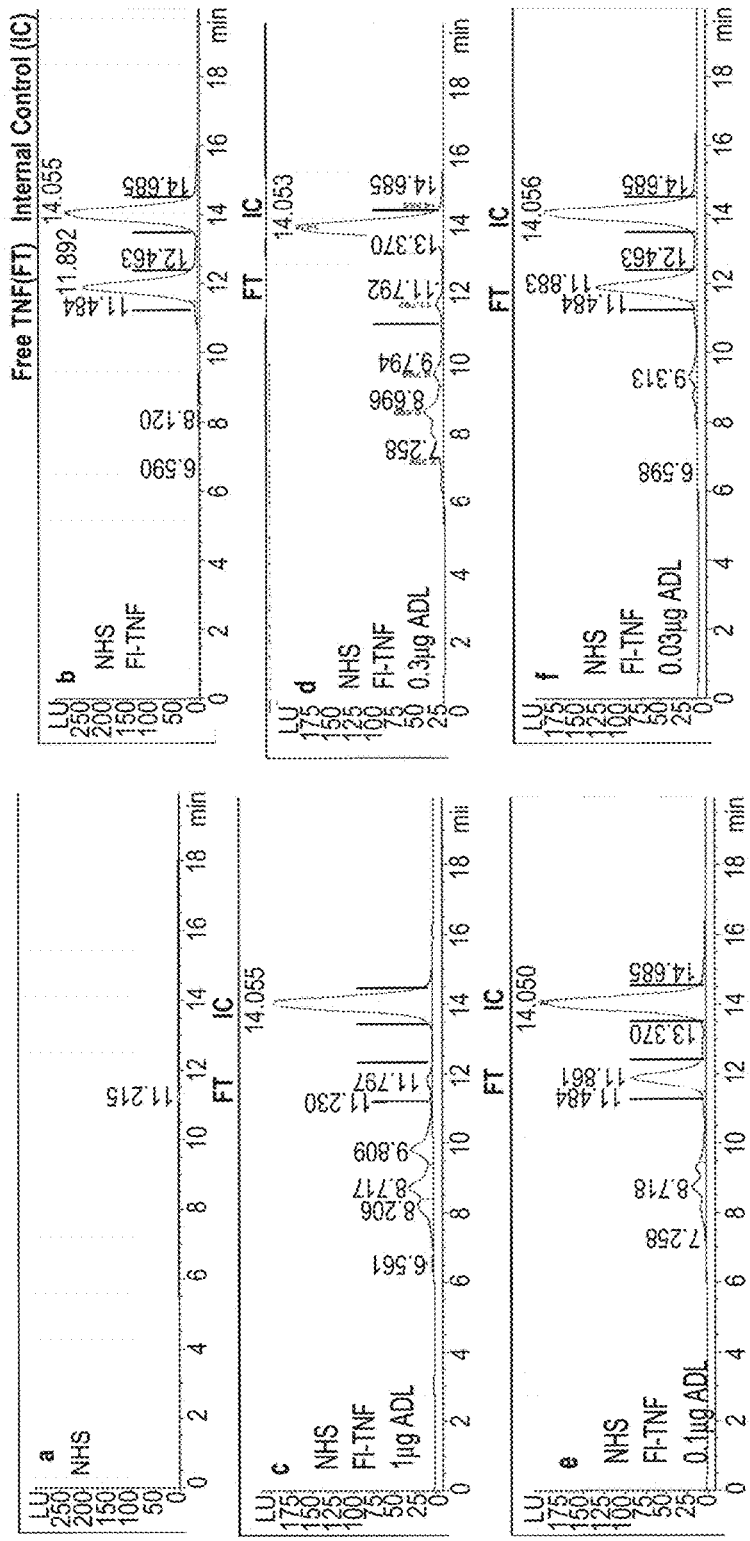
FIG. 21 shows mobility shift profiles of Fl-labeled TNF-α incubated with normal human serum (NHS) in the presence of different amounts of ADL. Ex=494 nm; Em=519 nm. The addition of increasing amounts of ADL to the incubation mixture dose-dependently shifted the free TNF-Fl peak (FT) to the higher molecular mass eluting positions, while the internal control (IC) peak did not change.
Figure 21:
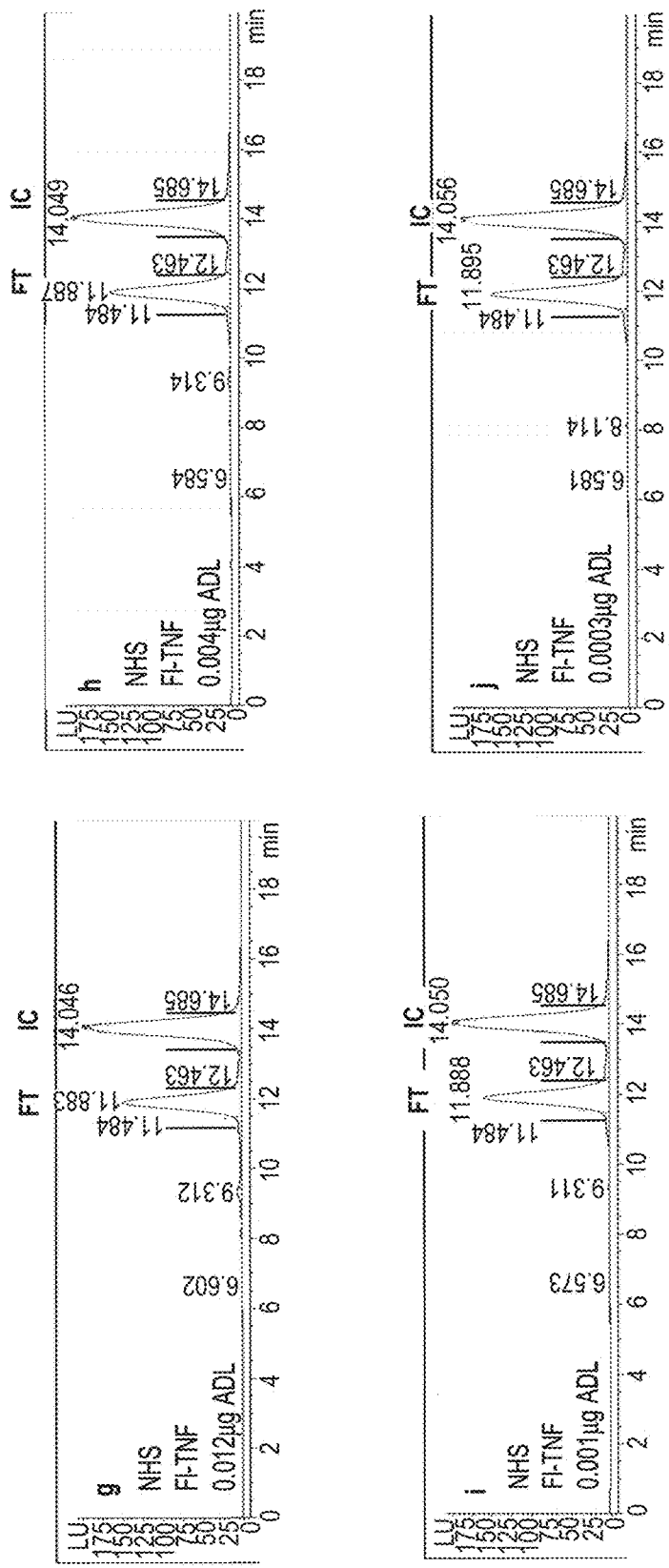

FIG. 21 shows the separation of the ADL bound TNF-α-Fl complex from the free TNF-α-Fl due to the mobility shift of the high molecular weight complex. As seen in panels c and j, the retention time of the fluorescent peak shifted from 11.9 min to 6.5-10.5 min. The more the ADL is added in the reaction mixture, the less the free TNF-α-Fl peak remains in the chromatogram and the more the immuno-complex is formed.

Figure 22:
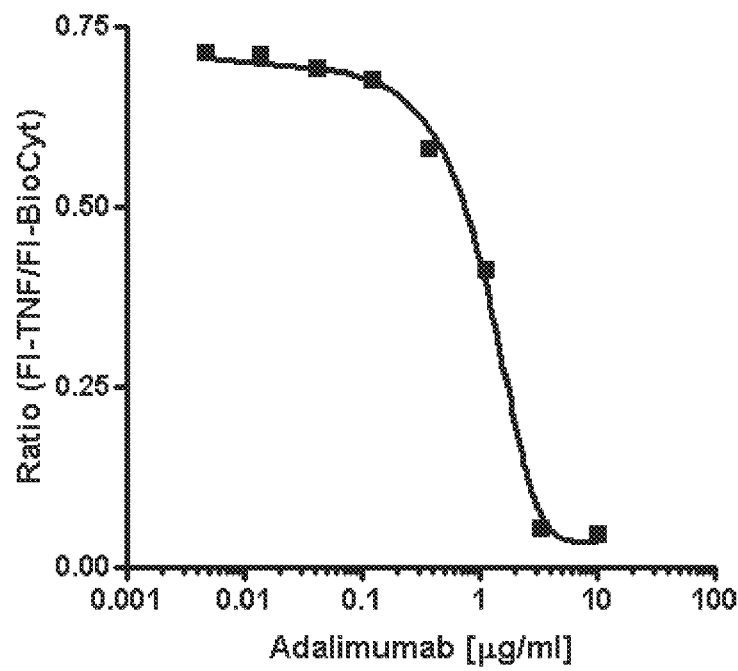
FIG. 22 shows a dose-response curve of ADL on the shift of free TNF-α-Fl. Increasing amounts of ADL were incubated with 100 ng of TNF-α-Fl and internal control. The more the antibody ADL was added to the reaction mixture the lower the ratio of free TNF-α-Fl to internal control.

FIG. 22 shows the dose-response curves of the TNF-α-Fl peak shift caused by the addition of ADL. Based on the added ADL, the detection limit is 10 ng/mL of ADL in serum.

Table 4 shows that serum samples from 100 healthy subjects and 114 IBD patients treated with ADL were analyzed for ADA and ADL levels using the mobility shift assay of the present invention. All 100 healthy subject samples had ADA levels below the limit of detection (no shift of the free Fl-ADL), whereas 5 out of the 114 patient samples had an ADA concentration of 0.012 to >20 µg/ml. The mean of ADL levels in 100 healthy subject samples was 0.76±1.0 µg/ml (range 0 to 9.4 µg/ml). The mean of ADL levels in 114 serum samples from patients treated with ADL was 10.8+17.8 µg/ml (range 0-139 µg/ml). Four out of five of the ADA positive samples had undetectable levels of ADL.

TABLE 4

Patient Serum Levels of ADA and ADL
Measured by the Mobility Shift Assay

| | Subjects (n) | Sex (M/F) | Age (Years) (Mean) | ADA Positive | ADL level (µg/ml) |
|---|---|---|---|---|---|
| Healthy Control | 100 | 38/62 | 18-62 (37.1) | 0 | 0.76 ± 1.00 |
| IBD Patient Treated with ADL | 114 | 51/63 | 20-69 (39.9) | 5 (4.3%) | 10.80 ± 17.80 |

Table 5 provides a further analysis of the serum samples from 100 healthy subjects and 114 IBD patients treated with ADL. In particular, 4 out of the 42 patient samples with 0-4 µg/ml ADL had an average ADA concentration of 0.012 to >20 µg/ml. Four out of four of the ADA positive samples had undetectable levels of ADL. For the detection of ADA, the 114 IBD patients treated with ADL were divided into two categories, 0-4 µg/ml of ADL and >4 µg/ml of ADL. Patients with greater than 4 µg/ml of ADL can be tested with a larger amount of ADL-Fl to address the competition of circulating ADL with ADL-Fl.

TABLE 5

Patient Serum Levels of ADA and ADL
Measured by the Mobility Shift Assay

| | Subjects (n) | Sex (M/F) | Age (Mean) | ADL Level (µg/ml) | ADA Positive |
|---|---|---|---|---|---|
| Healthy Control | 100 | 38/62 | 18-62 (37.1) | 0.76 ± 1.00 | 0 |
| IBD Patient Treated with ADL | 114 | 51/63 | 20-69 (39.9) | 10.80 ± 17.80 | 0-4 µg/ml ADL: 4 of 42 (9.52%) |

Conclusions

The mobility shift assay format used for measuring HACA/IFX is a homogeneous assay without the coating of antigens to a solid surface, and without multiple washing and incubation steps like a typical ELISA. This assay can be applied to measure ADA and anti-TNF drugs. The sensitivity of the assay (in g/ml range) is higher for both ADA and ADL measurement with patient serum compared to ELISA methods (in mg/ml range). Healthy control serum samples did not cause mobility shift of the Fl-labeled ADL, and 4.3% of the patients treated with ADL were found to have ADA by this assay. In particular, 9.52% of patients with 0.4 µg/ml ADL were found to have ADA in this assay. Further evaluation of normal samples and patient samples with higher concentrations of ADL-Fl will be done. Although healthy control serum samples caused mobility shift of the Fl-labeled TNF-α, which may have been due to the presence of soluble free receptor of TNF-α, the average of ADL in patients treated with ADL was much higher (10.8 vs. 0.76 µg/ml). Early detection of ADA and monitoring of ADL drug level while the patient is receiving ADL treatment will allow the physician to optimize the dosing of ADL or switch to another anti-TNF-α drug when appropriate and, thereby, optimizing the overall management of the patient's disease.

Example 7: Determining the Concentration Levels of REMICADE™ and Human Anti-Drug Antibodies This example describes a method for determining the levels of Anti-TNFα Drugs, e.g. REMICADE™ (infliximab), in a serum sample as well as for determining the levels of a human anti-drug antibody, e.g. a human anti-chimeric antibody (HACA) to REMICADE™ (infliximab).

Step 1: Determining Concentration Level of REMICADE™ (Infliximab) in a Sample.

In one exemplary embodiment, TNFα is labeled with a fluorophore (e.g. Alexa$_{647}$), wherein the fluorophore can be detected by, either or both of, the visible and fluorescent spectra. The labeled TNFα is incubated with human serum in a liquid phase reaction to allow the anti-TNFα drug present in the serum to bind. The labeled TNFα can also be incubated with known amounts of the anti-TNFα drug in a liquid phase reaction to create a standard curve. Following incubation, the samples are loaded directly onto a size exclusion column. Binding of the anti-TNFα drug to the labeled TNFα results in a leftward shift of the peak compared to labeled TNFα alone. The concentration of the anti-TNFα drug present in the serum sample can then be compared to the standard curve and controls.

SE-HPLC Analysis of REMICADE™ (Infliximab) Levels in Patient Serum.

Human recombinant TNFα was labeled with a fluorophore, Alexa Fluor® 488, according to the manufacturer's instructions. Labeled TNFα was incubated with different amounts of REMICADE™ or patient serum for one hour at room temperature. Samples of 100 µL volume were analyzed by size-exclusion chromatography on an HPLC system. Fluorescence label detection was used to monitor the free labeled TNFα and the bound labeled TNFα immunocomplex based on their retention times. Serum REMICADE™ levels were calculated from the standard curve.

The following equations are relevant to this assay:

$$\text{labeled-TNF}\alpha + \text{REMICADE}^{TM} \rightarrow (\text{labeled-TNF}\alpha.\text{REMICADE}^{TM})_{complex} \quad \text{Equation I:}$$

$$[\text{REMICADE}^{TM}]_{without\text{-}labeled\text{-}TNF\alpha\text{-}present} = [(\text{labeled-TNF}\alpha.\text{REMICADE}^{TM})_{complex}] \quad \text{Equation II:}$$

$$[\text{REMICADE}^{TM}] = [(\text{labeled-TNF}\alpha.\text{REMICADE}^{TM})_{complex}/[\text{labeled-TNF}\alpha] \times [\text{labeled-TNF}\alpha] \quad \text{Equation III:}$$

In Step 1, a known amount of the labeled-TNFα is contacted with a REMICADE™-containing serum sample. The labeled-TNFα and the REMICADE™ form a complex, (labeled-TNFα.REMICADE™)$_{complex}$. See Equation I. Because almost all of the REMICADE™ will form a complex with the labeled-TNFα, the concentration of REMICADE™ present before introduction of the labeled-TNFα is equal to the measured concentration of labeled-TNFα.REMICADE™$_{complex}$, See Equation II. The concentration level of REMICADE™ is calculated by multiplying the ratio of [(label-TNFα.REMICADE™)$_{complex}$]/[labeled-TNFα] by [labeled-TNFα], See Equation III. The ratio, [(label-TNFα.REMICADE™)$_{complex}$]/[labeled-TNFα], is obtained by integrating the area-under-the curve for the (label-TNFα.REMICADE™)$_{complex}$ peak, from a plot of signal intensity as a function of elution time from the size exclusion HPLC, and dividing this number by the resultant integration of the area-under-the-curve for the labeled-TNFα peak from the plot. The [labeled-TNFα] is known a priori.

Step 2: Determining Level of Human Anti-Chimeric Antibody, HACA.

In one exemplary embodiment, an anti-TNFα drug, e.g., REMICADE™, is labeled with a fluorophore, e.g., Alexa$_{647}$, wherein the fluorophore can be detected by, either or both of, the visible and fluorescent spectra. The labeled anti-TNFα drug is incubated with human serum in a liquid phase reaction to allow any HACA present in the serum to bind. The labeled anti-TNFα drug can also be incubated with known amounts of an anti-IgG antibody or pooled positive patient serum in a liquid phase reaction to create a standard curve. Following incubation, the samples are loaded directly onto a size exclusion column. Binding of the autoantibodies to the labeled anti-TNFα drug results in a leftward shift of the peak compared to labeled drug alone. The concentration of HACA present in the serum sample can then be compared to the standard curve and controls.

SE-HPLC Analysis of HACA Levels in Patient Serum.

Purified REMICADE™ was labeled with a fluorophore. Labeled REMICADE™ was incubated with different dilutions of pooled HACA-positive serum or diluted patient serum for one hour at room temperature. Samples of 100 μL volume were analyzed by size-exclusion chromatography on an HPLC system. Fluorescence label detection was used to monitor the free labeled REMICADE™ and the bound labeled REMICADE™ immuno-complex based on their retention times. The ratio of bound and free labeled REMICADE™ was used to determine the HACA level as described below.

Mobility Shift Assay Procedure to Measure HACA in Serum.

The principle of this assay is based on the mobility shift of the complex of an anti-drug antibody, e.g. HACA, with Alexa$_{647}$-labeled REMICADE™ relative to free Alexa$_{647}$-labeled REMICADE™, on size exclusion-high performance liquid chromatography (SE-HPLC) due to the increase in molecular weight of the complex. The chromatography is performed in an Agilent-1200 HPLC System, using a Bio-Sep 300×7.8 mm SEC-3000 column (Phenomenex) with a molecular weight fractionating range of 5,000-700,000 and a mobile phase of 1×PBS, pH 7.3, at a flow-rate of 0.5-1.0 mL/min with fluorescence label detection, e.g. UV detection at 650 nm. In front of the Agilent-1200 HPLC System with a Bio-Sep 300×7.8 mm SEC-3000 column is a analytical pre-column which is a BioSep 75×7.8 mm SEC-3000. A 100 μL sample volume is loaded onto the column for each analysis. The complex of HACA and labeled REMICADE™ complex is formed by incubating serum from a REMICADE™ treated patient and labeled REMICADE™ in the 1×PBS, pH 7.3, elution buffer at room temperature for 1 hour before SE-HPLC analysis.

The following equations are relevant to this assay:

REMICADE™+labeled-REMICADE™+HACA→(REMICADE™.HACA)$_{complex}$+(Labeled-REMICADE™.HACA)$_{complex}$    Equation IV:

[REMICADE™]/[REMICADE™.HACA$_{complex}$]=[labeled-REMICADE™]/[Labeled-REMICADE™.HACA$_{complex}$]    Equation V:

[HACA]=[REMICADE™.HACA]$_{complex}$+[labeled-REMICADE™.HACA]$_{complex}$    Equation VI:

[REMICADE™.HACA$_{complex}$]=[REMICADE™]×[labeled-REMICADE™.HACA$_{complex}$]/[labeled-REMICADE™]    Equation VII:

[labeled-REMICADE™.HACA$_{complex}$]=[labeled-REMICADE™]×[labeled-REMICADE™.HACA$_{complex}$]/[labeled-REMICADE™]    Equation VIII:

[REMICADE™]$_{effective-amount}$=[REMICADE™]−[HACA]    Equation IX:

Determining the concentration levels of human anti-TNFα drug antibodies, e.g. HACA. A known concentration of Labeled-REMICADE™ is added to a serum sample. HACA forms a complex with either REMICADE™ or Labeled-REMICADE™, See Equation IV. The [REMICADE™] is determined in Step 1 above. By integrating the area-under-the-curve for the labeled-REMICADE™.HACA$_{complex}$ and dividing this number by the resultant integration for the area-under-the-curve for the free Labeled-REMICADE™, the ratio of [labeled-REMICADE™.HACA$_{complex}$] to [labeled-REMICADE™] is obtained. The ratio of [REMICADE™] to [REMICADE™.HACA$_{complex}$] is equal to the ratio of [labeled-REMICADE™] to [labeled-REMICADE™.HACA)$_{complex}$], See Equation V. Because HACA equilibrates and forms a complex with both REMICADE™ and Labeled-REMICADE™, the total amount of HACA equals the sum of the amount of REMICADE™.HACA$_{complex}$ and the amount of labeled-REMICADE™.HACA$_{complex}$, See Equation VI. Because the ratio of [REMICADE™] to [REMICADE™.HACA$_{complex}$] is equal to the ratio of [labeled-REMICADE™] to [labeled-REMICADE™.HACA$_{complex}$], both the [REMICADE™-HACA]$_{complex}$ and the [labeled-REMICADE™-HACA$_{complex}$] are determined by multiplying the ratio of the [labeled-REMICADE™ HACA$_{complex}$)]/[labeled-REMICADE™] by, respectively, the concentration amount of REMICADE™, determined in Step 1, and the concentration amount of labeled-REMICADE™, known a priori, See Equations VII and VIII. Therefore, the total amount of HACA equals the sum of (1) the [REMICADE™], from step 1, multiplied by [labeled-REMICADE™.HACA)$_{complex}$]/[labeled-REMICADE™], and (2) the [labeled REMICADE™], known a priori, multiplied by [labeled-REMICADE™.HACA)$_{complex}$]/[labeled-REMICADE™].

Determining the Effective Concentration Levels of REMICADE™.

Because HACA complexes with REMICADE™, the effective amount of REMICADE™ available in a serum sample is the amount of REMICADE™, measured from Step 1, minus the amount of HACA, measured from Step 2, See Equation IX.

Exemplary Calculation.

In patient JAG on V10, the [REMICADE™] was determined to be 7.5 μg/ml, See FIG. 16c. This result was obtained by following Step 1 and using Equations I-III. 7.5 μg/ml equals 30 ng/4 μL. Since 4 μL of sample was used in the measurement in Step 2, a total of 30.0 ng of REMICADE™ was present in the sample analyzed. The ratio of [labeled-REMICADE™.HACA]$_{complex}$/[labeled-REMICADE™] for patient JAG on V10 was 0.25, See FIG. 16b. The [labeled-REMICADE™] introduced into the sample was 37.5 ng/100 μL. Since 100 μL of the labeled-REMICADE™ was used in the measurement in Step 2, a total of 37.5 ng of labeled-REMICADE™ was present in the sample analyzed. Using Equation VII, the total amount of REMICADE™.HACA$_{complex}$ was 30 ng multiplied by 0.25, which is equal to 7.5 ng labeled-REMICADE™.HACA$_{complex}$. Using Equation VIII, the total amount of labeled-REMICADE™.HACA$_{complex}$ was 37.5 ng multiplied by 0.25, which is equal to 9.4 ng labeled-REMICADE™.HACA$_{complex}$. Using Equation VI, the total amount of HACA equals the sum of 9.4 ng and 7.5 ng, which equals 16.9 ng HACA. The 16.9 ng HACA was present in 4 μL of sample. The [HACA] was 16.9 ng/4 μL, which equals 4.23 μg/ml. Using Equation IX, the effective amount of REMICADE™ is equal to 7.5 μg/ml REMICADE™, determined from Step 1, minus 4.23 g/ml HACA, determined from Step 2. In this exemplary calculation, the effective [REMICADE™] was equal to 3.27 g/ml.

Example 8: Determining the Concentration Levels of HUMIRA™ and Human Anti-Drug Antibodies This example describes a method for determining the levels of HUMIRA™ in a serum sample as well as for determining the levels of human anti-human antibodies (HAHA).

Step 1: Determining Concentration Level of HUMIRA™ in a Sample.

In one exemplary embodiment, TNFα is labeled with a fluorophore (e.g. Alexa$_{647}$), wherein the fluorophore can be detected by, either or both of, the visible and fluorescent spectra. The labeled TNFα is incubated with human serum in a liquid phase reaction to allow the anti-TNFα drug present in the serum to bind. The labeled TNFα can also be incubated with known amounts of the anti-TNFα drug in a liquid phase reaction to create a standard curve. Following incubation, the samples are loaded directly onto a size exclusion column. Binding of the anti-TNFα drug to the labeled TNFα results in a leftward shift of the peak compared to labeled TNFα alone. The concentration of the anti-TNFα drug present in the serum sample can then be compared to the standard curve and controls.

SE-HPLC Analysis of HUMIRA™ Levels in Patient Serum.

Human recombinant TNFα was labeled with a fluorophore, Alexa Fluor® 488, according to the manufacturer's instructions. Labeled TNFα was incubated with different amounts of HUMIRA™ or patient serum for one hour at room temperature. Samples of 100 μL volume were analyzed by size-exclusion chromatography on an HPLC system. Fluorescence label detection was used to monitor the free labeled TNFα and the bound labeled TNFα immuno-complex based on their retention times. Serum HUMIRA™ levels were calculated from the standard curve.

The following equations are relevant to this assay:

labeled-TNFα+HUMIRA™→(labeled-TNFα.HUMIRA™)$_{complex}$   Equation X:

[HUMIRA™]=[(labeled-TNFα.HUMIRA)$_{complex}$]   Equation XI:

[HUMIRA™]=[(label-TNFα.HUMIRA™)$_{complex}$]/[labeled-TNFα]×[labeled-TNFα]   Equation XII:

In Step 1, a known amount of the labeled-TNFα is contacted with a HUMIRA™-containing serum sample. The labeled-TNFα and the HUMIRA™ form a complex, (labeled-TNFα.HUMIRA)$_{complex}$, See Equation X. Because almost all of the HUMIRA™ will form a complex with the labeled-TNFα, the [HUMIRA™] present before introduction of the labeled-TNFα is equal to the measured [(labeled-TNFα.HUMIRA™)$_{complex}$], See Equation XI. The [HUMIRA™] is calculated by multiplying the ratio of [(label-TNFα.HUMIRA™)$_{complex}$]/[Labeled-TNFα] by [labeled-TNFα], See Equation XII. By integrating the area-under-the-curve for the labeled-TNFα and the area-under-the-curve for the (labeled-TNFα.HUMIRA™)$_{complex}$ and dividing the resultant integration for (labeled-TNFα.HUMIRA™)$_{complex}$ by the resultant integration for the labeled-TNFα, the ratio of [(label-TNFα.HUMIRA™)$_{complex}$] to [labeled-TNFα] is obtained. The [labeled-TNFα] is known a priori.

Step 2: Determining Level of Human Anti-Human Antibody, e.g. HAHA.

In one exemplary embodiment, an anti-TNFα drug, e.g., HUMIRA™, is labeled with a fluorophore, e.g., Alexa$_{647}$, wherein the fluorophore can be detected by, either or both of, the visible and fluorescent spectra. The labeled anti-TNFα drug is incubated with human serum in a liquid phase reaction to allow any HAHA present in the serum to bind. The labeled anti-TNFα drug can also be incubated with known amounts of an anti-IgG antibody or pooled positive patient serum in a liquid phase reaction to create a standard curve. Following incubation, the samples are loaded directly onto a size exclusion column. Binding of the autoantibodies to the labeled anti-TNFα drug results in a leftward shift of the peak compared to labeled drug alone. The concentration of HAHA present in the serum sample can then be compared to the standard curve and controls.

SE-HPLC Analysis of HAHA Levels in Patient Serum.

Purified HUMIRA™ was labeled with a fluorophore. Labeled HUMIRA™ was incubated with different dilutions of pooled HAHA-positive serum or diluted patient serum for one hour at room temperature. Samples of 100 μL volume were analyzed by size-exclusion chromatography on an HPLC system. Fluorescence label detection was used to monitor the free labeled HUMIRA™ and the bound labeled HUMIRA™ immuno-complex based on their retention times. The ratio of bound and free labeled HUMIRA™ was used to determine the HAHA level as described below.

Mobility Shift Assay Procedure to Measure HAHA in Serum.

The principle of this assay is based on the mobility shift of the antibody, e.g. HAHA, bound Alexa$_{647}$-labeled HUMIRA™ complex versus free Alexa$_{647}$-labeled HUMIRA™ on size exclusion-high performance liquid chromatography (SE-HPLC) due to the increase in molecular weight of the complex. The chromatography is performed in an Agilent-1200 HPLC System, using a Bio-Sep 300×7.8 mm SEC-3000 column (Phenomenex) with a molecular weight fractionating range of 5,000-700,000 and a mobile phase of 1×PBS, pH 7.3, at a flow-rate of 0.5-1.0 mL/min with fluorescence label detection, e.g. UV detection at 650 nm. In front of the Agilent-1200 HPLC System with a Bio-Sep 300×7.8 mm SEC-3000 column is a analytical pre-column which is a BioSep 75×7.8 mm SEC-3000. A 100 μL sample volume is loaded onto the column for each analysis. A 100 μL sample volume is loaded onto the column for each analysis. The HAHA bound labeled HUMIRA™ complex is formed by incubating serum from a HUMIRA-treated patient and labeled HUMIRA™ in the 1×PBS, pH 7.3, elution buffer at room temperature for 1 hour before SE-HPLC analysis.

HUMIRA™+labeled-HUMIRA™+HAHA→(HUMIRA™.HAHA)$_{complex}$+(labeled-HUMIRA™.HAHA)$_{complex}$   Equation XIII:

[HUMIRA™]/[HUMIRA™.HAHA$_{complex}$]=[labeled-HUMIRA™]/[labeled-HUMIRA.HAHA$_{complex}$]   Equation XIV:

[HAHA]=[HUMIRA™.HAHA$_{complex}$]+[labeled-HUMIRA™.HAHA$_{complex}$]   Equation XV:

[HUMIRA™.HAHA$_{complex}$]=[HUMIRA™]×[labeled-HUMIRA™]/[labeled-HUMIRA™.HAHA$_{complex}$]   Equation XVI:

[labeled-HUMIRA™.HAHA$_{complex}$]=[labeled-HUMIRA™]×[labeled-HUMIRA™.HAHA$_{complex}$]/[labeled-HUMIRA™]   Equation XVII:

[HUMIRA™]$_{effective-amount}$=[HUMIRA™]−[HAHA]   Equation XVIII:

Calculation for Step 2: A known concentration of labeled-HUMIRA™ is added to a serum sample. HAHA forms a complex with either HUMIRA™ or Labeled-HUMIRA™, See Equation XIII. The [HUMIRA™] is determined in Step 1 as described above. By integrating the area-under-the-curve for the Labeled-HUMIRA™.HAHA$_{complex}$ and the area-under-the-curve for the Labeled-HUMIRA™ and dividing the resultant integration for the Labeled-HUMIRA™.HAHA$_{complex}$ by the resultant integration for the Labeled-HUMIRA™ the ratio of the [Labeled-HUMIRA™.HAHA$_{complex}$] to [Labeled-HUMIRA™] is obtained. The ratio of the [HUMIRA™] to the [HUMIRA™.HAHA$_{complex}$] is equal to the ratio of the [Labeled-HUMIRA™] to the [Labeled-HUMIRA™.HAHA$_{complex}$], See Equation XIV. Because HAHA equilibrates and forms a complex with both HUMIRA and Labeled-HUMIRA™, the total amount of HAHA equals the sum of the amount of HUMIRA™.HAHA$_{complex}$ and the Labeled-HUMIRA™.HAHA$_{complex}$, See Equation XV. Because the ratio of [HUMIRA™] to [HUMIRA™.HAHA$_{complex}$] is equal to the ratio of [Labeled-HUMIRA] to [Labeled-HUMIRA™.HAHA$_{complex}$], the concentration of both the [HUMIRA™-HAHA$_{complex}$] and the [Labeled-HUMIRA™-HAHA$_{complex}$] are determined by multiplying the ratio of the [Labeled-HUMIRA.HAHA$_{complex}$]/[Labeled-HUMIRA] by the [HUMIRA™], determined in Step 1, and the [Labeled-HUMIRA™], known a priori, respectively, See Equations XVI and XVII. Because HAHA complexes with HUMIRA™, the effective amount of HUMIRA™ available in a serum sample is the amount of HUMIRA, measured from Step 1, minus the amount of HAHA, measured from Step 2, See Equation XVIII.

Exemplary Calculation.

Figure 25:
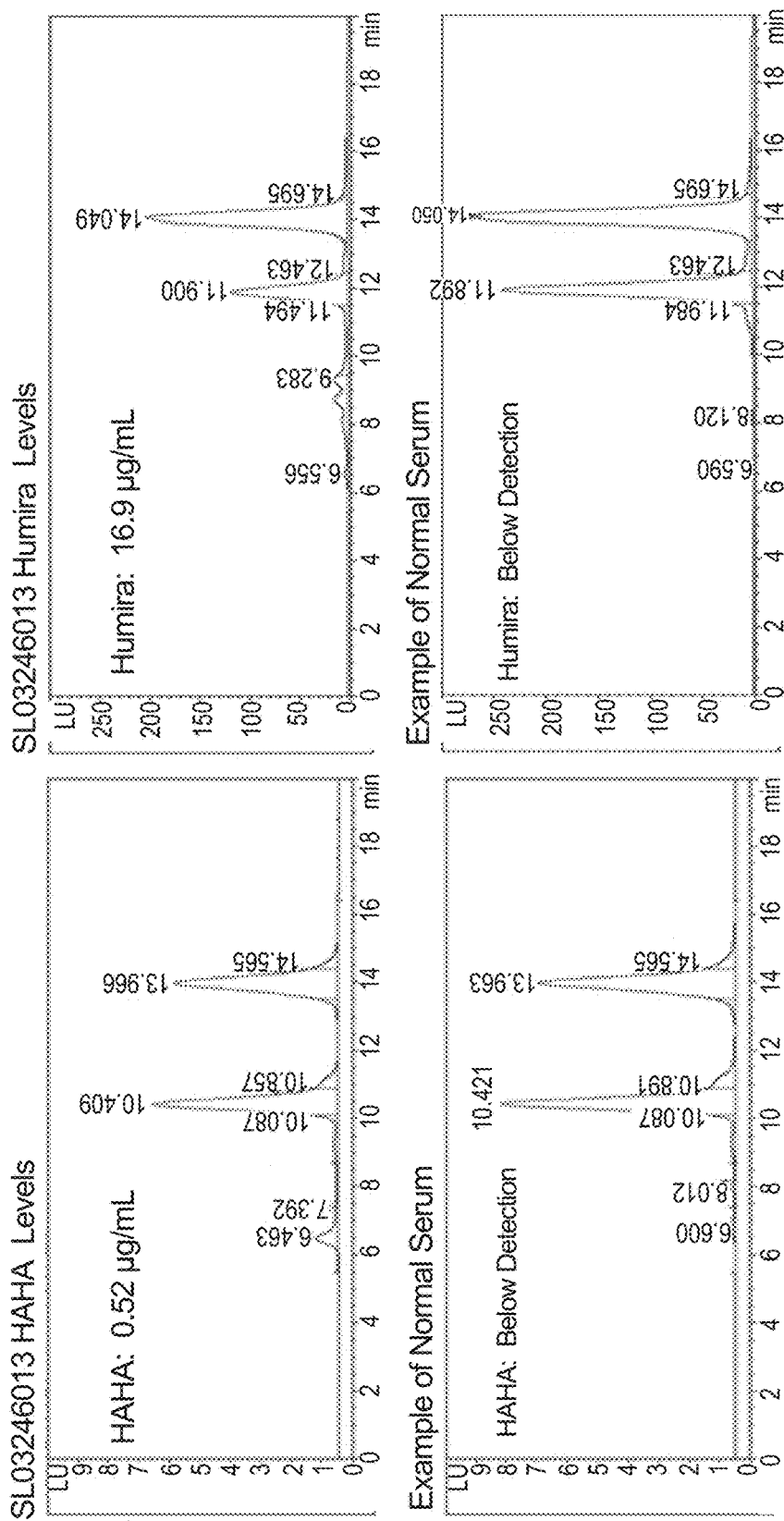
FIG. 25 shows the mobility shift profiles of Fl-Labeled HUMIRA (ADL) incubated with normal (NHS) or pooled HAHA positive patient serum.

In patient SL03246013, see FIG. 25, the [HUMIRA™] was determined to be 16.9 µg/ml, see FIG. 25. This result was obtained by following Step 1 and using Equations X-XII. 16.9 µg/ml equals 67.6 ng/4 µL. Since 4 µL of sample was used in the measurement in Step 2, a total of 67.6 ng of HUMIRA™ was present in the sample analyzed. The ratio of [labeled-HUMIRA™.HAHA]$_{complex}$/[labeled-HUMIRA™] for patient SL03246013 was 0.055, see FIG. 25. The [labeled-HUMIRA™] introduced into the sample was 37.5 ng/100 µL. Since 100 µL of the labeled-HUMIRA™ was used in the measurement in Step 2, a total of 37.5 ng of labeled-HUMIRA™ was present in the sample analyzed. Using Equation XVI, the total amount of HUMIRA™.HAHA$_{complex}$ was 67.6 ng multiplied by 0.055, which is equal to 3.71 ng labeled-HUMIRA™.HAHA$_{complex}$. Using Equation XVII, the total amount of labeled-HUMIRA™.HAHA$_{complex}$ was 37.5 ng multiplied by 0.055, which is equal to 2.06 ng labeled-HUMIRA™.HAHA$_{complex}$. Using Equation XV, the total amount of HAHA equals the sum of 3.71 ng and 2.06 ng, which equals 5.77 ng HAHA. The 5.77 ng HAHA was present in 4 µL of sample. The [HAHA] was 5.77 ng/4 µL, which equals 1.44 µg/ml. Using Equation XVIII, the effective amount of HUMIRA™ is equal to 16.99 µg/ml HUMIRA™, determined from Step 1, minus 1.44 µg/ml HAHA, determined from Step 2. In this exemplary calculation, the effective [HUMIRA™] was equal to 15.46 µg/ml.

Example 9: Determining the Amount of a Complex of HACA or HAHA with Either REMICADE™, Labeled-REMICADE™, HUMIRA, or Labeled-HUMIRA This example describes a method for determining the amount of a complex of HACA or HAHA with either REMICADE™, Labeled-REMICADE™, HUMIRA, or Labeled-HUMIRA™ with reference to an internal standard.

By using an internal control, e.g. Biocytin-Alexa 488, serum artifacts and variations from one experiment to another experiment can be identified and properly analyzed. The amount of internal control, e.g. Biocytin-Alexa 488, is from about 50 to about 200 pg per 100 µL analyzed.

Fluorophore (Fl)-labeled HUMIRA™ was incubated with patient serum to form the immunocomplex. A Fl-labeled small peptide, e.g. Biocytin-Alexa 488, was included as an internal control in each reaction. In one instance, different amounts of anti-human IgG were used to generate a standard curve to determine the serum HAHA levels. In another instance, titrated pooled positive patient serum that has been calibrated with purified HAHA was used to generate a standard curve to determine the serum HAHA levels. In yet another instance, the method described in Example 7 was used to generate a standard curve to determine the serum HAHA levels. Free labeled HUMIRA was separated from the antibody bound complex based on its molecular weight by size-exclusion chromatography. The ratio of free labeled HUMIRA to an internal control from each sample was used to extrapolate the HAHA concentration from the standard curve. A similar methodology was used to measure HUMIRA levels in patient serum samples with labeled TNF-α.

Figure 23:
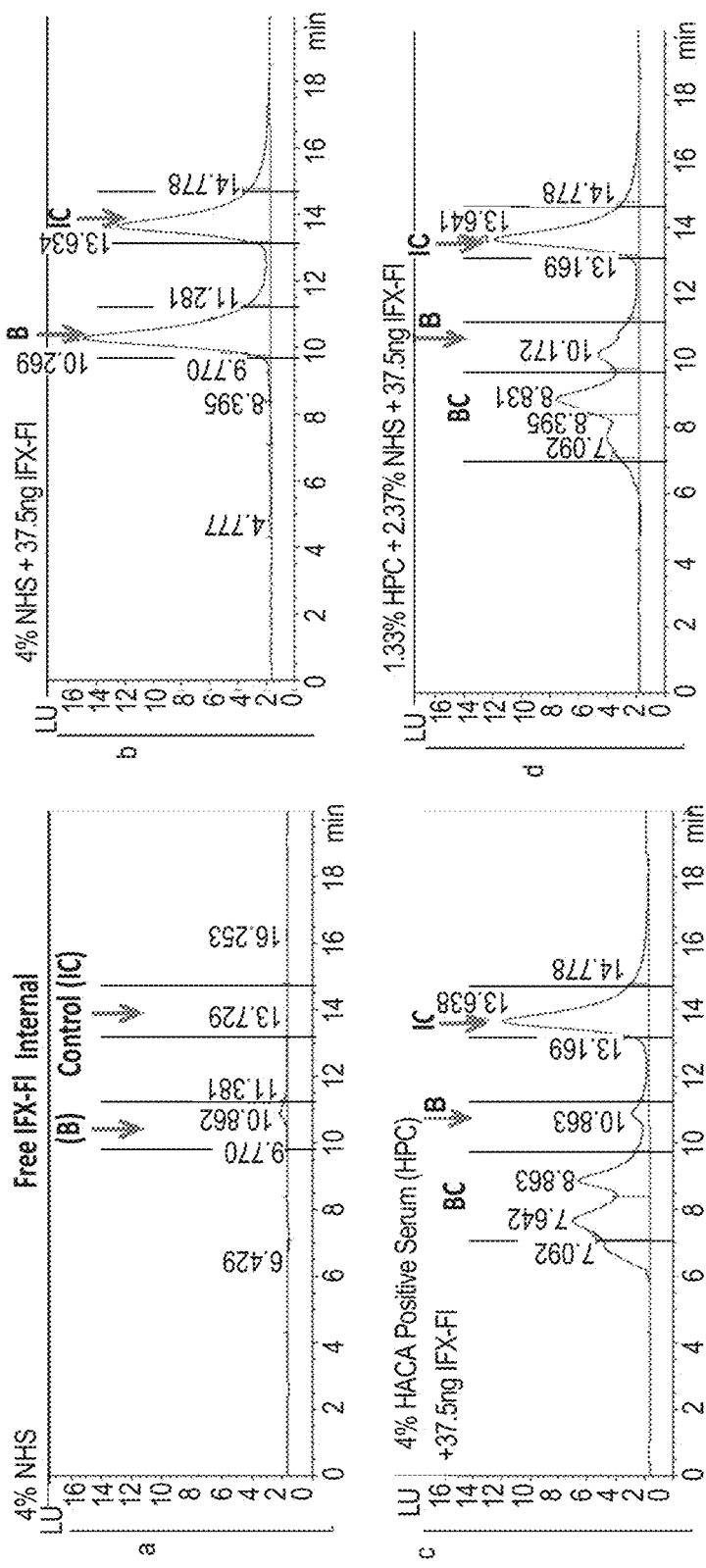
FIG. 23 shows the mobility shift profiles of Fl-labeled Remicade (IFX) Incubated with Normal (NHS) or Pooled HACA Positive Patient Serum.
Figure 23:
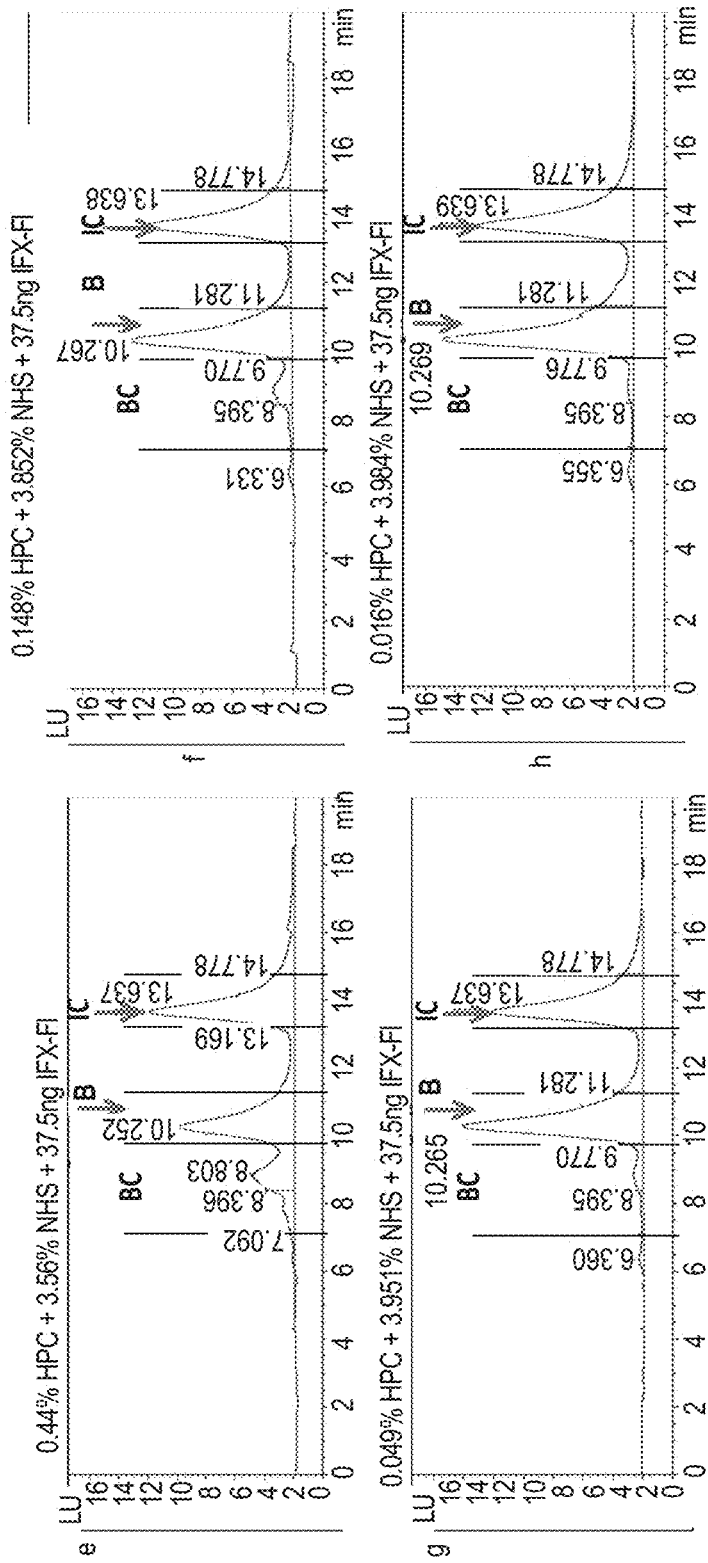
Figure 24:
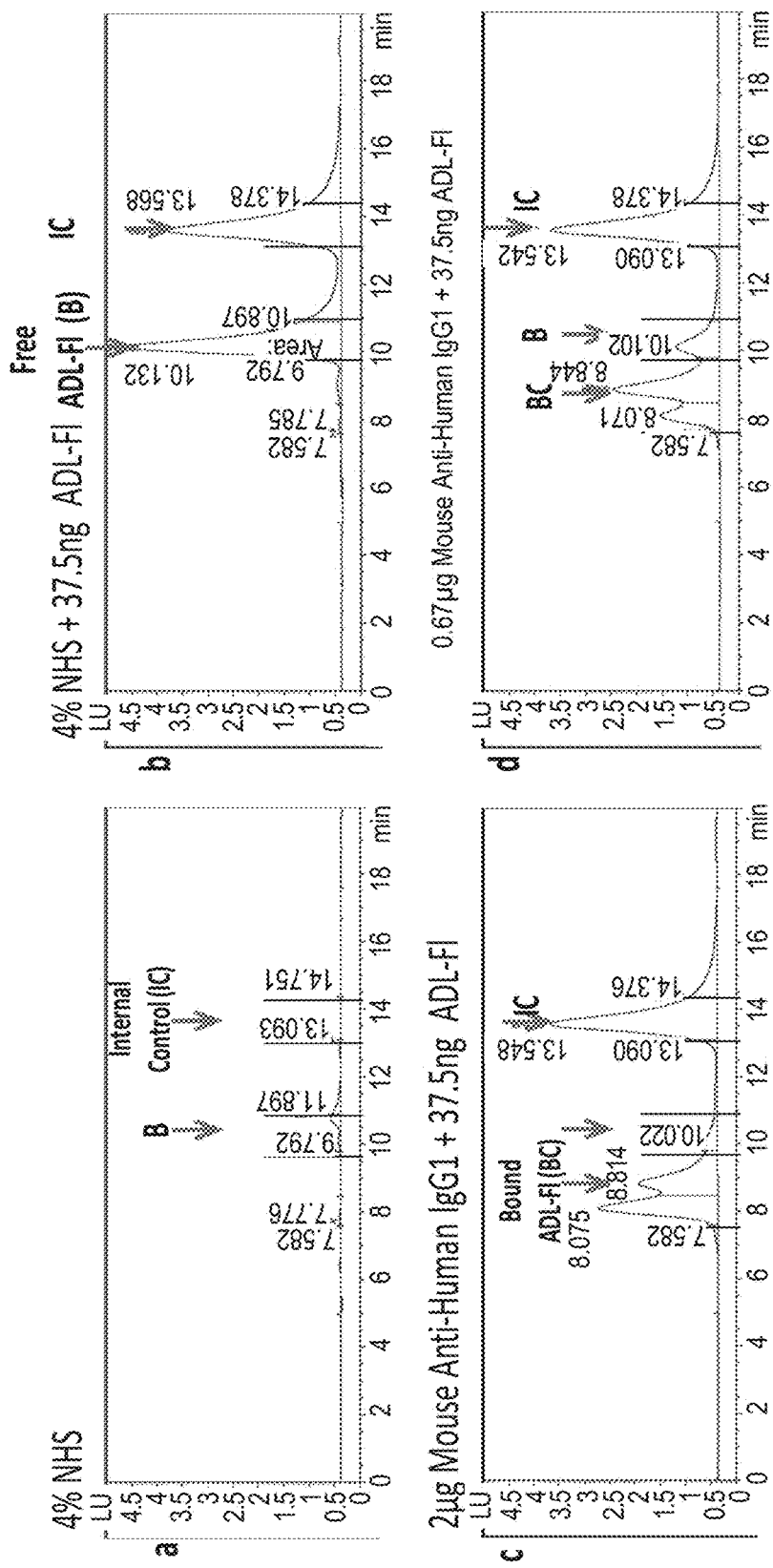
FIG. 24 shows the mobility shift profiles of Fl-Labeled HUMIRA (ADL) incubated with normal (NHS) or Mouse Anti-Human IgG1 Antibody.
Figure 24:
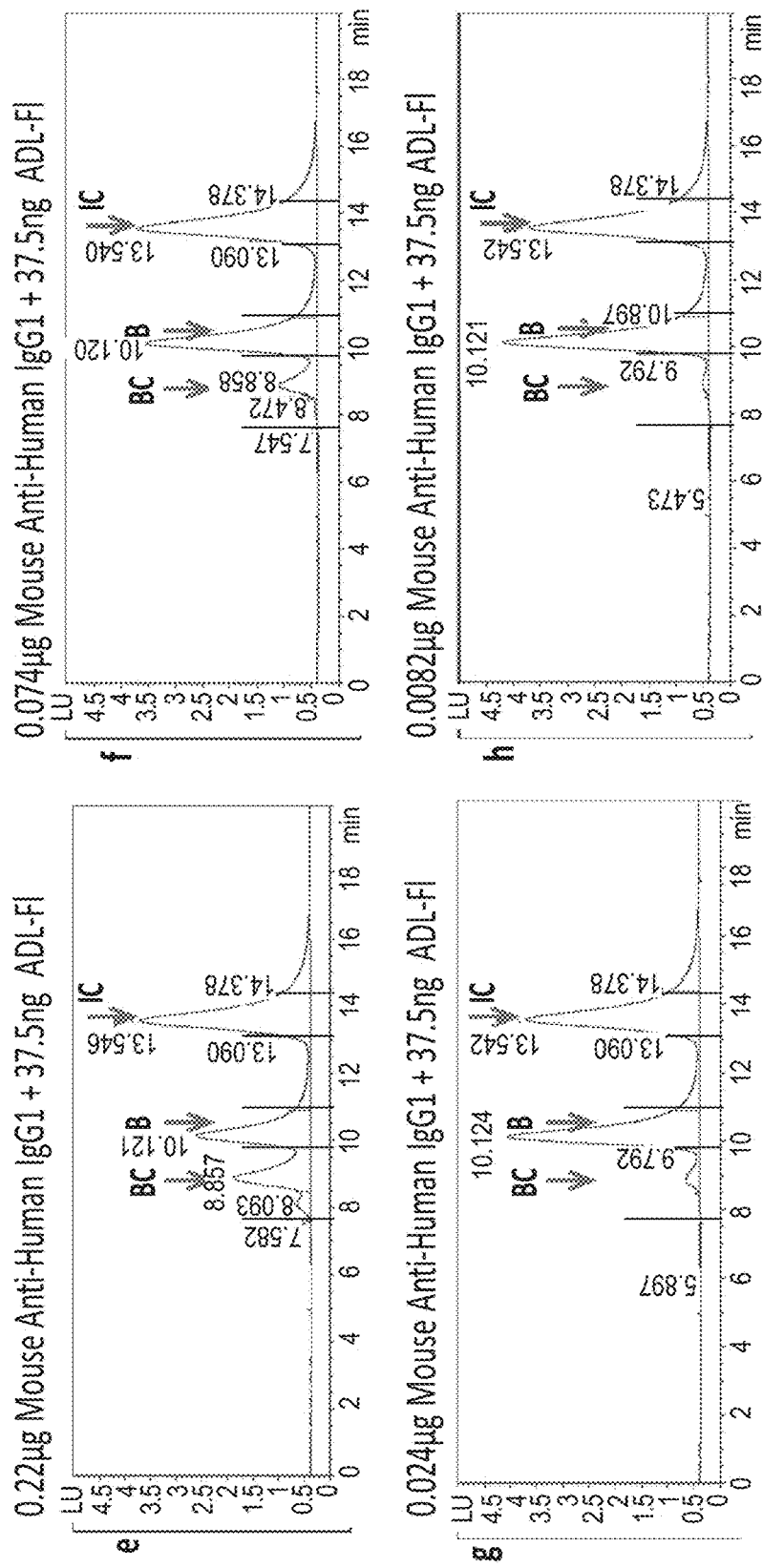

The initial ratio of the Labeled-Drug, i.e. Labeled-REMICADE™ or Labeled-HUMIRA, to the internal control is equal to 100. As depicted in FIGS. 23 and 24, when the ratio of the Labeled-Drug to the internal control falls below 95, the labeled-drug is inferred to be complexed with an anti-Drug binding compound, e.g. HACA, HAHA. The ratio of the [Labeled-drug] to [internal control] is obtained by integrating the areas-under-the-curve for the Labeled-Drug and for the internal control and then dividing the resultant integration for the Labeled-Drug by the resultant integration for the internal control.

Example 10: Determining the Ratio of Complexed Anti-TNFα Drugs to Uncomplexed Anti-TNFα Drugs The ratio of the complexed anti-TNFα drug to uncomplexed anti-TNFα drug is obtained by integrating the areas-under-the-curve for both the complexed anti-TNFα drug and the uncomplexed anti-TNFα drug and then dividing the resultant integration for the complexed anti-TNFα drug by the resultant integration for the uncomplexed anti-TNFα drug.

In one embodiment, the uncomplexed anti-TNFα drug is REMICADE™ having levels between about 0 ng and 100 ng in a sample. The amount of labeled-REMICADE™ is about 37.5 ng.

By using an internal control, e.g. Biocytin-Alexa 488, serum artifacts and variations from one experiment to another experiment can be identified and properly analyzed. The amount of internal control, e.g. Biocytin-Alexa 488, is from about 50 to about 200 pg per 100 µL analyzed.

The ratio of the labeled anti-TNFα drug, e.g. REMICADE™ or HUMIRA™, to the labeled internal control is obtained by integrating the areas-under-the-curve for both the labeled anti-TNFα drug and the labeled internal control and then dividing the resultant integration for the labeled anti-TNFα drug by the resultant integration for the labeled internal control.

The ratio of [(labeled-anti-TNFα Drug.Autoantibody)$_{complex}$]/[internal control] is obtained by integrating the area-under-the curve for the (labeled-anti-TNFα drug.Autoantibody)$_{complex}$ peak from a plot of signal intensity as a function of elution time from the size exclusion HPLC, and dividing this number by the resultant integration of the area-under-the-curve for the internal control peak from the plot. In some embodiments, the labeled anti-TNFα drug is labeled REMICADE™. In some other embodiments, the labeled anti-TNFα drug is labeled HUMIRA™.

Example 11: Determining the Ratio of Free and Complexed Labeled TNFα

This example describes a method for determining the amount of a complex of labeled-TNFα with either REMICADE™ or HUMIRA™ with reference to an internal standard.

By using an internal control, e.g. Biocytin-Alexa 488, serum artifacts and variations from one experiment to another experiment can be identified and properly analyzed. The amount of internal control, e.g. Biocytin-Alexa 488, is from about 1 to about 25 ng per 100 μL analyzed.

In one embodiment, the uncomplexed labeled TNFα has levels between about 50 ng and 150 ng in a sample. In certain instances, the amount of labeled-TNFα is about 100.0 ng.

Fluorophore (Fl)-labeled TNFα was incubated with patient serum to form the immunocomplex. A Fl-labeled small peptide, e.g. Biocytin-Alexa 488, was included as an internal control in each reaction. A standard curve was created by spiking in known concentrations of purified anti-TNFα drug and then extrapolating from the curve to determine the concentration in units of μg/mL.

The initial ratio of the Labeled-TNFα to the internal control is equal to 100. When the ratio of the Labeled-TNFα to the internal control falls below 95, the labeled-TNFα is inferred to be complexed with an anti-TNFα drug, e.g. Remicade™, Humira™. The ratio of the [Labeled-TNFα] to [internal control] is obtained by integrating the areas-under-the-curve for the Labeled-TNFα and for the internal control and then dividing the resultant integration for the Labeled-TNFα by the resultant integration for the internal control.

Example 12: Optimizing Anti-TNFα Drug Therapy by Measuring Anti-TNFα Drug and/or Anti-Drug Antibody (ADA) Levels This example describes methods for optimizing anti-TNFα drug therapy, reducing toxicity associated with anti-TNFα drug therapy, and/or monitoring the efficacy of therapeutic treatment with an anti-TNFα drug by measuring the amount (e.g., concentration level) of anti-TNFα drug (e.g., level of free anti-TNFα therapeutic antibody) and/or anti-drug antibody (ADA) (e.g., level of autoantibody to the anti-TNFα drug) in a sample from a subject receiving anti-TNFα drug therapy. Accordingly, the methods set forth in the present example provide information useful for guiding treatment decisions, e.g., by determining when or how to adjust or modify (e.g., increase or decrease) the subsequent dose of an anti-TNFα drug, by determining when or how to combine an anti-TNFα drug (e.g., at an increased, decreased, or same dose) with one or more immunosuppressive agents such as methotrexate (MTX) or azathioprine, and/or by determining when or how to change the current course of therapy (e.g., switch to a different anti-TNFα drug).

For purposes of illustration only, the following scenarios provide a demonstration of how the methods of the present invention advantageously enable therapy to be optimized and toxicity (e.g., side-effects) to be minimized or reduced based upon the level of anti-TNFα drug (e.g., level of free anti-TNFα therapeutic antibody) and/or ADA (e.g., level of autoantibody to the anti-TNFα drug) in a sample from a subject receiving anti-TNFα drug therapy. The levels of the anti-TNFα drug and ADA can be measured with the novel assays described herein.

Scenario #1: High Level of Anti-TNFα Drug with Low Level of Anti-Drug Antibody (ADA).

Drug levels=10-50 ng/10 μl; ADA levels=0.1-2 ng/10 μl. Patient samples having this profile include samples from patients BAB and JAA on visit 10 ("V10"). See, FIG. 16b.

Patients receiving anti-TNFα drug therapy and having this particular profile should be treated with immunosuppressive drugs like azathioprine (AZA) along with the anti-TNFα drug (e.g., infliximab).

Scenario #2: Medium Level of Anti-TNFα Drug with Low Level of ADA.

Drug levels=5-20 ng/10 μl; ADA levels=0.1-2 ng/10 μl. Patient samples having this profile include samples from patients DGO, JAG, and JJH on V10. See, FIG. 16b.

Patients receiving anti-TNFα drug therapy and having this particular profile should be treated with immunosuppressive drugs like azathioprine (AZA) along with a higher dose of the anti-TNFα drug (e.g., infliximab). One skilled in the art will know of suitable higher or lower doses to which the current course of therapy can be adjusted such that drug therapy is optimized, e.g., a subsequent dose that is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher or lower than the current dose.

Scenario #3: Medium Level of Anti-TNFα Drug with Medium Level of ADA.

Drug levels=5-20 ng/10 μl; ADA levels=0.5-10 ng/10 μl. Patient samples having this profile include samples from patient JMM on visit 10 ("V10") and patient J-L on visit 14 ("V14"). See, FIG. 16b.

Patients receiving anti-TNFα drug therapy and having this particular profile should be treated with a different drug. As a non-limiting example, a patient on infliximab (IFX) therapy and having medium levels of IFX and ADA (i.e., HACA) should be switched to therapy with adalimumab (HUMIRA™).

Scenario #4: Low Level of Anti-TNFα Drug with High Level of ADA.

Drug levels=0-5 ng/10 μl; ADA levels=3.0-50 ng/10 μl. Patient samples having this profile include samples from all patients on V14 in FIG. 16b.

Patients receiving anti-TNFα drug therapy and having this particular profile should be treated with a different drug. As a non-limiting example, a patient on infliximab (IFX) therapy and having a low level of IFX with a high level of ADA (i.e., HACA) should be switched to therapy with adalimumab (HUMIRA™).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for optimizing therapy and/or reducing toxicity to an anti-TNFα drug in a subject receiving therapy with said anti-TNFα drug, said method comprising:
   (a) measuring the level of said anti-TNFα drug in a first sample from said subject, wherein said anti-TNFα drug is measured with an assay comprising:
      (i) contacting said first sample with an amount of a labeled TNFα to form a first complex comprising said labeled TNFα with said anti-TNFα drug; and detecting an amount of said first complex by size exclusion chromatography and comparing the amount detected to a standard curve of known amounts of the anti-TNFα drug, thereby measuring said level of said anti-TNFα drug;
   (b) measuring the level of an autoantibody to said anti-TNFα drug in a second sample from said subject; and
   (c) determining a subsequent course of therapy for said subject based upon the levels of said anti-TNFα drug and said autoantibody,
thereby optimizing therapy and/or reducing toxicity to said anti-TNFα drug.

2. The method of claim 1, wherein the subsequent course of therapy comprises co-administering an immunosuppressive drug with said anti-TNFα drug when said level of said anti-TNFα drug is a high level and said level of said autoantibody is a low level.

3. The method of claim 1, wherein the subsequent course of therapy comprises increasing the level of said anti-TNFα drug and co-administering an immunosuppressive drug when said level of said anti-TNFα drug is a medium level and said level of said autoantibody is a low level.

4. The method of claim 1, wherein the subsequent course of therapy comprises administering a different anti-TNFα drug when said level of said anti-TNFα drug is a medium level and said level of said autoantibody is a medium level.

5. The method of claim 1, wherein the subsequent course of therapy comprises administering a different anti-TNFα drug when said level of said anti-TNFα drug is a low level and said level of said autoantibody is a high level.

6. The method of claim 4, wherein adalimumab is administered instead of infliximab.

7. The method of claim 1, wherein said autoantibody is measured with an assay comprising:
   (i) contacting said second sample with an amount of a labeled anti-TNFα drug to form a second complex comprising said labeled anti-TNFα drug with said autoantibody; and
   (ii) detecting said second complex by size exclusion chromatography, thereby measuring said level of said autoantibody.

8. The method claim 1, wherein said anti-TNFα drug is a member selected from the group consisting of infliximab, etanercept, adalimumab, certolizumab pegol, and combinations thereof.

9. The method of claim 1, wherein said anti-TNFα drug is infliximab.

10. The method of claim 1, wherein said anti-TNFα drug is adalimumab.

11. The method of claim 1, wherein said anti-TNFα drug is etanercept.

12. The method of claim 1, wherein said anti-TNFα drug is certolizumab pegol.

13. The method of claim 1, wherein said measured anti-TNFα drug is quantitated.

14. The method of claim 1, wherein said measured autoantibody is quantitated.

15. The method of claim 1, wherein both of said first and second samples are serum samples.

16. The method of claim 1, wherein both of said first and second samples are obtained from said subject during therapy with said anti-TNFα drug.

17. The method of claim 1, wherein said autoantibody is a member selected from the group consisting of human anti-mouse antibody (HAMA), human anti-chimeric antibody (HACA), human anti-humanized antibody (HAHA), and combinations thereof.

18. The method of claim 2, wherein said immunosuppressive drug is selected from the group consisting of methotrexate, azathioprine, metabolites thereof, and combinations thereof.

19. The method of claim 2, wherein said level of said anti-TNFα drug is between about 10 to about 50 ng/10 µl and said level of said autoantibody is between about 0.1 to about 2.0 ng/10 µl.

20. The method of claim 3, wherein said level of said anti-TNFα drug is between about 5.0 to about 20 ng/10 µl and said level of said autoantibody is between about 0.1 to about 2.0 ng/10 µl.

21. The method of claim 4, wherein said level of said anti-TNFα drug is between about 5.0 to about 20 ng/10 µl and said level of said autoantibody is between about 0.5 to about 10 ng/10 µl.

22. The method of claim 5, wherein said level of said anti-TNFα drug is between 0 to about 5 ng/10 µl and said level of said autoantibody is between about 3.0 to about 50 ng/10 µl.

* * * * *

SEQUENCE LISTING

<160> NUMBER OF SEQ ID NOS: 3

<210> SEQ ID NO 1
<211> LENGTH: 233
<212> TYPE: PRT
<213> ORGANISM: Homo sapiens
<220> FEATURE:
<223> OTHER INFORMATION: soluble form of tumor necrosis factor-alpha
      (TNF-alpha)

<400> SEQUENCE: 1

Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
                35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
                115                 120                 125

Glu Gly Leu Tyr Leu Ile Tyr Ser Gln Val Leu Phe Lys Gly Gln Gly
                130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
                195                 200                 205

Ser Ala Glu Ile Asn Arg Pro Asp Tyr Leu Asp Phe Ala Glu Ser Gly
                210                 215                 220

Gln Val Tyr Phe Gly Ile Ile Ala Leu
225                 230

<210> SEQ ID NO 2
<211> LENGTH: 22
<212> TYPE: PRT
<213> ORGANISM: Artificial Sequence
<220> FEATURE:
<223> OTHER INFORMATION: synthetic antibody epitope of tumor necrosis
      factor alpha (TNF-alpha), residues 136-157

<400> SEQUENCE: 2

Tyr Ser Gln Val Leu Phe Lys Gly Gln Gly Cys Pro Ser Thr His Val
1               5                   10                  15

Leu Leu Thr His Thr Ile
                20

<210> SEQ ID NO 3
<211> LENGTH: 22
<212> TYPE: PRT

```
<213> ORGANISM: Artificial Sequence
<220> FEATURE:
<223> OTHER INFORMATION: synthetic antibody epitope of tumor necrosis
      factor alpha (TNF-alpha), residues 164-185

<400> SEQUENCE: 3

Tyr Gln Thr Lys Val Asn Leu Leu Ser Ala Ile Lys Ser Pro Cys Gln
1               5                   10                  15

Arg Glu Thr Pro Glu Gly
            20
```